United States Patent
Ruff et al.

(10) Patent No.: US 11,684,330 B2
(45) Date of Patent: Jun. 27, 2023

(54) IMAGING SYSTEMS AND METHODS

(71) Applicant: OXOS Medical, Inc., Atlanta, GA (US)

(72) Inventors: Evan Ruff, Atlanta, GA (US); Gregory Kolovich, Savannah, GA (US); Dev Mandavia, Atlanta, GA (US); Dhruv Vishwakarma, Suwanee, GA (US); Igor Zamlinsky, Roswell, GA (US); Sean Dolan, Atlanta, GA (US)

(73) Assignee: OXOS Medical, Inc., Atlanta, GA (US)

( * ) Notice: Subject to any disclaimer, the term of this patent is extended or adjusted under 35 U.S.C. 154(b) by 0 days.

(21) Appl. No.: 17/658,905

(22) Filed: Apr. 12, 2022

(65) Prior Publication Data

US 2023/0039343 A1    Feb. 9, 2023

Related U.S. Application Data

(62) Division of application No. 17/480,929, filed on Sep. 21, 2021, now Pat. No. 11,382,582.
(Continued)

(51) Int. Cl.
*A61B 6/08* (2006.01)
*A61B 6/00* (2006.01)

(52) U.S. Cl.
CPC .............. *A61B 6/4405* (2013.01); *A61B 6/08* (2013.01); *A61B 6/463* (2013.01); *A61B 6/467* (2013.01); *A61B 6/5247* (2013.01); *A61B 6/547* (2013.01)

(58) Field of Classification Search
CPC . A61B 2090/371; A61B 5/742; A61B 5/7475; A61B 5/066; A61B 90/37; A61B 1/00045; A61B 1/05; A61B 90/361; A61B 34/25; A61B 2018/00982; A61B 2034/2055; A61B 6/5229; A61B 1/0005; A61B 1/00009; A61B 2034/107; A61B 1/00193; A61B 2090/365; A61B 1/051; A61B 90/90; A61B 2090/368; A61B 2090/372; A61B 2090/3937; A61B 2034/258; A61B 5/0077; A61B 90/39; H04N 13/302; G06T 19/006;
(Continued)

(56) References Cited

U.S. PATENT DOCUMENTS 4,054,881 A    10/1977    Raab
6,022,143 A    2/2000    Helmreich
(Continued)

FOREIGN PATENT DOCUMENTS

DE    102010008552    11/2014

OTHER PUBLICATIONS

U.S. Appl. No. 17/201,981, filed Mar. 15, 2021, Franklin et al.
(Continued)

*Primary Examiner* — Don K Wong
(74) *Attorney, Agent, or Firm* — Levine Bagade Han LLP

(57) ABSTRACT

Methods and systems for X-ray and fluoroscopic image capture and, in particular, to a versatile, multimode imaging system incorporating a handheld X-ray emitter operative to capture non-invasive images of a target; a stage operative to capture static X-ray and dynamic fluoroscopic images of the target; a system for the tracking and positioning of the X-ray emission to improve safety of obtaining X-ray images as well as improve the quality of X-ray images. Where the devices can automatically limit the field of the X-ray emission.

14 Claims, 39 Drawing Sheets

Related U.S. Application Data

(60) Provisional application No. 63/203,864, filed on Aug. 2, 2021.

(58) Field of Classification Search
CPC ......... G06T 2219/2004; G06T 2210/41; G06T 7/55; G06T 7/70; G06T 2207/10021; G06T 19/20; G06T 2207/10116; G06T 7/30
See application file for complete search history.

(56) References Cited

U.S. PATENT DOCUMENTS

| | | | |
|---|---|---|---|
| 6,078,036 A | 6/2000 | Cook et al. | |
| 6,173,033 B1 | 1/2001 | Klingenbeck-Regn et al. | |
| 6,266,142 B1 | 7/2001 | Junkins et al. | |
| 6,369,564 B1 | 4/2002 | Khalfin et al. | |
| 6,377,041 B1 | 4/2002 | Jones, Jr. et al. | |
| 6,400,139 B1 | 6/2002 | Khalfin et al. | |
| 6,624,626 B2 | 9/2003 | Khalfin | |
| 6,762,600 B2 | 7/2004 | Khalfin | |
| 8,821,017 B2 | 9/2014 | Lalena et al. | |
| 8,867,705 B2 | 10/2014 | Lalena et al. | |
| 8,873,712 B2 | 10/2014 | Wang et al. | |
| 9,155,509 B2 | 10/2015 | Lalena et al. | |
| 9,474,502 B2 | 10/2016 | Kurze | |
| 9,833,209 B2 | 12/2017 | Belei | |
| 10,076,302 B2 | 9/2018 | Franklin et al. | |
| 10,098,609 B2 | 10/2018 | Kim et al. | |
| 10,143,428 B2 | 12/2018 | Eun et al. | |
| 10,188,365 B2 | 1/2019 | Lee et al. | |
| 10,463,325 B2 | 11/2019 | Foos et al. | |
| 10,531,850 B2 | 1/2020 | Tkaczyk et al. | |
| 10,542,949 B2 | 1/2020 | Lee et al. | |
| 10,568,601 B2 | 2/2020 | Tkaczyk et al. | |
| 10,568,602 B2 | 2/2020 | Tkaczyk et al. | |
| 10,702,224 B1 | 7/2020 | Vanhooser | |
| 10,729,399 B2 | 8/2020 | Butani et al. | |
| 11,006,921 B2 | 5/2021 | Franklin et al. | |
| 2004/0105526 A1 | 6/2004 | Zhang et al. | |
| 2005/0063512 A1 | 3/2005 | Maschke | |
| 2005/0129175 A1 | 6/2005 | Shen et al. | |
| 2014/0005555 A1* | 1/2014 | Tesar | A61B 17/00 600/476 |
| 2017/0119339 A1 | 5/2017 | Johnson et al. | |
| 2017/0277831 A1 | 9/2017 | Ruff et al. | |
| 2018/0235566 A1 | 8/2018 | Tamersory et al. | |
| 2020/0289079 A1 | 9/2020 | Tanno et al. | |
| 2020/0289207 A1 | 9/2020 | Ruff et al. | |
| 2020/0289208 A1 | 9/2020 | Ruff et al. | |
| 2021/0169438 A1 | 6/2021 | Ruff et al. | |

OTHER PUBLICATIONS

US Code of Federal Regulations applying to the Food and Drug Administration Department of Health and Human Services (e.g., 21 CFR part 1020 incorporated by reference herein.) https://www.accessdata.fda.gov/scripts/cdrh/cfdocs/cfcfr/cfrsearch.cfm.
White Paper/CARESTREAM DRX-Revolution Mobile X-ray System, 4 pages, Carestream Health, Inc. 2012. CAT 200 0016 8.5×11 Sep. 2012, www.carestream.com.

* cited by examiner

IMAGING SYSTEMS AND METHODS

REFERENCE TO RELATED APPLICATIONS

This application is a divisional of U.S. patent application Ser. No. 17/480,929 filed Sep. 21, 2021, which claims priority to U.S. Provisional Application No. 63/203,864 filed Aug. 2, 2021, the contents of which are incorporated herein by reference in their entireties.

FIELD OF THE INVENTION

Improved methods and systems for X-ray and fluoroscopic image capture and, in particular, to a versatile X-ray emitter operative to capture images of a target while the system is configured to track and position the X-ray emission relative to an image sensor that generates the X-ray image using the X-ray emission. The method and device permit generating a first virtual representation of the detecting perimeter of the image sensor and a second virtual representation of the energy emission using the real-time positioning data. These virtual representations can be displayed on a real-time image of the examination area where the first virtual representation of the detecting perimeter is superimposed with the second virtual representation of the energy emission while displaying the real-time image of the examination area to permit the operator to confirm a location of the detecting perimeter and a location of the X-ray emission.

BACKGROUND OF THE INVENTION

Current fluoroscopic machines for orthopedic surgery tether a radiation source to an image intensifier by way of a large, fixed 'c-arm.' Manipulation of these larger, less portable machines is difficult and time-consuming. It is frequently necessary to reposition the subject to fit the attainable field of view, which can be problematic during sensitive stages of a procedure. Thus, while c-arms are ergonomically suitable for surgical treatment of the spine and larger joints, existing units are heavy and cumbersome with respect to hand/wrist/arm and foot/ankle/leg extremity surgery, where relevant anatomy is smaller and more moveable by the surgeon. Existing fluoroscopic machines are also expensive and emit large doses of radiation. In many cases, these larger radiation doses are not required for more delicate procedures, on extremities, for example, unnecessarily exposing the patient and surgeon to these higher doses.

There is an outstanding need, therefore, for a small, lightweight system and method that allows the X-ray operator or surgeon to capture X-rays without repositioning equipment. At the same time, such a system should allow maneuverability of the X-ray emitter and tracking of the emitter relative to the image sensor and use the resulting positioning data to improve the safety of the X-ray system as well as to reduce the need for obtaining multiple X-ray images due to inadequate positioning of the X-ray emitter relative to the detector.

There is also a need for improving the quality of an X-ray or fluoroscopic capture where the quality is related to a number of physical attributes of the subject. These elements dictate a set of technique factors (e.g., power, current, time) that control the emission characteristics of the radiation source. It is the responsibility of the device operator to set these factors in such a combination that the interpreter can see the necessary visual elements without exposing the subject to excess radiation.

Setting these technique factors can be complex. In order to relieve the operator of the burden of setting these techniques manually, existing fluoroscopic devices have implemented an automatic process. The typical approach uses a software or a hardware dose detector on the plate that gradually fills as radiation is added to the exposure. This approach has a number of problems.

There remains a need for applying the capabilities of the new generation of systems having complex sensor arrays, capable of directly measuring a number of the physical elements required for exposure calculation and using these improved systems to apply learning algorithms that assist the medical practitioners in obtaining an optimal radiological image.

By utilizing sensors across the full spectrum of the improved systems and subjects, as well as robust machine learning techniques, it is possible to compute the necessary techniques before the patient is exposed to radiographic energy, which can eliminate motion artifacts and create an outstanding capture of the radiological image, all while reducing an exposure dose.

SUMMARY OF THE INVENTION

The invention relates to an improved versatile, multimode radiographic systems and methods, allowing the surgeon to operate on a patient without interference, and capture static and dynamic X-rays and other still and video imagery without repositioning equipment, the subject, or the surgeon.

Both X-ray emitters and detectors are described. One variation of a novel emitter allows for portable control of the emitter. Such an emitter can be lightweight and extremely maneuverable. Variations include a portable emitter that is a handheld unit. Alternatively, the portable emitter can be affixed to a mounting structure that is either automated/controllable or simply bears the weight of the emitter to prevent the user from constantly holding the emitter. In additional variations, the emitter can be designed so that it is releasably coupleable with a mounting structure, which allows improved portability when needed and coupling to a mounting structure when desired. The emitter may include both an X-ray emitter along with at least one additional imaging modality such as a digital camera for producing a visual image, a thermal image, and an infrared image of a patient for the purposes of aiding diagnostic, surgical, and non-surgical interventions. Clearly, the systems and methods described herein can be used for non-medical applications where non-invasive imaging is desirable.

Ergonomic controls make acquisition of images easier and faster, and a built-in display facilitates easy-to-use control functions. The device senses its distance from the subject and will block the activation and discharge of radiation if the X-ray tube is not at a safe distance, i.e., too close to the patient. The minimum distance can be defined in software and is adjustable based on the intended use and other factors. The system automatically and intelligently manages its power state through the implementation and use of an inertial measurement unit (IMU) and various timing components.

The X-ray emitter may be used with any available X-ray detector. One option is to mount the emitter in a fixture, including a properly aligned detector plate, much like a traditional c-arm, though much smaller and more capable. An alternate variation is described herein and includes use of an emitter with a distinct X-ray capture stage, disclosed in detail, which automatically pivots, orients, and aligns itself with the emitter to maximize exposure, quality, and safety.

The inventive X-ray stage comprises a statically fixed platform, positioned during the outset of surgery, with an open cavity containing an X-ray sensor, an X-ray sensor positioning system, an emitter tracking system, a shielding system, and a control unit. Optionally, the system can utilize an external display monitor or any other method for reviewing the captured image.

In one variation, an improved X-ray system under the present disclosure allows for a method of assisting an operator during non-invasive imaging where the X-ray system includes an imaging sensor located adjacent to an examination area, and where the imaging sensor includes a detecting perimeter adjacent to a plurality of position tracking implements that are fixedly positioned relative to the imaging sensor, the method comprising: positioning an emitting apparatus at a distance from the imaging sensor, the emitting apparatus including a camera system, a position tracking apparatus and an aperture opening configured to pass an energy emission; orienting the emitting apparatus such that the aperture opening faces towards the examination area; detecting one or more of the plurality of position tracking implements using the position tracking apparatus to produce a real-time positioning data of the emitting apparatus relative to the image detector; generating a first virtual representation of the detecting perimeter and a second virtual representation of the energy emission using the real-time positioning data; displaying on a display a real-time image of the examination area using the camera system; and superimposing the first virtual representation of the detecting perimeter and the second virtual representation of the energy emission on the display while displaying the real-time image of the examination area to permit the operator to confirm a location of the detecting perimeter and a location of the X-ray emission using the display. The methods can include one or more additional displays. For example, a first display can be positioned on the emitting apparatus while a second or more display can be located adjacent to the operator or in remote locations.

One example of a non-invasive imaging system for confirming placement of an object positioned in an examination area includes a non-invasive imaging sensor (e.g., an X-ray imaging sensor) having a detecting perimeter configured to receive an emission energy allowing for generation of a non-invasive image of the object when the object is positioned on or adjacent to the non-invasive imaging sensor; a plurality of position tracking implements (line-of-sight sensors and/or non-line-of-sight sensors) fixedly positioned relative to the non-invasive imaging sensor; an emitting apparatus having an aperture opening that is configured to emit the emission energy in an emission profile, the emitting apparatus further including a position tracking apparatus configured to produce a positioning signal and a camera system configured to produce an image signal, where the positioning signal is produced upon detecting one or more of the plurality of position tracking implements; a display configured to receive the image signal to produce a real-time image having a point of view from the aperture opening; and a control system configured to convert the positioning signal into a plurality of positioning data of the emitting apparatus relative to the non-invasive imaging sensor, the control system further configured to use the positioning data to generate a first virtual image of the detecting perimeter and a second virtual image of the emission profile, where the control system is further configured to display the first virtual image and the second virtual image with the real-time image on the display.

A variation of the methods and systems described herein include a camera system that comprises a first camera device and a second camera device, where detecting one or more of the plurality of position tracking implements comprises using the first camera device and displaying the real-time image of the examination area on the display comprises using the second camera device.

The camera device and/or camera system can use any number of cameras or image sensors. In variations of the system, the image sensor(s) are positioned adjacent to the X-ray aperture opening to match a field-of-view of the aperture opening when obtaining images of the object being scanned. In practice, positioning the camera adjacent to the aperture opening comprises positioning the camera adjacent to the aperture opening in a face of the emitting apparatus as opposed to an aperture that controls passage of the emitted energy. The camera system can be configured to take still images as well as real-time video. In one variation, the camera device can include an infrared camera. In addition, the real-time image can comprise a digital image, analog image, digitized image, virtual image, and a combination thereof.

Variations of the methods and systems described herein can include delivering the energy emission from the emitting apparatus after superimposing the first virtual representation of the detecting perimeter and the second virtual representation of the energy emission on the display while displaying the real-time image of the examination area.

The systems and method can further include a safety feature when orienting the emitting apparatus towards an object in the examination area, where delivering the energy emission is prevented unless a distance between the emitting apparatus and the object is greater than a minimum distance.

The systems and methods described herein can also alter a size of an aperture adjacent to the aperture opening using the real-time positioning data.

Additional variations of the methods and systems include altering the second virtual representation in response to the aperture opening being offset from an orthogonal orientation relative to the imaging sensor.

Variations of the system can include platforms that have a planar surface allowing for positioning of the object. Alternatively, a platform can include a support frame that allows securing of the object over a free space such that the portion of the object located in the free space can be viewed or inspected either entirely or substantially around the perimeter of the object.

In the systems, devices, and methods described herein, which position the emitter and sensor in alignment or operative alignment, the degree of alignment can include any industry specifications that dictate alignment. For example, for medical applications, alignment of the systems and methods described herein can include a degree of alignment required to comply with the US Code of Federal Regulations applying to the FOOD AND DRUG ADMINISTRATION DEPARTMENT OF HEALTH AND HUMAN SERVICES (e.g., 21 CFR part 1020 incorporated by reference herein.) E.g., under 21 CFR, neither a length nor a width of the X-ray field in the plane of the image receptor (sensor) shall exceed that of the visible area of the image receptor (sensor) by more than 3 percent of the source-to-image receptor distance (SID) and the sum of the excess length, and the excess width shall be no greater than 4 percent of the SID and Any error in alignment shall be determined along the length and width dimensions of the X-ray field which pass through the center of the visible area of the image receptor. In other applications or alternate jurisdictions, the alignment discussed herein can vary to meet the respective requirements. Alternatively, variations of the systems, devices, and methods can include such metrics as obtaining a near orthogonal positioning between an emitter and receptor.

As with alignment, a minimum or maximum distance between an emitter and receptor can be established by industry standards. In one example, using the above FDA regulations, a maximum source-image receptor distance of less than 45 cm and means shall be provided to limit the source-skin distance to not less than 19 cm.

In use, the stage precisely tracks the position and angle of the X-ray emission, positioning and tilting the embedded sensor exactly to capture a precise, high-quality X-ray image. The stage uses less power, corrects for any skew or perspective in the emission, allows the subject to remain in place, and allows the surgeon's workflow to continue uninterrupted.

In a "clinical" embodiment, an X-ray capture stage is statically positioned, with the emitter using the positioning to ensure the emission is only fired when the emission can be positively captured by the active area of the capture stage. Firing is also immediately terminated if acquisition of this positive capture is lost.

This application is related to the following: U.S. Pat. No. 10,076,302 issued on Sep. 18, 2018, and U.S. Pat. No. 11,006,921 issued on May 18, 2021; U.S. application Ser. No. 17/201,981 filed on Mar. 15, 2021, Ser. No. 17/163,878 filed on Feb. 1, 2021, (U.S. Publication US20210169438), Ser. No. 16/817,337 filed on Mar. 12, 2020, (U.S. Publication US20200289207), Ser. No. 16/818,561 filed on Mar. 13, 2020, (U.S. Publication US20200289208) the entirety of each of which is incorporated by reference.

DETAILED DESCRIPTION OF THE PREFERRED EMBODIMENTS

Figure 1A:
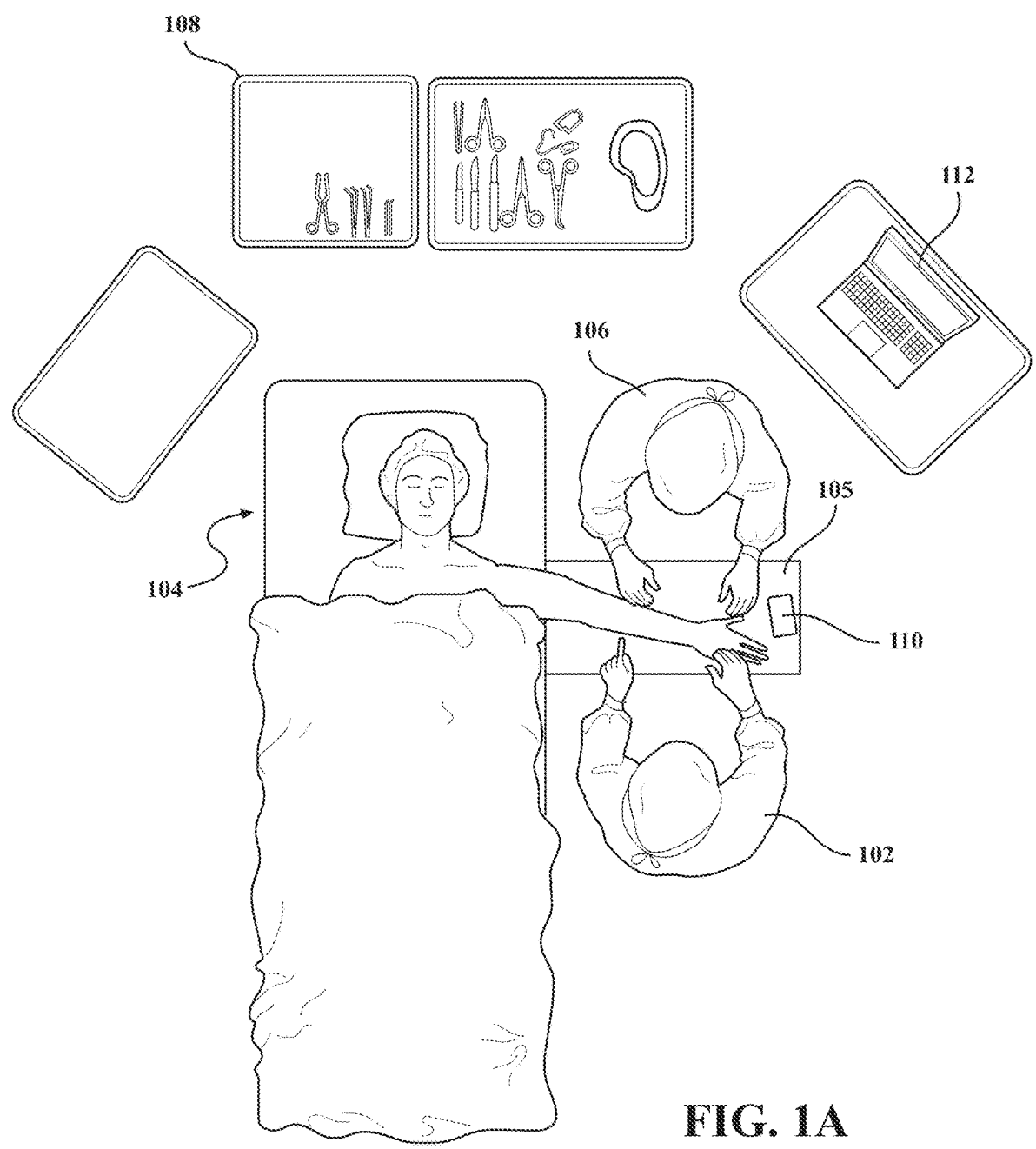
FIG. 1A depicts an example of an operating room layout for the use of the X-ray imaging system in a standard surgery of an extremity case.

FIG. 1A depicts an example of an operating room layout for the use of an imaging system in a standard surgery of an extremity case. In this example, the surgeon 102 is operating on the patient's left hand. The patient 104 is lying in the supine position with the left upper extremity prepped and draped on a hand table 105 in the abducted position. The surgeon sits adjacent to the patient's side while a surgical assistant 106 sits across the hand table adjacent to the patient's head. Surgical instruments and equipment are laid out on the back table 108 immediately behind the surgical assistant.

In one variation, the imaging system uses X-ray imaging. As such, a sterilized X-ray emitter 110, according to the invention, is placed on the surgical hand table 105 for use. A monitor 112 is positioned on a stand immediately adjacent to the hand table whereby X-ray, fluoroscopic, thermal, and digital images can be wirelessly transferred from the X-ray imaging system to the screen for surgeon view. The emitter 110 allows the surgeon to hold it with one hand while operating another instrument, such as a drill in the other hand. A detector stage, according to the invention, may be placed on or in the table 105 to gather radiographic imagery for storage and/or viewing on an external monitor such as device 112. As discussed herein, the emitter can be handheld or can be affixed to a mounting structure that is either automated/controllable or simply bears the weight of the emitter to prevent the user from constantly holding the emitter.

Figure 1B:
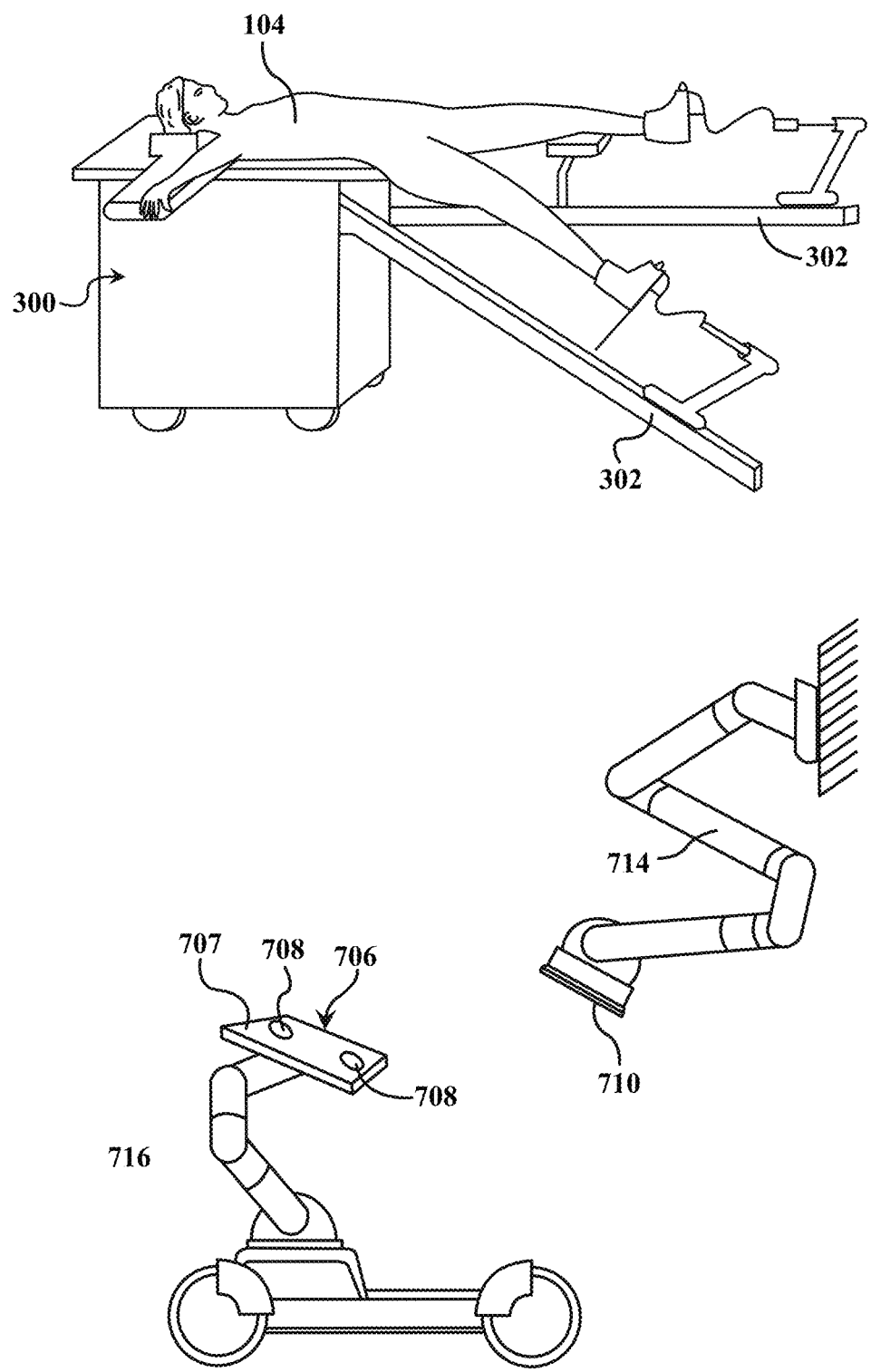
FIGS. 1B and 1C depict an alternate example of an operating room layout for the use of the imaging system with a specialized operating table that improves access to an area of a patient.
Figure 1C:
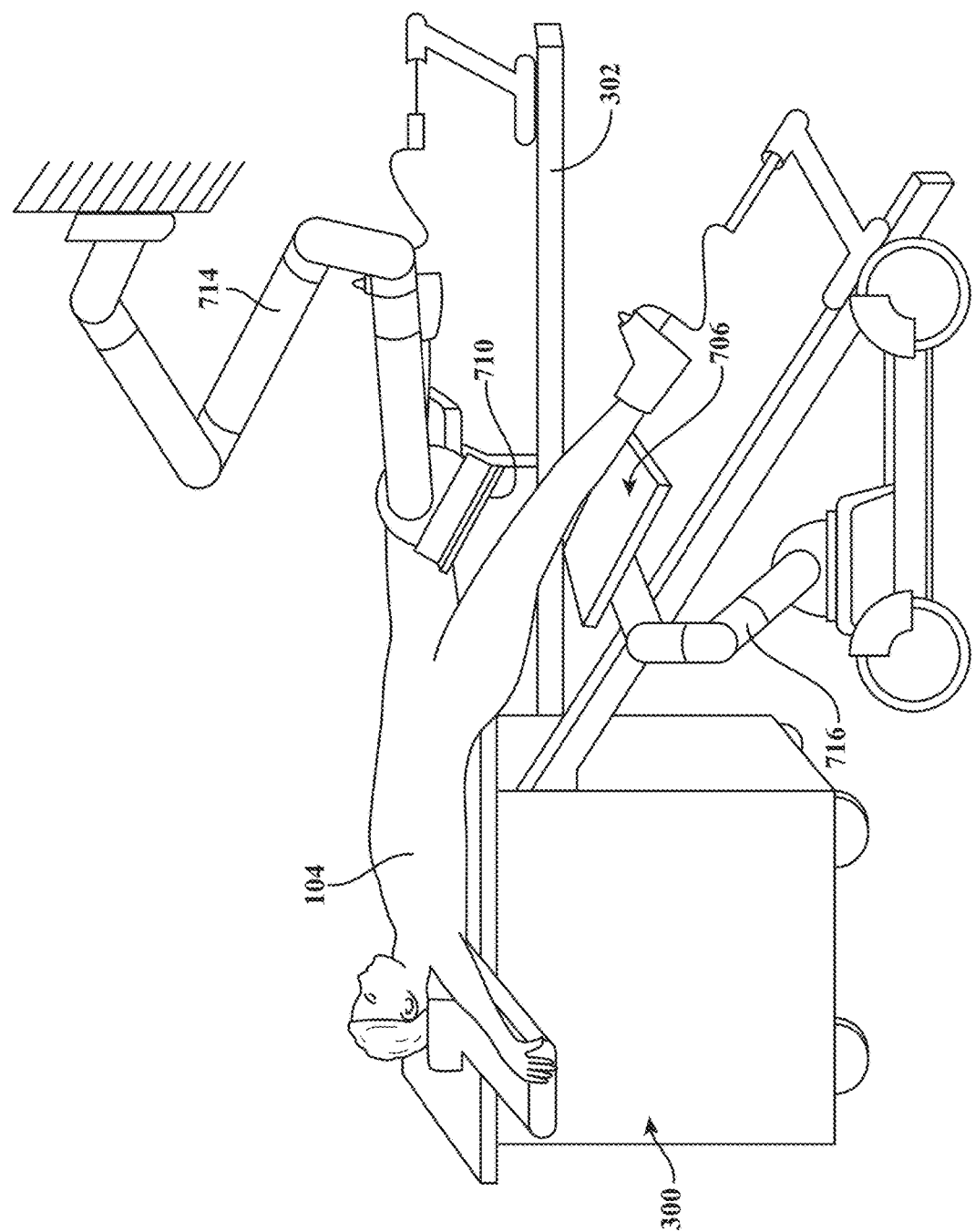

FIG. 1B illustrates an additional variation of a system including a sensor 706 and an emitter 710 for use with a specialized operating table 300. As shown, the operating table 300 includes structures 302 that stabilize the patient while allowing increased access around the patient's organs since a portion of the organ is suspended in free space. In this variation, a shell 707 containing the sensor 706 (as discussed below) is coupled to a first boom or arm 716. The arm/boom 716 allows for movement of the sensor 706. In an alternate variation, the boom 716 can be automated such that the sensor 706 is coupled directly to a controllable boom 716. Likewise, the emitter 710 is coupled to a second arm or boom 714 that can be affixed to a wall, ceiling, or portable frame structure. FIG. 1C illustrates positioning of the sensor 706 and boom 716 adjacent to a body part of the patient 104 such that the emitter 710 can be positioned as desired by the operator or medical practitioner. In variations of the system, the boom or arm can also house components of the device, such as a heat sink, power supply, etc., allowing for a more compact and easy to maneuver emitter. In addition, either boom can be designed with features to aid the physician in performing the procedure. For example, the boom can incorporate a locking system so that the physician can position either the sensor 706 and/or emitter 710 and then lock the associated boom into position. Additionally, or in combination, booms can incorporate memory positioning such that the boom can automatically retract away from the surgical space to a pre-determined location such that it automatically moves out of the way of the physician when performing a procedure. In addition, memory locations can include the "last location" of the emitter or sensor, such that the system can automatically reposition the components in their last position prior to being moved away from the surgical space.

As discussed herein, the systems described herein can include one or more distance sensors 708 located on the image sensor and/or the operating table or other region of the working area. The distance sensor(s) 708 allows measurement of any space between the body part or anatomy placed on the image sensor, operating table, and/or working area. As noted below, such an additional measurement will allow correct measurement of the thickness of the body structure if there is a gap or space between the image sensor, operating table, and/or working area and the body structure.

Figure 2:
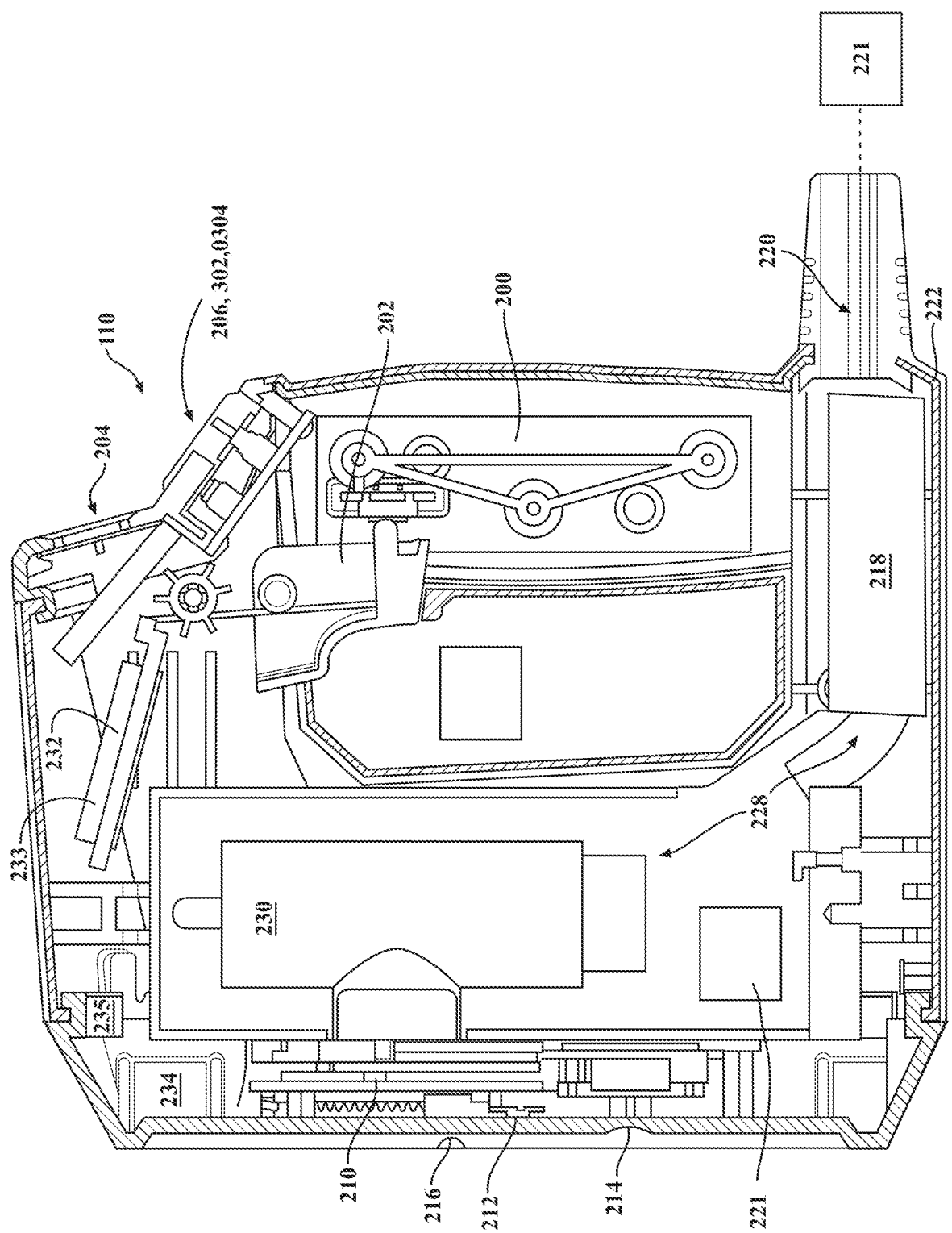
FIG. 2 is a simplified schematic representation of an X-ray emitter according to the invention.

FIG. 2 is a simplified schematic representation of an X-ray emitter according to the invention. The general configuration of the device is to be handheld, lightweight, and extremely portable. The device preferably has a rounded, contoured handle to ergonomically fit the surgeon's hand and better direct fluoroscopy, digital and thermal imagery to the extremity and surgical field.

In one variation, the back of the emitter 110 can include a control panel where at least three different modes of operation can be activated: fluoroscopic mode, digital picture mode, or infrared thermal imaging mode. Once activated, each mode is controlled in the front of the device by a trigger 202. Pressing the trigger once activates the device to take a single image (i.e., single X-ray or digital picture). Different modes of operation may be activated in different. As one example, holding the trigger 12 down may activate live fluoroscopy, digital video, or infrared thermal imaging. FIG. 2 also illustrates the emitter 110 as being coupled to a power supply 221. The power supply can be a battery 221 located remotely from or within the emitter 110. Alternatively, or in combination, the power supply 221 can be coupled via wiring between the emitter 110 and power supply 221. In an additional variation, the battery 221 can be positioned within the emitter 110 and used in addition to a remote power supply 221 such that the emitter 110 can be disconnected from the external power supply temporarily, with the internal battery 221 used to provide power.

Figure 3:
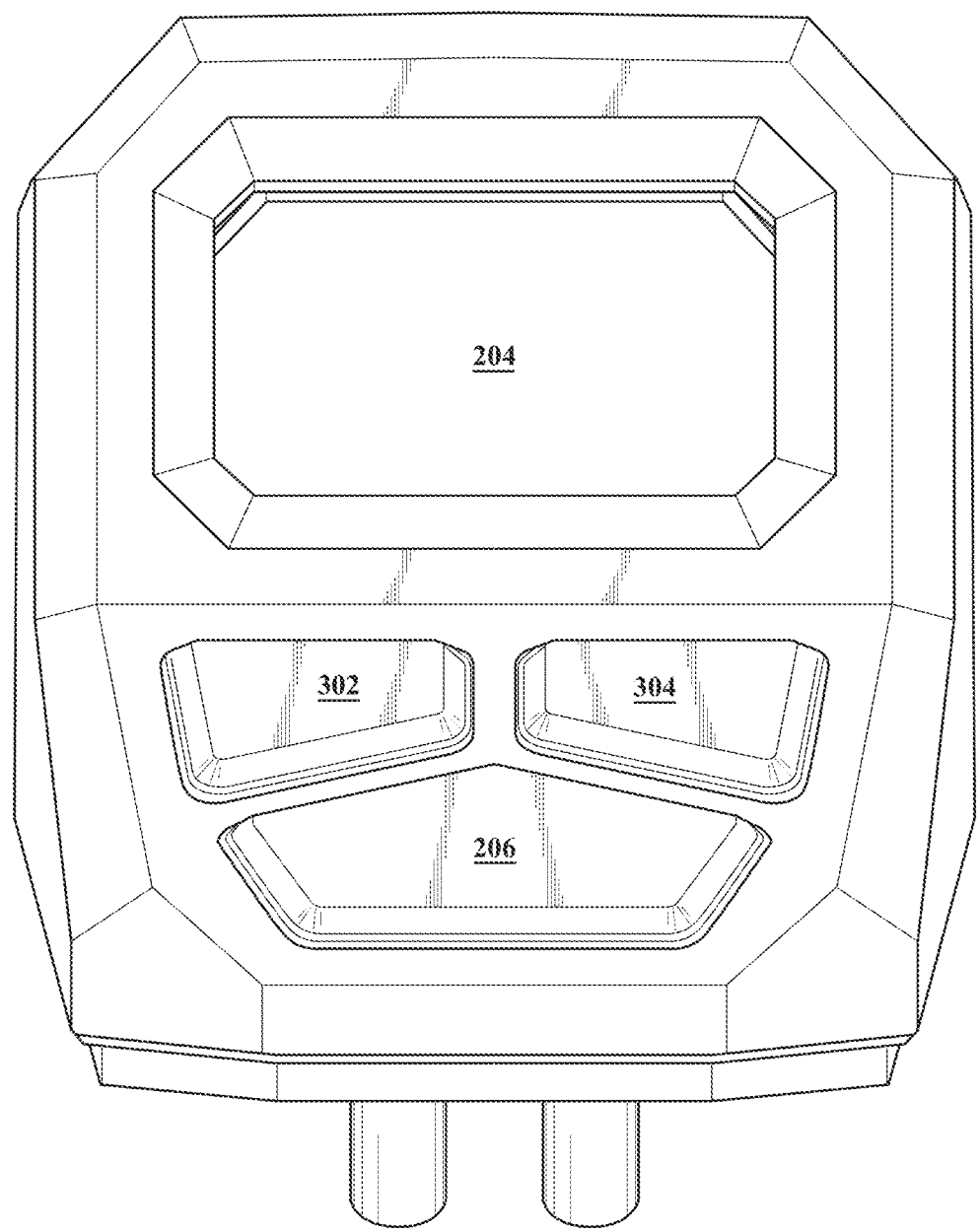
FIG. 3 illustrates one embodiment of a control panel for use with an emitter.

FIG. 3 illustrates one embodiment of the control panel for use with the emitter. The control panel is located on the rear of the emission handle and controls the various inputs and outputs of the system. The control panel is easily accessible for the user and is ergonomically designed to ease the manipulation of the emitter. The control panel comprises a large, clear screen 204 (i.e., LCD or OLED), a control button 302 located on the left of the unit, a control button 304 located on the right of the unit, and a center, clickable toggle button 206 located in the center.

Display screen 204 displays images and a digital control panel to control fluoroscopic, digital camera and infrared settings. The control panel may include a touch screen. Toggle button 206 controls power input in fluoroscopic and infrared modes and digital zoom in the picture mode. One variation of an emitter configuration houses a dynamic X-ray collimating cone 210, digital camera lens 212, infrared camera 214 and distance sensor 216. The digital and infrared cameras preferable use charge-coupled device (CCD) technology. The distance sensor may be infrared, acoustic or other operative technology known to those of skill in the art of proximity and distance measurement. The sensor 216 continuously senses its distance from the patient and will block the activation and discharge of radiation if the X-ray tube is too close, for example, if less than 19 centimeters directly from a patient. In addition, the system can include any number of auditory, visual, or tactile indicators to allow a physician or user of the system to determine that the sensor is within an acceptable distance or ready to fire. In additional variations, the auditory, visual, and/or tactile indicators are positioned such that the operative state of the system is identifiable without the need for the user to remove his/her focus from the object being examined. In one example, a visible indicator (e.g., one or more LEDs) is positioned on the emitter, which provides clearly distinguishable feedback regarding the distance, alignment, or any other operational conditions of the system.

The handle 200 tapers to the bottom of the device, which may house high-voltage power supply 218, external charging port 220, and battery docking station 222. Upon activation of the trigger 202 in X-ray or fluoroscopic modes, high voltage from power supply 218 is fed to X-ray generation unit 230 via the high voltage connector assembly 228. Power produced by power supply 218 is converted to a suitable input voltage that can be used by the X-ray generation unit 230. This power ranges from 1 kV to 120 kV but typically ranges between 30 kV to 90 kV in conjunction with clinical application.

The X-ray generation unit 230 is based upon existing high-voltage emitters, though custom-designed for small size required of the instant application. A suitable thickness of electrically insulating material surrounds the high voltage power supply 218, connector assembly 228 and the X-ray generation unit 230 to prevent radiation loss and preserve good beam quality. All three components 218, 228, 230 are placed immediately adjacent to each other to minimize high voltage leakage and possible interference with low voltage components in the system. In an alternative embodiment, components 218, 228, 230 may be disposed in an external control unit (not shown).

A suitable layered combination of silicone rubber and epoxy encapsulates the X-ray generation unit 230 (except where X-rays are emitted into collimator) in order to shield radiation losses and dissipate high temperatures generated by X-ray tube operation. Radiation is produced by the X-ray tube and transmitted via the collimating cone 210 at the head of the device. Fluoroscopic settings include peak kilovoltage (kV), amperage (mA), and digital brightness, are controlled by the digital control panel on the back of the neck.

The digital camera lens 212 and infrared thermal camera 214 are immediately adjacent to the collimating cone 210, and these components are also shielded by insulation. The digital camera 214 is controlled by placing the device in digital mode using the control panel. Pictures are generated via the trigger 202 located on the device handle.

Similarly, the infrared thermal camera 214 is controlled by placing the device in infrared mode using the control panel. Live infrared thermal imaging is generated by holding the trigger down. Digital X-rays, traditional digital visible and thermal images may be transferred and displayed on the external screen 112 shown in FIG. 1. Depending upon the level of cooperation between the emitter and the detector described herein, X-ray images may be transferred directly to the external monitor for viewing. A memory 233 may be used to store any type of gathered image, and such images may be encrypted upon capture in accordance with co-pending U.S. patent application Ser. No. 15/466,216, the entire content of which is incorporated herein by reference. An audio pickup 235 may be provided for procedure memorialization or other purposes, and the recordings may also be stored in memory 233, optionally in encrypted form as well.

The device is powered by an external plugin power supply with external charging port 220. The digital display, control interfaces, and trigger are controlled via the control system microprocessor electronic control unit 232 powered by a low voltage power amplifier system 234. The low voltage amplifying system 234 and the microprocessor control system 232 are also conveniently located away from the high voltage power supply to further minimize interference.

The following Table lists the various control modes associated with the emitter using the buttons and toggle switch on the control panel of FIG. 3:

| | Mode | | |
| Control | X-Ray | Digital | Thermal |
| --- | --- | --- | --- |
| Center (206) | Switch to Digital | Switch to Thermal | Switch to X-Ray |
| Left Button (302) | Increate Output Power | Toggle Macro | Decrease Exposure |
| Right Button (304) | Decrease Output Power | Zoom In | Increase Exposure |

Figure 4:
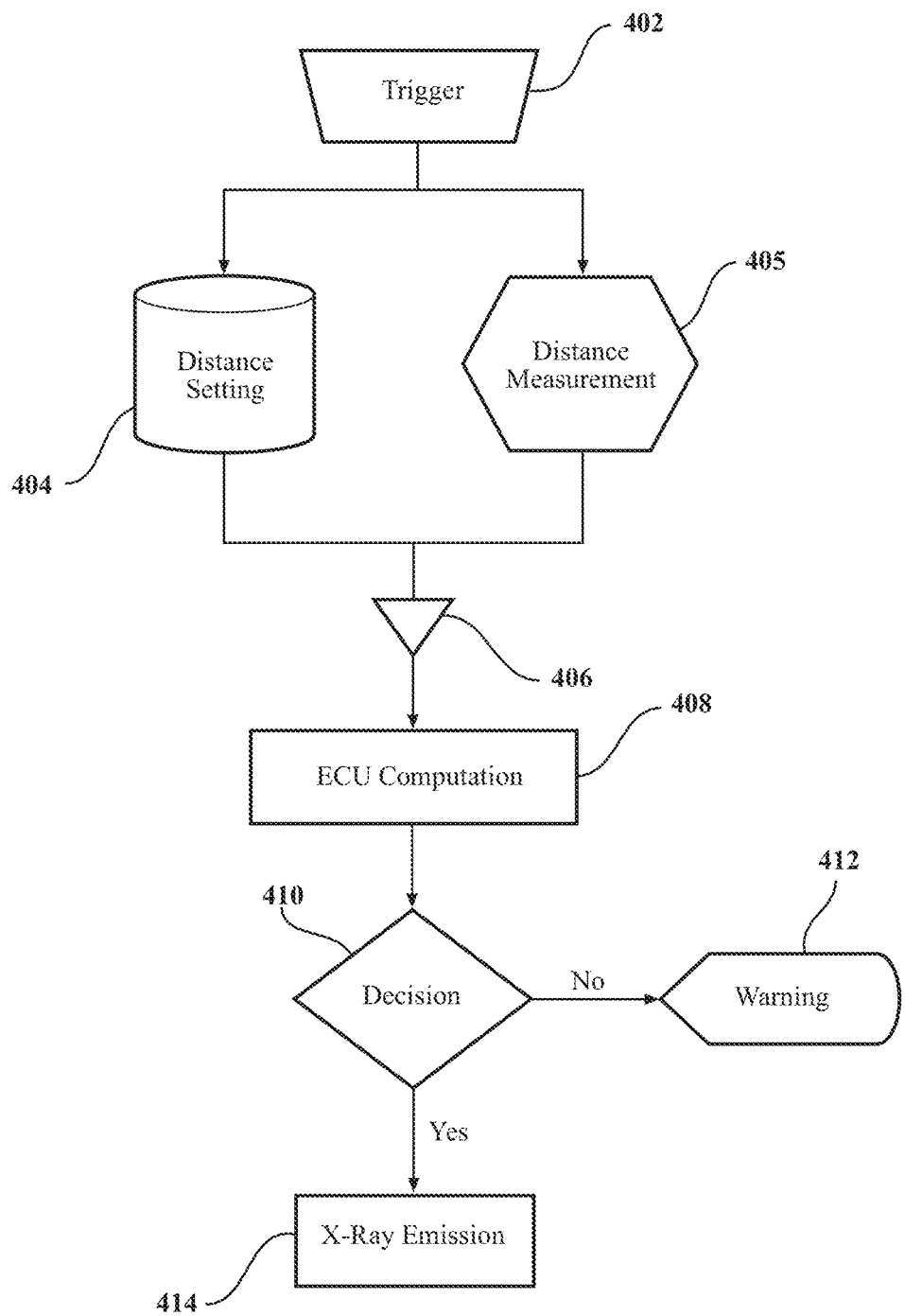
FIG. 4 shows a safety lockout procedure for an X-ray emitter.

For a variety of reasons, both practical and certification, it is important to maintain a minimum distance between the subject and the X-ray generator. This distance can change depending on a number of factors and can be configured in the emitter's software. FIG. 4 shows a process by which the device manages a safety lockout procedure of the X-ray emitter. The process to determine the safety lockout is as follows:

402. The user initiates the X-ray emission process by depressing the trigger while in X-ray mode. This could be for either a fluoroscopic or still X-ray image.

404. A distance setting is retrieved from the emitter's distance setting database.

405. The distance measurement unit is activated and captures the distance between the end of the emitter and the subject directly in front of the emitter.

406. The distance setting and distance measurements are relayed to the emitter's ECU Computation unit.

408. At 408, the ECU Computation unit uses the distance measurement, distance setting and an internal generator offset to determine if the emitter should fire.

410. The fire/warn decision at 410 is determined by the ECU and relayed to the hardware units.

412. At 412, if the ECU determines that the subject is too close to the emitter, the unit will activate a warning procedure, displaying a message on the LCD panel and activating any lockout warning lights.

414. If at 414 the ECU determines that the subject is at a safe distance, the emitter will begin the X-ray generation and emission process, signaling all internal and external components.

Due to the fact that the device can move freely in 3-dimensional space, the projected cone from the X-ray emitter varies in size based on the distance to the target. As such, the invention allows managed control over the cone size based on the distance of the X-ray emission device from a sensor positioned on the stage.

Figure 16:
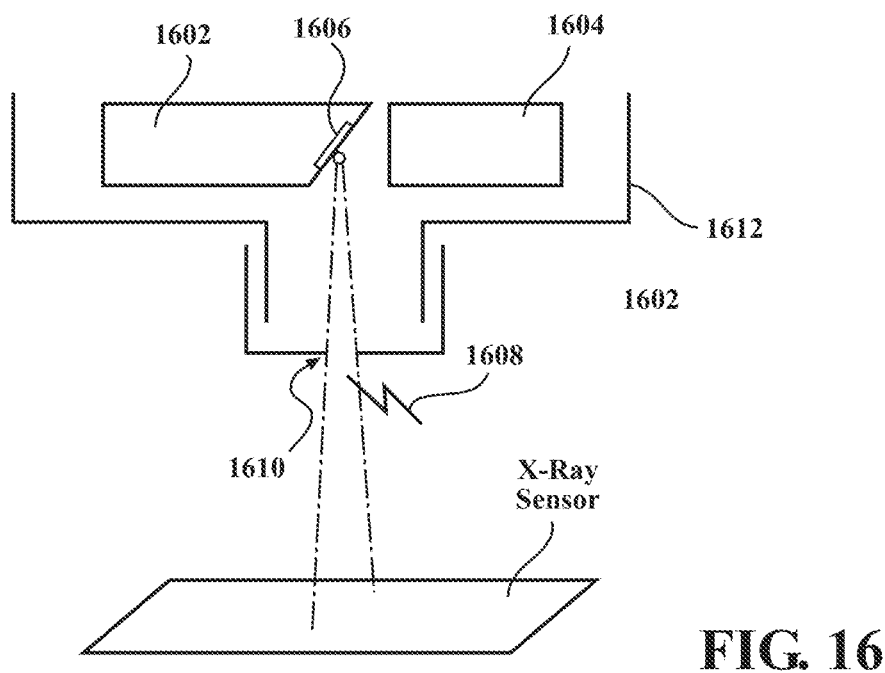
FIG. 16 is a view showing the X-ray emission device with an aperture creating the widest cone.

FIG. 16 illustrates a simplified rendition of an applicable X-ray source, which includes an anode 1602 and cathode 1604. The anode typically includes a tungsten or molybdenum target 1606. High voltage across the anode and cathode causes x rays to be produced at the target, which forms a cone 1608 that exits through an aperture 1610 in casing 1612.

Figure 17:
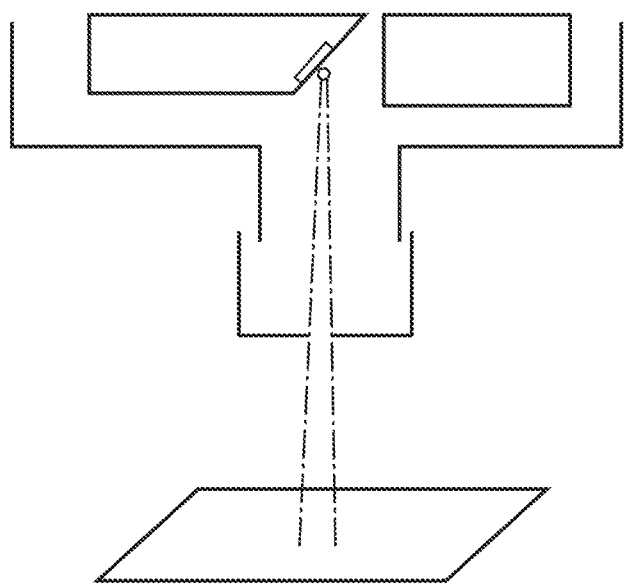
FIG. 17 shows a view showing the X-ray emission device with an aperture creating a narrow cone.

One aspect of the invention includes a telescoping chamber positioned in the direction of the aperture and sensor. The distance from the X-ray source to the output aperture can be increased or decreased by rotating the exterior chamber along a threaded interior mount. Moving the aperture closer to the source creates a wider angle, while moving it farther from the source reduces the angle, as shown in FIG. 17.

Figure 18:
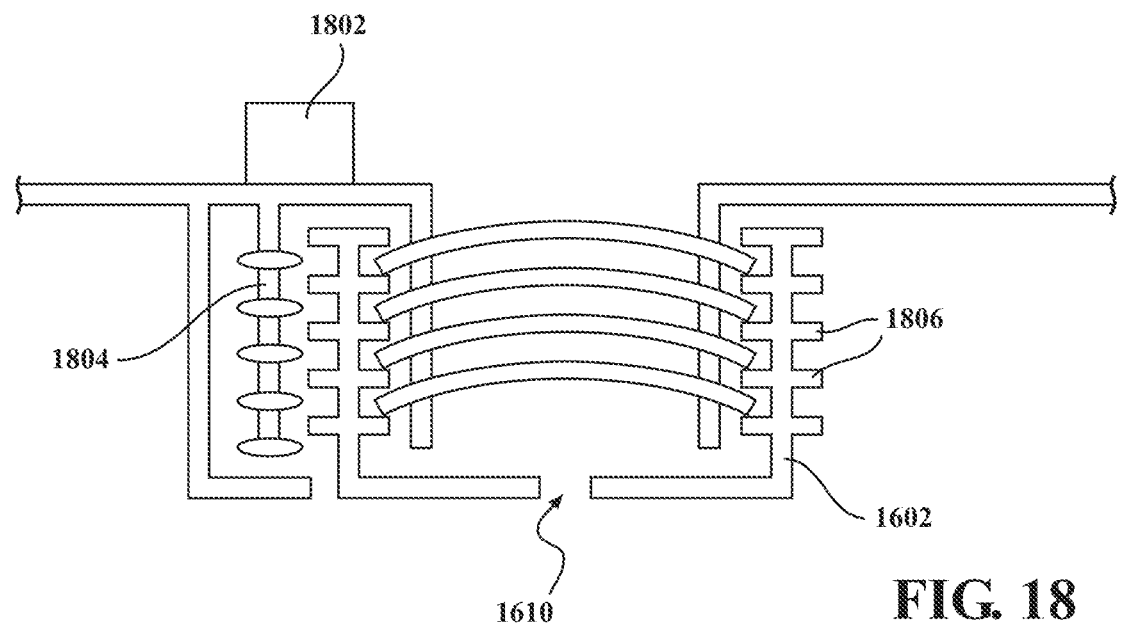
FIG. 18 shows a control unit operative to adjust the aperture and cone.

Making reference to FIG. 18, a control unit 1802 in the handheld emitter controls the telescoping aperture. Based upon the process below, the control unit 1802 rotates a threaded shaft 1804, whereupon the threads engage with grooves 1806 in telescoping chamber 1614, causing aperture 1610 to toward and away from the X-ray source.

Figure 19:
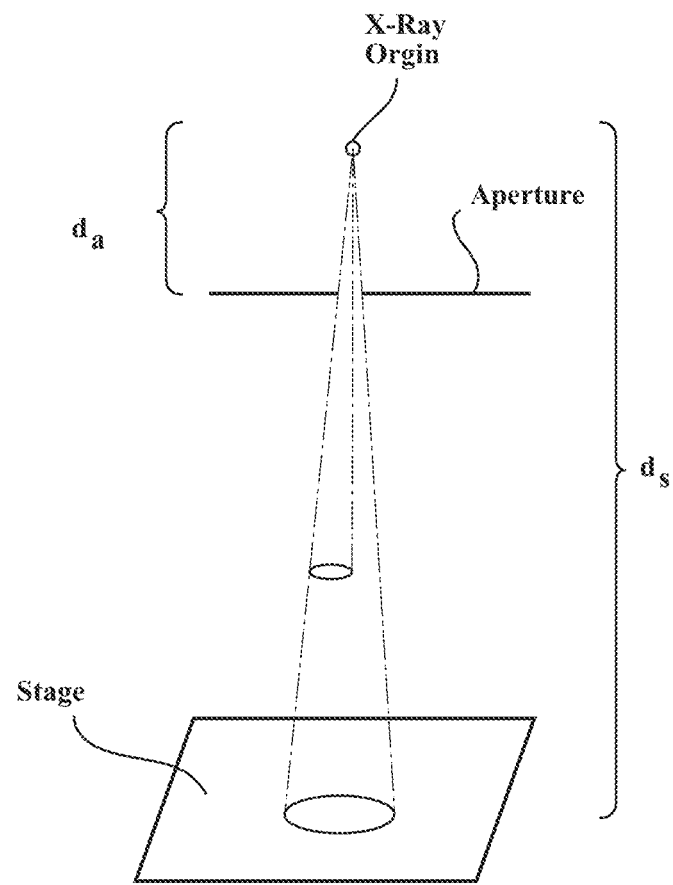
FIG. 19 is a labeled view illustrating relative distances.

FIG. 19 illustrates a control methodology. First, the distance between the device's X-ray origin and the X-ray sensor is calculated. If the distance is outside an acceptable range of X-ray emission, then no X-rays will be emitted. However, if the distance between the X-ray origin and the sensor ($d_s$) are within the acceptable range, the aperture will be automatically moved into place. The distance between the X-ray origin and the aperture ($d_a$) is then calculated, and the control unit rotates the aperture chamber to the correct distance.

If $R_s$ represents the radius of the X-ray emission as it contacts the sensor, then the angle between the normalized vector of the sensor plate and the dispersion cone can be represented as $\theta = \tan^{-1}(R_s/d_s)$. The distance that the aperture will need to be located from the emission origin to emit the correct dispersion of X-rays can be calculated as $d_a = R_a/\tan(\theta)$ where $R_a$ represents the radius of the aperture. The control unit then allows the X-ray emission device to emit an X-ray which projects a cone at an angle $\theta$ onto the sensor.

While the telescoping cone adjustment mechanism described with reference to FIGS. 16-19 is an improved aperture, those of skill in the art will appreciate that a more conventional adjustable aperture (i.e., with translatable X-ray absorbing or blocking blades) can instead be used. The same math used above is applicable to this embodiment; that is, if the distance is outside an acceptable range of X-ray emission, then no X-rays will be emitted. Conversely, if the distance between the X-ray origin and the sensor ($d_s$) are within the acceptable range, the aperture will be automatically opened or closed to facilitate firing of the source.

Different markets have different safety requirements. Additionally, depending on the subject (elderly, pediatric, otherwise healthy) the lockout may be adjusted to ensure that there are no safety issues associated with the emission. The device also preferably includes the capability to intelligently conserve power by utilizing the inertial measurement unit (IMU), distance sensor unit, as well as operator-initiated command inputs. The various durations for the power stages of the unit are user-configurable so that the device can match the user's specific style and cadence.

The systems and methods described herein can also use multiple sensors for error correction and/or to improve positioning. For example, if an emitter and detector/sensor are in a given position and the system loses tracking of one or more sensors on the platform. Ordinarily the loss in tracking might cause a reduction in the frames per second (FPS) of the output image. To address this situation, the emitter can include one or more inertial measurement units that can track movement of the emitter to adjust the intervening frame, especially when needed. The IMU will then be used to adjust the intervening frames to increase the FPS of the output. In some variations, with IMU's of sufficient accuracy, the IMU can be used in place of or in addition to sensors on the platform.

Figure 5:
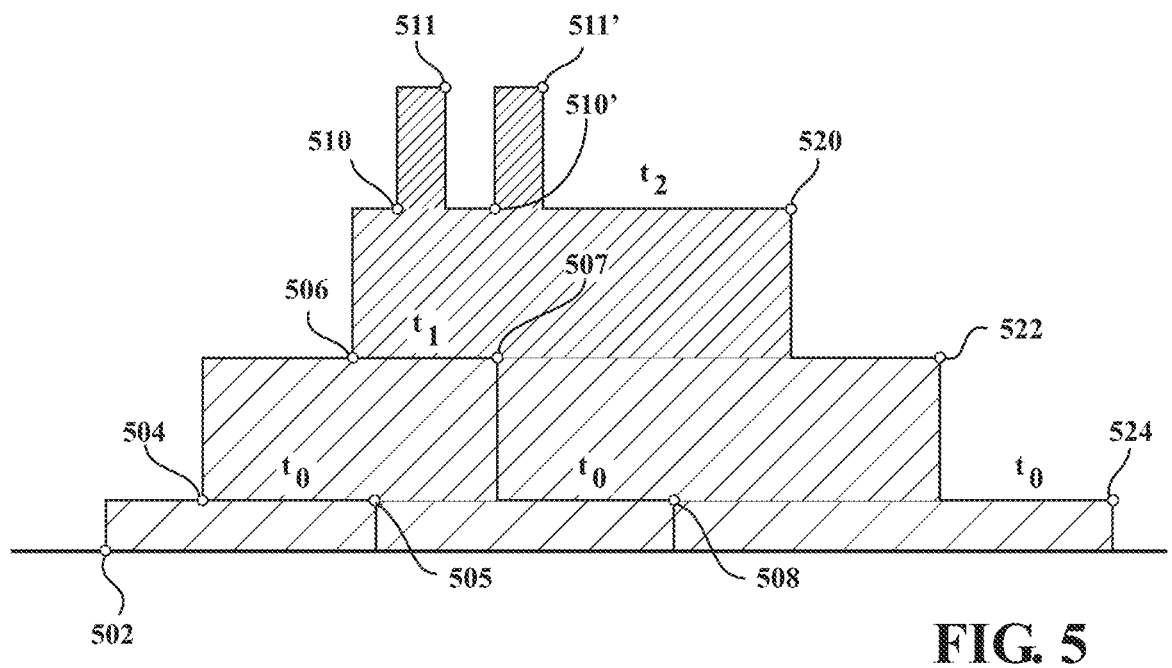
FIG. 5 depicts a representative sequence for emitter power management.

A representative sequence for power management is shown in FIG. 5.

502. The user initiates the power sequence on the device by pushing a physical button (i.e., 208 in FIG. 2) on the emitter. This engages the device's electronics and moves the device into ON mode.

504. Picking up the device is detected by the IMU in the emitter and immediately raises the power level to STANDBY. This STANDBY state initializes all power systems and raises the charge of the power supply to a medium level.

505. If the user sets the device down or is otherwise not interacted with, either through movement of the emitter or through the initiation in the control panel or control computer, the device will automatically power down to the OFF stage after a duration of t0.

506. The user has picked up the unit and has engaged the unit, either through altering of settings on the control panel itself or by bringing the device within range of a subject as detected by the onboard distance sensor. This further elevates the power level of the device by fully charging the power system to a state where the device is ready to fire, bringing the device into READY mode.

507. If, after a duration of t1 without actively engaging the unit, the emitter will power itself down to the STANDBY level.

510. The user initiates an X-ray capture by depressing the trigger 202 on the emitter. Assuming that all other safety checks are cleared, this further engages the power supply and emits the stream of X-ray photons at the subject until a state of 511, at which time the emission is complete. The user can continue to emit X-ray photons indefinitely at 510', 511', however, as the device returns to READY mode.

511. After a duration of t2 during which time the emitter has not been fired, the device will automatically power itself down to the STANDBY level at 520.

As shown with points 508, 522, 524, the device will follow the above timings to transition the device from the ON stages and finally to the OFF stage as the various durations elapse without positive engagement to maintain or change the power state. By utilizing these steps, the device can conserve power while maintaining in a ready state without any interaction from the user.

Figure 6:
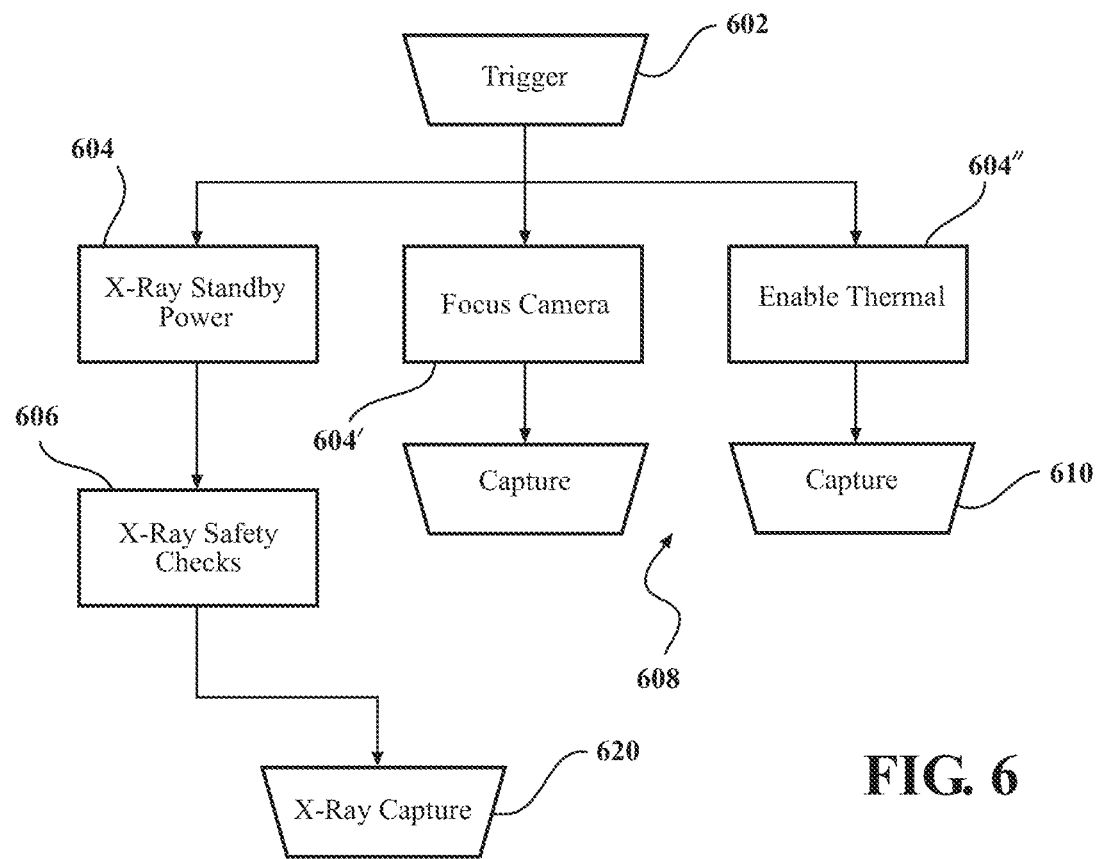
FIG. 6 illustrates a process by which a device captures concurrent images at the request of a user.

FIG. 6 illustrates a process by which the device captures concurrent images at the request of the user. Using the settings on the emitter's control screen, or by specifying a concurrent capture in the control unit, the emitter will initiate a process to capture any combination of X-ray, traditional digital and/or thermal images. The process to capture the images is as follows:

602. The user initiates the capture sequence on the device by pulling the trigger of the emitter. This begins the capture process and concurrent imaging process for whatever grouping of sensors is enabled.

604. The emitter immediately engages the X-Ray standby mode, preparing to fire the X-ray generator.

604'. Concurrently, if enabled, the traditional camera component focuses on the desired subject. This preferably occurs as soon as the trigger is depressed.

604". Concurrently, if enabled, the thermal camera is powered on and begins its start sequence. This also preferably occurs as soon as the trigger is depressed.

606. The X-ray system begins its safety checks, as illustrated in FIG. 4.

608. The digital imaging camera captures a traditional image of the subject. The image is preferably automatically transferred to the control unit for display on an external monitor.

610. The thermal camera captures a thermal image of the subject. The image is preferably automatically transferred to the control unit for display on an external monitor.

620. In one variation, after both 608 and 610 have completed, and all safety checks from 606 have been verified, the X-ray unit will fire an emission, generating an X-ray image in the sensor. The image is preferably automatically transferred to the control unit for display on an external monitor. Thus, the X-ray system will charge, verify safety, and discharge the X-ray only after all other systems have been executed to minimize operational interference.

X-Ray Detector Implementations

The emitter described herein must be used in conjunction with an X-ray detector to gather radiographic imagery. The emitter is not limited in terms of detector technology, and may be used with any available flat-panel detector, even film. However, given fully portable nature of the emitter, steps should be taken to ensure that the emitter is properly oriented with respect to the detector to gather clear imagery while avoiding spurious or unwanted X-ray emissions. One option is to mount the emitter in a fixture including a properly aligned detector plate, much like a traditional c-arm though much smaller and more capable. Another option, however, is to use the emitter with the X-ray capture stages described below, one of which includes an embedded sensor that automatically pivots, orients and aligns itself with the emitter to maximize exposure quality and safety.

One variation of an X-ray capture stage includes a statically fixed platform, positioned during the outset of surgery, with an interior cavity containing an X-ray sensor, an X-ray sensor positioning system, an emitter tracking system, a shielding system and a control unit. The X-ray capture stage is adapted to receive an X-ray emission from a separate emitter device, including the portable, handheld unit described herein. The X-ray capture stage preferably also incorporates wireless (or wired) communications capabilities enabling review of a captured X-ray or fluoroscopic image on an external display monitor or any other arrangement for the captured image including external storage.

There are broadly two capture stage embodiments. In a clinical embodiment, the stage tracks the emission and simply locks out the X-ray firing if it is not in line. A tracking stage embodiment also permits or locks out emission in accordance with alignment, but also precisely tracks the position and angle of the X-ray emission, positioning and tilting the embedded sensor to capture a precise, high-quality X-ray image. This arrangement uses less power, corrects for any skew or perspective in the emission and allows the subject to remain in place, thereby enabling the surgeon's workflow to continue uninterrupted and capture X-rays without repositioning equipment, the subject or the surgeon.

Figure 7:
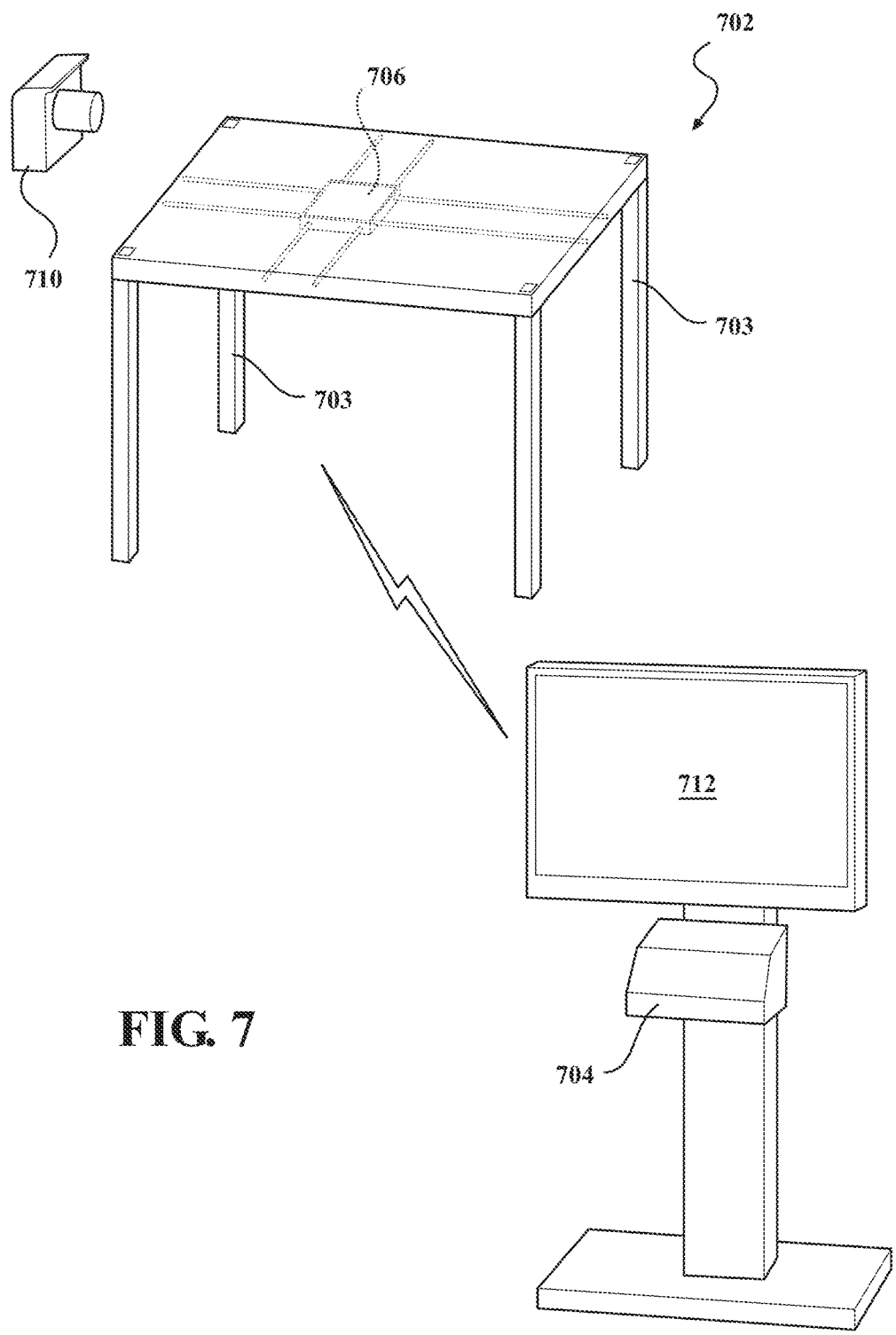
FIG. 7 is a drawing that illustrates the overall components of a variation of a capture stage.

FIG. 7 is a simplified view of a variation of the X-ray capture stage, which includes a platform 702 with a hollow cavity including the embedded sensor 706. In one configuration, the stage might have legs 703 and be used as a table. In another configuration, the stage might be wrapped in a bag and positioned underneath a patient. Thus, the platform 702 can be wrapped in a sterile drape and surgical procedures can be performed upon a platform, such as table 105 in FIG. 1.

The capture stage cooperates with a separate X-ray emission device 710. There are a number of different configurations and implementations of the X-ray emission device besides the handheld unit described in detail above, including wall-mounted, armature-mounted, and floor-mounted. Any implementation is compatible with the operative X-ray stage as long as the electronic systems of the emitter can communicate with the interface of the operative X-ray stage central control unit to provide for pivoting, orientation or alignment.

The platform 702 is in electrical communication with a central control unit 704. A display monitor 712, electronically connected to the control unit 704, which may be used to both display images and provide overall system control. Generally, a user will interact with the emitter 710; however, in some cases, a user may interact with the central control unit 704 directly to manipulate images, setup specific capture scenarios, control parameters or adjust other settings. The system may also use a tablet, mobile phone or any other display device electronically connected to the central control unit for display purposes. The central control unit 704 and display may be combined in a single device, such as a laptop computer or other mobile computing device. Optionally, the central control unit can be electronically connected to multiple display units for educational or other purposes.

Figure 8A:
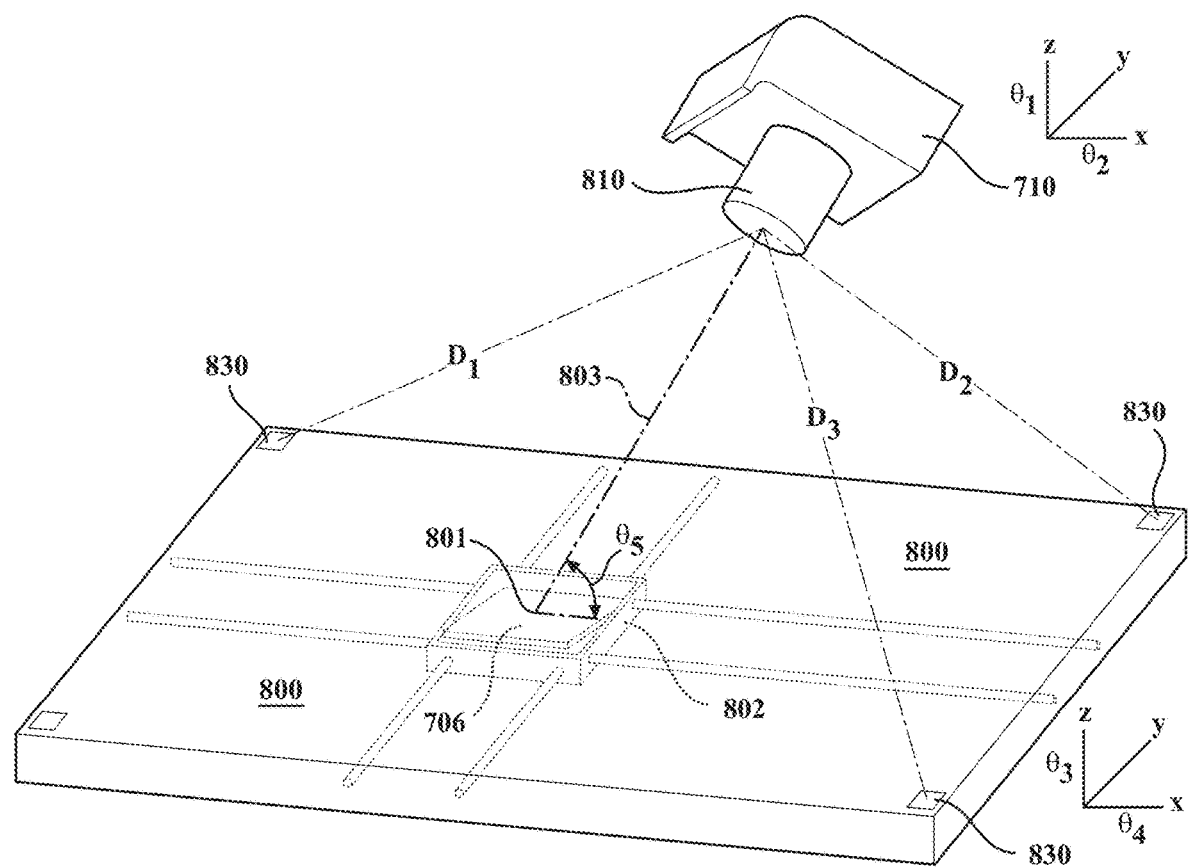
FIG. 8A is an oblique view of a sensor positioning system.

FIG. 8A is an oblique view of an X-ray capture stage according to the invention. In one specific arrangement, the stage comprises a hollow, sealed shell that is roughly 20"×30", although the overall size of the invention can be changed to conform to other surgical applications. The shell creates a cavity 800 housing an X-ray detection sensor 706 operative to capture an X-ray emission from an X-ray emitter. Suitable X-ray sensors are available from a variety of commercial manufacturers. The sensor 706 is attached to a motorized movement system used to pan and tilt the sensor within the cavity. This motorized system ensures that the sensor is precisely positioned for maximum image quality and capture view.

Figure 9:
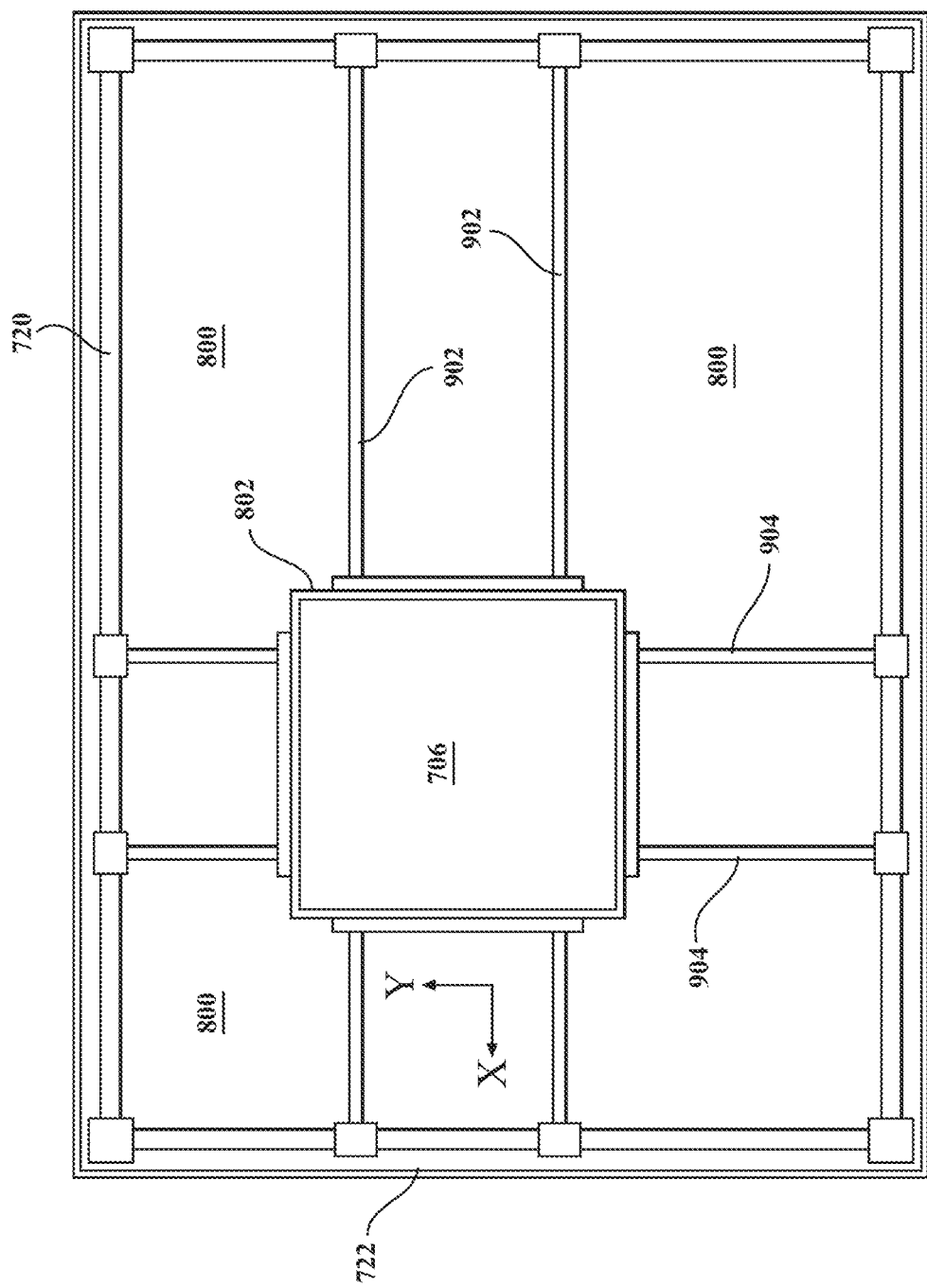
FIG. 9 is a diagram that shows x, y movement of a sensor tray viewed from above.
Figure 10A:
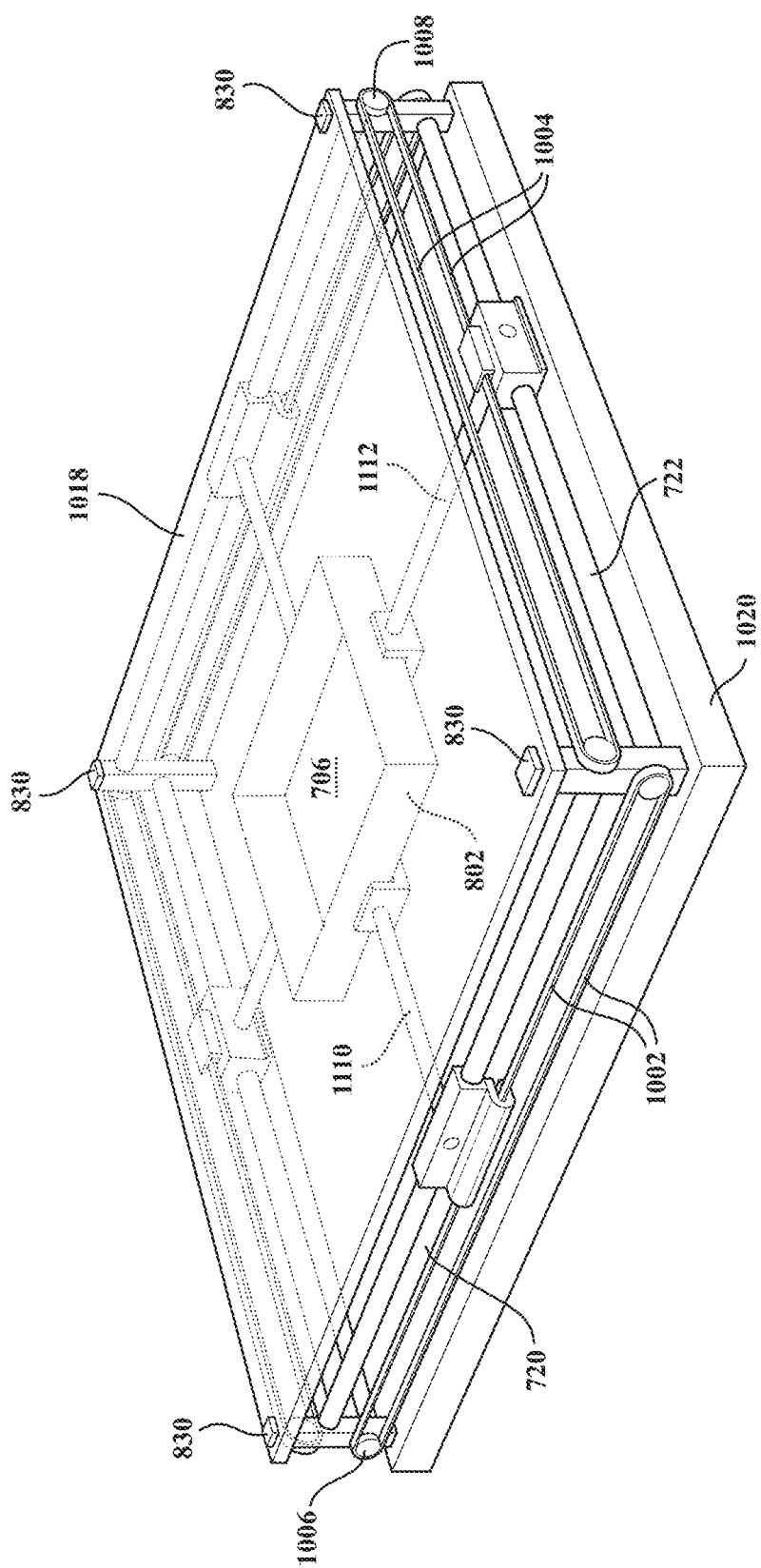
FIG. 10A is an oblique diagram showing a band-operated image capture stage.

The X-ray sensor 706 is preferably mounted to a movable tray 802 that travels under controlled movement within the cavity 800. The tray and sensor can move in the x-y direction and tilt along both axes as described below. FIG. 9 is a diagram of a capture stage seen from above. The sensor 706 in tray 802 is mounted to translate on a series of motorized rails 720, 722, allowing the sensor to position itself anywhere along the x and y axis within the shell. At least one of the x and y tracks may be a threaded rod, for example, each being driven by a motor for precise lateral movement of the tray 802 in the x and y dimensions. As a further alternative, the x-y movement of the tray may be controlled with bands 1002, 1004 in FIG. 10A. Such bands are precisely controlled by rods 1006, 1008, causing tray supports 1110, 1112 to translate tray 808. Note that while four tray supports 902, 904 are depicted in FIG. 9, single supports 1110, 1112 may alternatively be used as shown in FIG. 10A.

The emitters 830 are used to measure the distance from a point 810 on the handheld unit 710 to three (or more) fixed points 830 on the stage. These distances are depicted as $D_1$, $D_2$ and $D_3$ in FIG. 8A. Based upon these distances, the system employs a tracking method to precisely locate a center point 801 on the sensor 706 and angle ($\theta_5$) of the emission from the source to the platform. An exemplary implementation of this tracking system would include a combination of infrared sensors within the platform and the handheld unit, as well as a gyroscope in the stage and handheld unit to detect the angle $\theta_5$.

The positioning of the detector uses a number of sensors in concert. When the user picks up the handheld unit, the system enters a ready state. The infrared beacons on the corners of the table illuminate. The positioning tracking camera on the handheld unit immediately starts analyzing the infrared spectrum captured within a 140-degree field of view. The camera is searching for patterns of infrared light.

Each corner 830 has a specific pattern that determines which corner of the stage the infrared camera in the handheld unit is looking at.

Figure 8B:
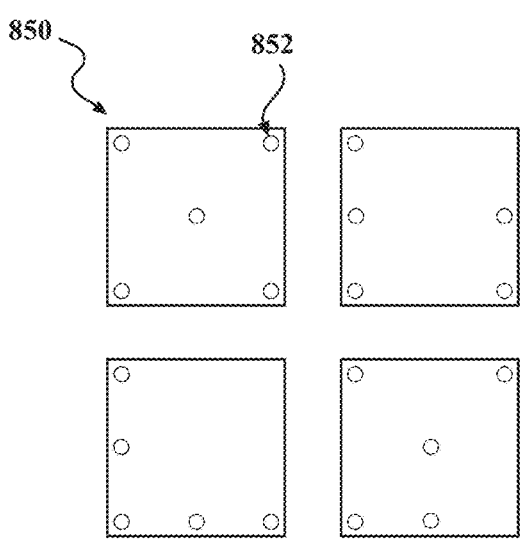
FIG. 8B illustrates infrared (IR) positioning tiles.

Making reference to FIG. 8B, an IR positioning emitter tile 850 sits at each corner of the operative or clinical stage. The diagram is an example of four unique tiles. When using the mounted positioning beacons, the pattern will be different. These tiles contain a number of infrared emitters 852, usually five individual emitters, arranged in a specific pattern. Each tile contains a different pattern of the five IR emitters. As the operator moves the X-ray emitter around the stage, the IR positioning camera captures and analyses the IR emissions from the tiles. Because each tile has a unique pattern, the camera is able to determine its exact position in relation to the table. Additionally, because each tile has a unique pattern of multiple lights, the system can determine the exact position from the tile in XYZ space.

Optionally, or in addition to this unique IR layout, the IR emitters can flash in a syncopated manner. By modulating the frequency of the flashes, it is possible to add an additional uniqueness signature to each tile, allowing patterns to repeat in a scenario with a large number of tiles. Because of this unique arrangement, only a single corner of the unit, or single positioning beacon, needs to be visible to the emitter to allow the system to fully function. That is, due to the layout of the pattern, the camera can triangulate its position in space relative to each corner. By using the triangulation data, as well as the orientation data from the IMU unit on the emitter, the system can determine the center point of the emission. The stage will then move the center point to that area of the stage and tilt the detector to be as perpendicular to the emission as possible. While the sensor is moving into position, the collimator on the emitter adjusts the output of the beam to ensure that it is illuminating the detector panel only.

The position information from the combination of the sensors 830 is routed through the control unit (i.e., 704 in FIG. 7), which interpolates the raw sensor data into an aim point on the platform. The platform then moves the sensor tray 802 to the specified point. The platform then tilts the sensor into the correct orientation ($\theta_5$) to remove as much skew as possible. Stated differently, assuming the X-ray source in emitter 710 emits radiation with respect to an axis 803, the goal is to place the axis 803 as close as possible to the center point 801 of the sensor, with the plane of the sensor being as perpendicular as possible to the axis 201 to minimize skew.

In all stage embodiments, the upper cover of the platform or shell is covered with a radiolucent material (i.e., 1018 in FIG. 10A). However, the lower base of the platform (i.e., 1020 in FIG. 10A) is preferably coated with an X-ray absorbing material such as lead. This coating prevents the excess X-rays from penetrating through the field and being absorbed by the operator of the emitter. This X-ray absorbing undercoating also prevents excess X-ray emission from bouncing off the floor and scattering throughout the facility. The sides of the platform may be constructed from a radio-opaque material as well.

Figure 10B:
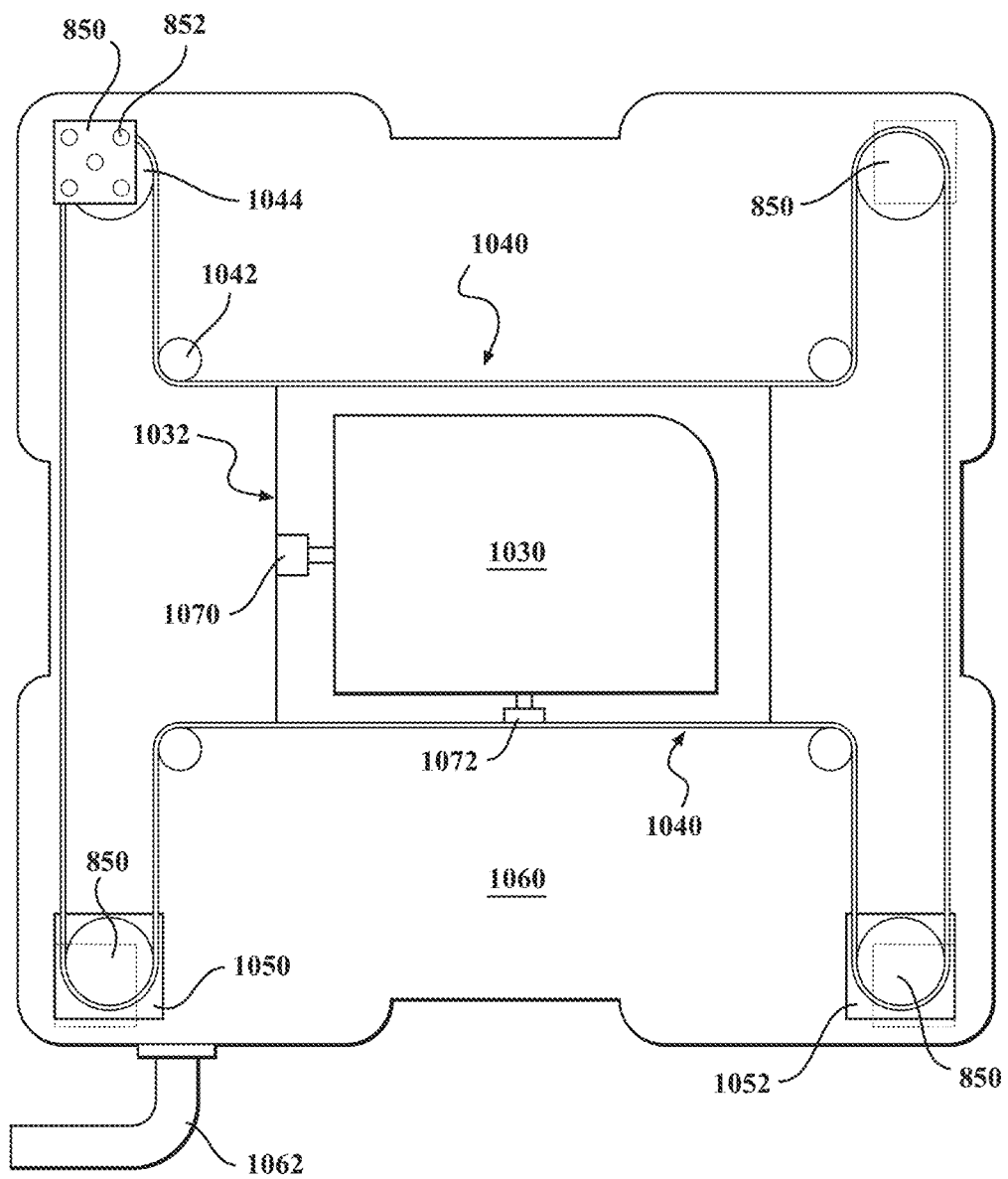
FIG. 10B is a schematic diagram of a band-operated stage with an identification of important components.

FIG. 10B is a schematic diagram of a band-operated stage with an identification of important components. The X-ray detector is shown at 1030, and the detector carrier is depicted at 1032. This particular embodiment is driven by an H-shaped belt 1040. Items 1042 and 1044 are small and large offset bearings, respectively. The belt is driven by motors 1050, 1052. The stage housing is shown at 1060, and power is brought in via cable 1062. The detector tilt motors are indicated at 1070, 1072. IR positioning tiles and IR emitters described with reference to FIG. 8B, are shown at 850 and 852, respectively. The typical IR emitters described herein are active beacons since they actively emit a signal or energy that is received by the emitter to aid in determining a position of the emitter. Alternatively, or in combination, additional variations of the methods, systems, and devices described herein can include passive markings or objects to aid in determining orientation of the emitter. The systems, devices and method can include camera or emitter that simply record a specific pattern (e.g., a QR symbol or some unique object in the surgical area such as a clock, table, fixture, etc.). The system will then rely on a computer to use these patterns in place of, or in combination with, IR beacons to determine a position of the emitter. In this latter case, the emitter position is calculated by the computer or other processing unit.

Figure 11A:
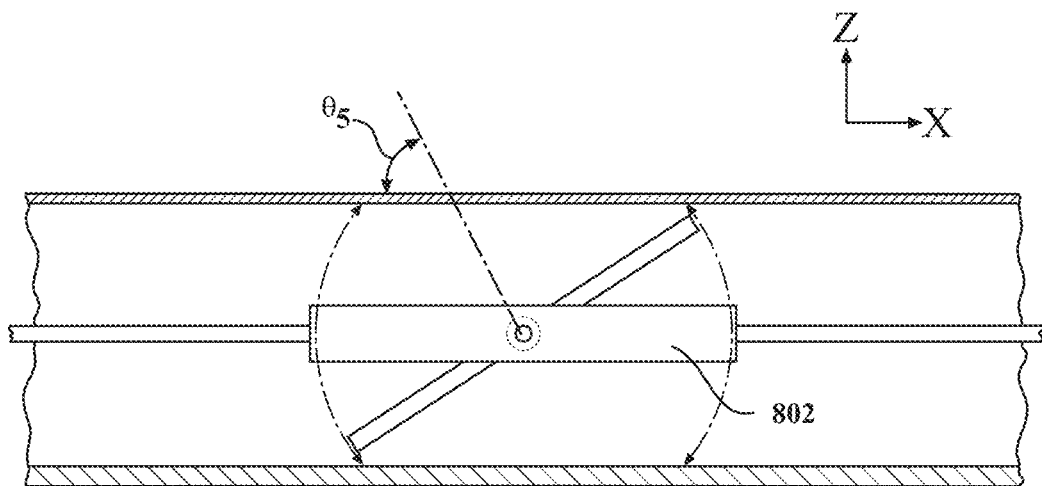
FIG. 11A is a side view showing a sensor tilt operation.
Figure 11B:
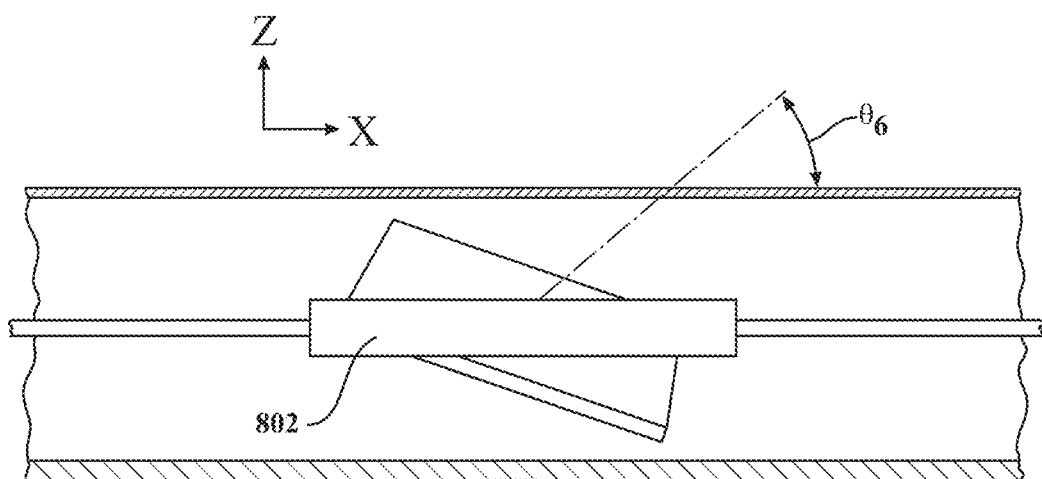
FIG. 11B is a side view showing a sensor panning operation.

FIGS. 11A, 11B are diagrams that show a pan and tilt mechanism. In FIG. 11A, the sensor tray 802 is positioned within the cavity and the sensor 706 is tilted around the y-axis. In FIG. 11B, the sensor tray 802 is tilted along both the x-axis and the y-axes. This panning and tilting allow the sensor to be precisely positioned to capture an X-ray image while minimizing the distortion created by the offset angle of the emission device. That is, the capture stage and X-ray emitter are coordinated to minimize skew and maximize capture of both X-ray and fluoroscopic images. By moving the sensor within the stage, the user does not need to reposition the subject to get a clear, usable X-ray or fluoroscopic image.

In the case of a handheld emitter, wherein the emission device is physically decoupled from the stage, it is important to position the sensor relative to the emitter for quality and safety reasons. Different techniques may be used to accomplish this goal. As shown in FIGS. 8 and 10, a plurality of position tracking implements 830 may be mounted to the ends or corners of the tray. While these implements may be used in all four corners, only one is necessary for accurate triangulation. These implements may be based upon ultrasonic tone generation or infrared emission. In these embodiments, acoustic or infrared signals generated in the platform are detected by the emitter device, causing the sensor to translate and tilt to maximize capture. A further embodiment may utilize magnetic position and orientation sensors and detectors of the type used in surgical navigation to orient the tray and X-ray sensor.

Figure 12A:
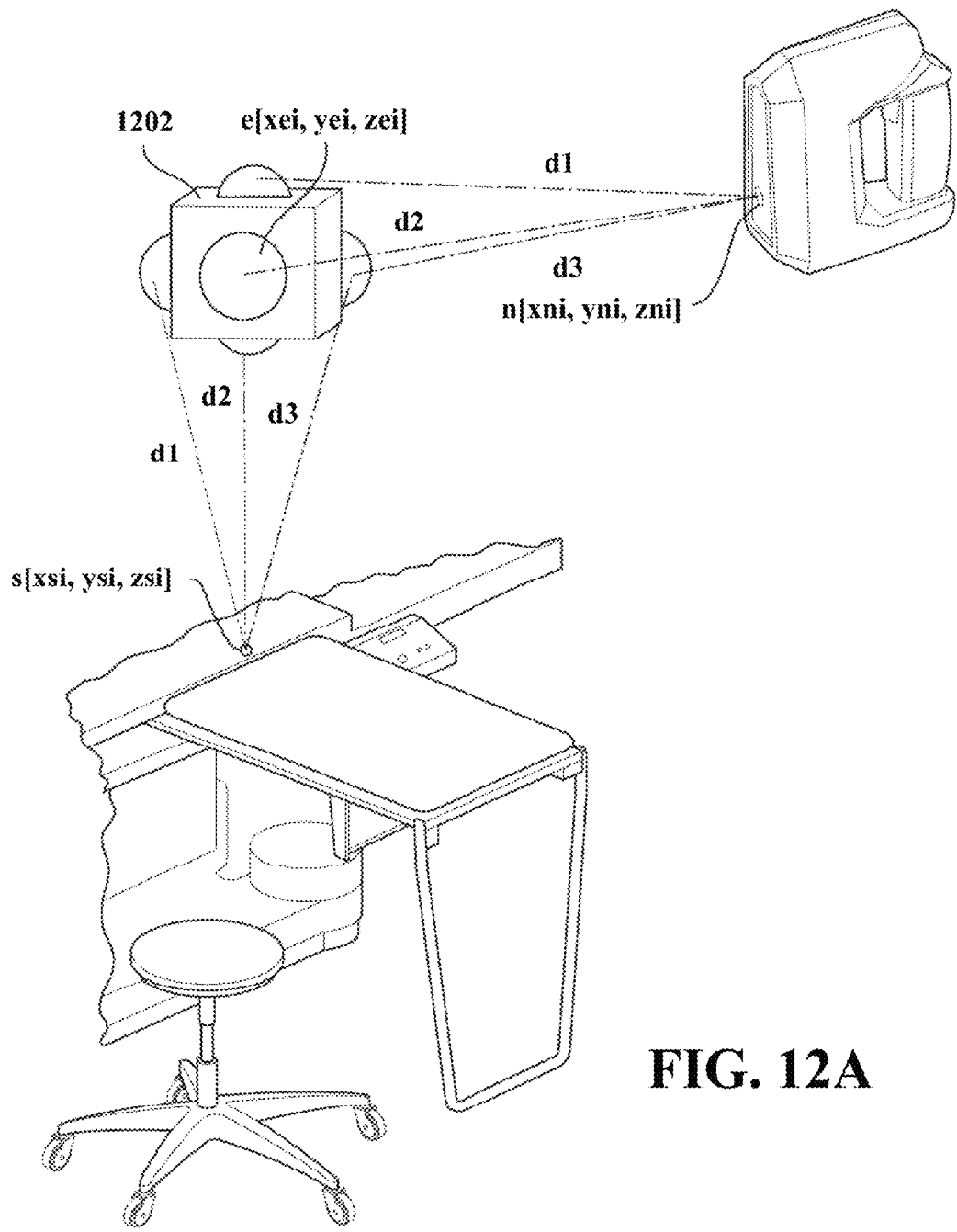
FIG. 12A illustrates an arrangement whereby an emitter need not be provided on an image stage platform.
Figure 13:
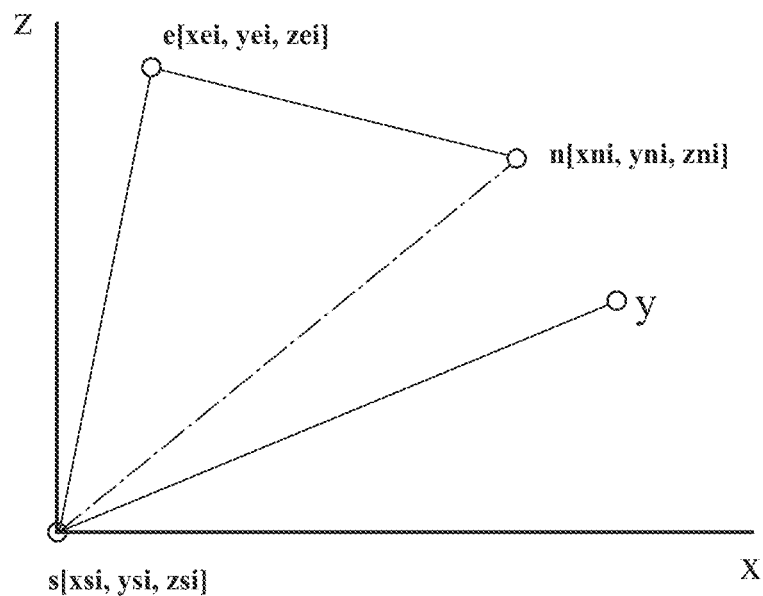
FIG. 13 is a view of an infrared emission device emitting infrared from 5 points allowing for relative position calculation in 3-dimensional space.

The x, y, pan and tilt positioning of the tray and sensor may be accomplished without position emitters in the platform portion of the system. FIGS. 12A and 13 illustrate an alternative system and method of position calculation that removes the dependency of having position emitters embedded in the table. Instead, the position of the X-ray emitter in relation to the capture stage and X-ray detection sensor can be calculated based on external position emitters. As noted above, the emitter can be purely handheld to allow a practitioner to move the emitter in free space. Alternatively, the emitter can be moveable with (or coupleable to) a support structure that maintains the emitter in position relative to the object without requiring the physician to continuously hold the emitter.

The process to determine the location of the X-ray emission device in accordance with this embodiment is as follows:

The external positional emission device(s) are installed onto a fixed location and contain a series of infrared emitters. This emission device releases infrared patterns from 5 sides of a cubic object 1202 resulting in infrared energy being sent out from slightly different origins.

The stage detects the infrared pattern and calculates the relative position from the stage to the center of each infrared emitter in 3-dimensional space. This position will be considered [xsi, ysi, zsi]=[−xei, −yei, −zei] with s representing the stage, e representing the infrared emission device, and i representing the index of the infrared emission device (if leveraging multiple infrared emitters).

The X-ray emission device continually detects the infrared signal patterns and determines the relative location of the emission device to the center of each infrared emitter in space. This relative position is relayed to an emission position control unit for each emitter. This position may be considered [xhi, yhi, zhi]=[−xei, −yei, −zei], with h representing the X-ray emission device, e representing the infrared emission device, and i representing the index of the infrared emission device.

The emission position control unit will receive the relative positions of the X-ray emission device ([xhi, yhi, zhi]). Using these relative positions, the emission position control unit calculates the position of the X-ray emission device relative to the stage (FIG. 13), resulting in [xhi-xsi, yhi-ysi, zhi-zsi]. This operation is performed for each infrared emission device (i), which can then be used to deduce the margin of error.

After the stage applies the position along with the other pieces of data as mentioned in the original filing, the stage moves and rotates the X-ray sensor plate into the correct position to capture the X-ray image.

Figure 12B:
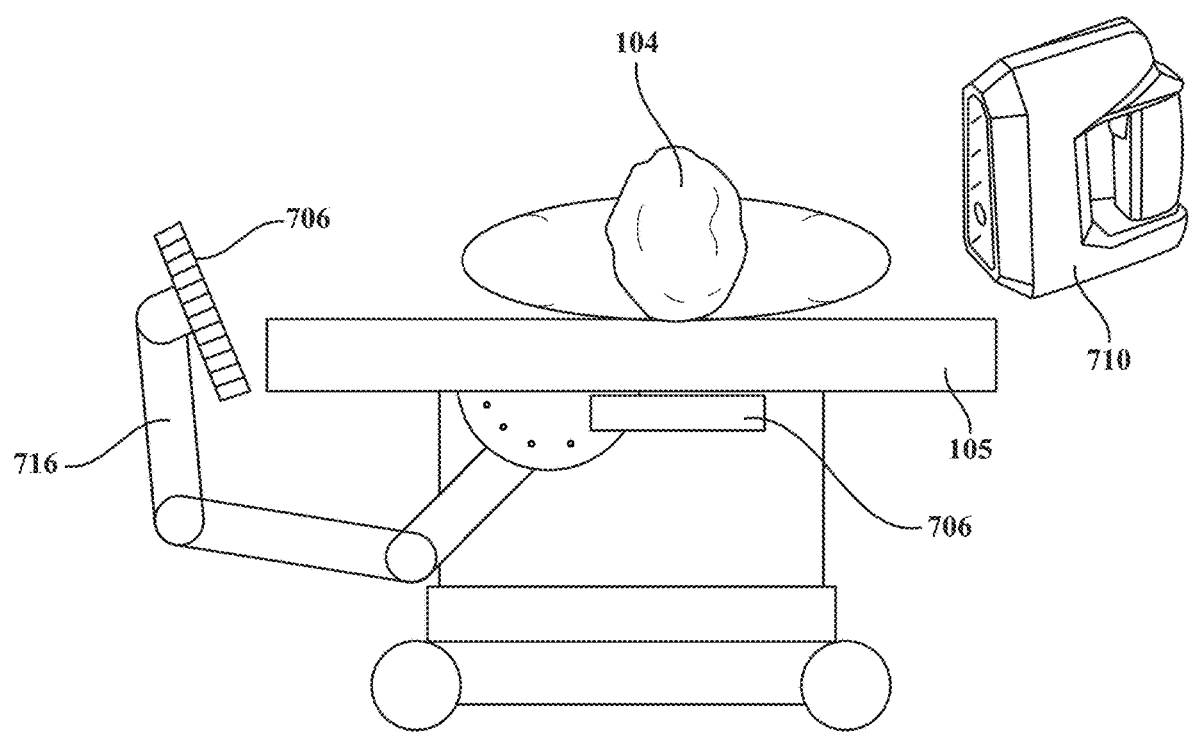
FIG. 12B illustrates additional arrangements of the imaging system where a sensor can be configured to capture lateral views by moving above a plane of the table.

FIG. 12B illustrates a variation where an emitter 710 can apply energy to a sensor/detector 706 that is configured to move as discussed herein but can also move to enable a lateral image. In the illustrated variation, the sensor/detector 706 moves outside of the center X axis of the table 105 to capture lateral views of the patient 104. However, variations of the sensor 706 can include configurations where the table is non-planar and is configured to receive the sensor 706 above a plan in which the patient is positioned. FIG. 12B also illustrates an additional concept where multiple detectors 706 are used as described herein. In such a variation, the sensors 706 would be moved as described herein, but the sensor having the best operational alignment would be used to generate a signal.

Safety Lockout Procedures

Figure 14:
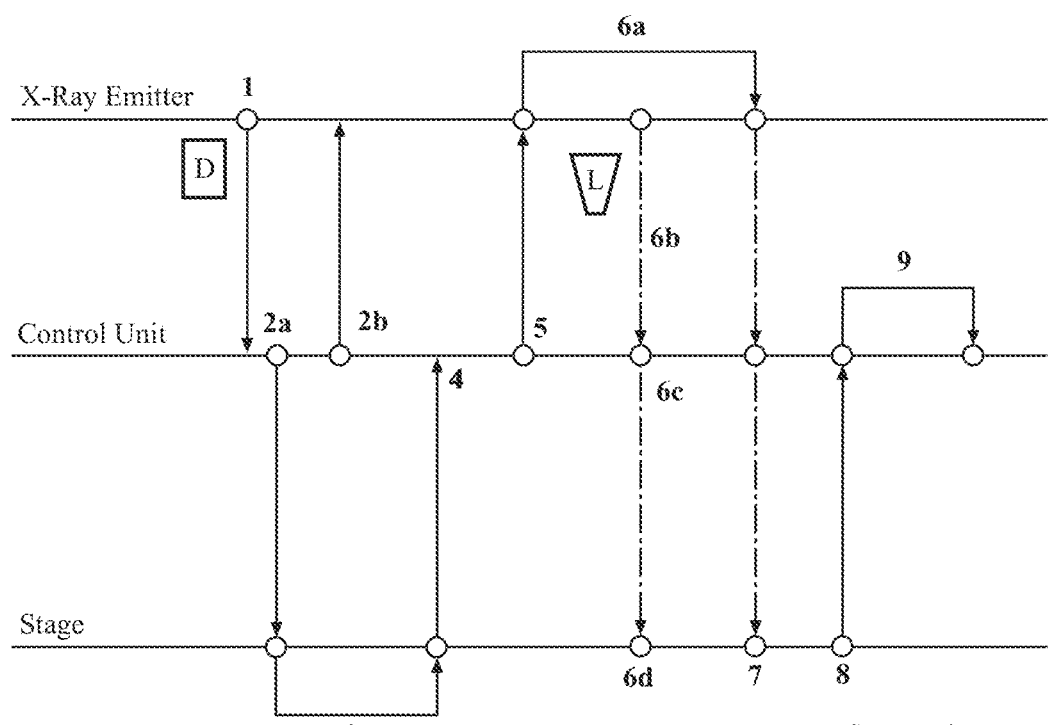
FIG. 14 illustrates a safety lockout of the capture stage based upon the disposition of the emitter.

Just as it is important to limit emissions from the emitter to specific target distances, for a variety of reasons, both practical and certification, it is important to only fire the X-ray generator when the emitter is properly aimed at the capture stage. By preventing the X-ray generator from emitting photons while not pointed at the stage, the safety of the system is improved and the performance of an emitter is increased. FIG. 14 illustrates the process by which the device manages the safety lockout of the emitter and captures an X-ray image, with the numbers corresponding to the numbers in FIG. 14:

1. User initiates the capture process by signaling through the emission device 110, typically by depressing a trigger. The emitter sends a data packet (D) to the controller containing the request for capture, the distance measurements (d1, d2, . . . ) and the angle of the emitter.

2a. The controller validates that the emitter is in a safe orientation.

2b. If the controller discovers that the emitter is not in a safe, valid orientation, the controller sends an error message to the emitter. This prevents the emitter from firing and signals to the user that there is a problem.

3. The stage positions the sensor in accordance with the position of the emitter. The stage will tilt the sensor so that it is in the correct orientation to capture a clear image. The orientation will be as close to the complementary angle of the emission as possible.

4. The stage then sends a confirmation message to the controller after the position has been established.

5. The controller forwards the start message to the emitter. The emitter will then execute any additional safety or preparation tasks. If the emitter believes the environment is safe to fire, the emitter will then fire the X-ray.

6a. The emitter fires a pulse of X-ray photons at the stage for the requested amount of time.

6b. During the emission of the X-ray photon stream, the emitter constantly streams any updates to the position and angle to the central controller.

6c. The controller records these positional updates and relays them to the stage.

6d. The stage will rapidly and constantly update the position and angle of the sensor to optically stabilize the X-ray image.

7. The sensor captures the emission of X-ray photons from the emitter and builds an image.

8. Upon completion of the X-ray emission, the sensor relays the data to the control unit.

9. The control unit then cleans up the image from the sensor using a variety of known optical enhancement techniques. If applicable, the control unit will leverage the stored movement data from the emitter to further enhance the output.

The above process allows the emitter to ensure that the emission will be directed at the sensor and the stage as opposed to any other arbitrary target. By moving the sensor into place below the emission target, the user can create a resolute, flexible image of the exact desired portion of the subject without having to reposition the subject.

Figure 15:
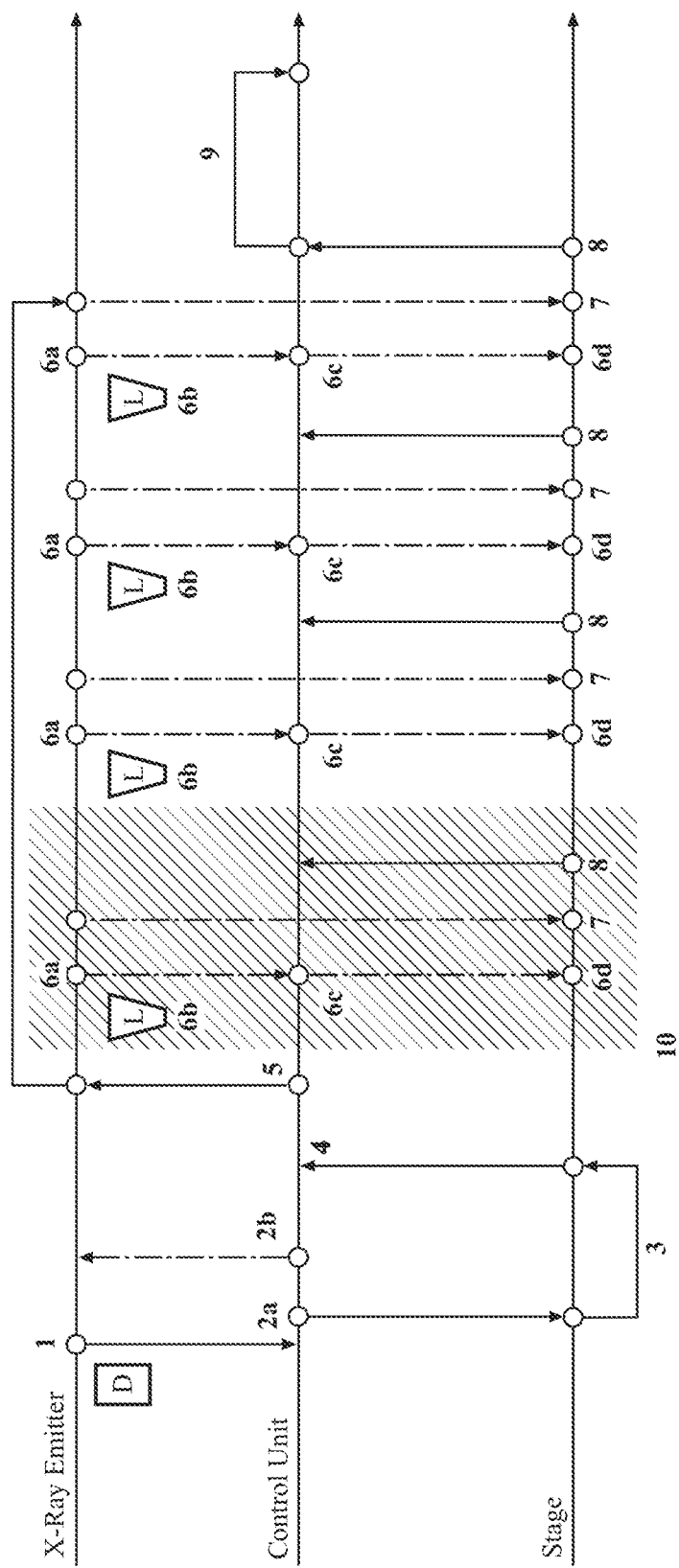
FIG. 15 illustrates the capture of a fluoroscopic image.

FIG. 15 illustrates the process by which the device captures a fluoroscopic image. The process for capturing a fluoroscopic image is very similar to capturing a static X-ray image; however, the fluoroscopic process will repeat several emissions and image captures to create a moving image. The process to ensure the safe emission as well as capture the fluoroscopic image, with the numbers corresponding to the numbers in FIG. 15:

1. User initiates the capture process by signaling through the emission handle, usually by depressing a trigger. The emitter sends a data packet (D) to the controller containing the request for capture, the distance measurements (d1, d2, . . . ) and the angle of the emitter.

2a. The Controller validates that the emitter is in a safe orientation.

2b. If the Controller discovers that the emitter is not in a safe, valid orientation, the controller sends an error message to the emitter. This prevents the emitter from firing and signals the user that there is a problem.

3. The stage positions the sensor in accordance with the position of the emitter. The stage will tilt the sensor so that it is in the correct orientation to capture a clear image. The orientation will be as close to the complementary angle of the emission as possible.

4. The stage then sends a confirmation message to the controller after the positioning.

5. The controller forwards the start message to the emitter. The emitter will then execute any additional safety or preparation tasks.

In the fluoroscopic mode, the emitter will repeat the following steps while the emitter device continues to request additional fluoroscopic frames, as follows:

6a. The emitter fires a pulse of X-ray photons at the stage for the requested amount of time.

6b. During the emission of the X-ray photon stream, the emitter constantly streams any updates to the position and angle to the central controller. If at any time during the fluoroscopic process, the operative stage detects the emission is not aimed at the stage, the stage will send a termination signal to the emission device and skip directly to step 9.

6c. The controller records these positional updates and relays them to the stage.

6d. The stage rapidly and continuously updates the position and angle of the sensor to optically stabilize the X-ray image.

7. The sensor captures the emission of X-ray photons from the emitter and builds an image.

8. The sensor immediately transfers the image to the control unit. At this time, a brief cleanup process is executed and the image is displayed on the external viewing device. This fluoroscopic frame is saved to memory.

The constant repetition of this process creates a moving image on the external display. The process will repeat until the user releases the trigger of the emission device.

9. Once the user releases the trigger of the emission device, the control unit "cleans up" the stored frames from the sensor using a variety of known enhancement techniques. If applicable, the control unit will also apply any stored movement data from the emitter to further enhance the output. The control unit will then combine the fluoroscopic frames into a single video for repeated playback.

The above process allows the user to see a live fluoroscopic view of the subject in real-time. By storing the images and reprocessing after the capture is complete, the device can create a high-quality, single fluoroscopic video for display and review at a later time.

Self-Adjusting Collimator

As noted above, the systems of the present disclosure allow for moving an emitting apparatus to a location relative to the object and determine a position of the emitting apparatus relative to at least one position tracking element where the at least one position tracking element measures a distance between the emitting apparatus and the object and preventing emitting energy until the distance is less than a pre-determined distance. Variations of the systems described herein can use a self-adjusting collimator that optimizes a profile or boundary of the emission onto the working surface of a sensor. As with other variations described herein, these systems can relay the position of the emitting apparatus to a motor system that adjusts an imaging sensor into an operative alignment with the emitting apparatus, where relaying the position of the emitting apparatus includes using the emitting apparatus to both provide an orientation data of the emitting apparatus and determine a distance from each of the plurality of tracking elements. However, the use of a self-adjusting collimator allows for automatic maximization of an emission profile on the imaging sensor.

Figure 20:
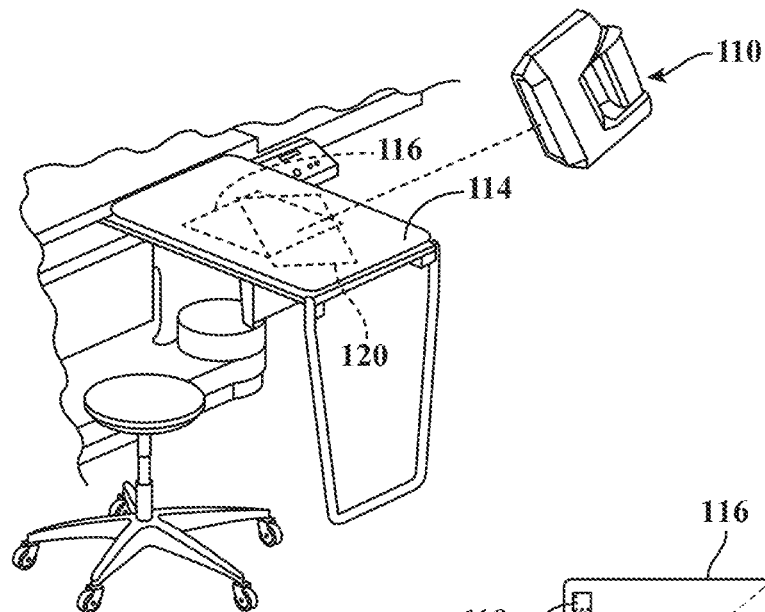
FIG. 20 illustrates a situation where an emitting apparatus casts an energy profile that exceeds a profile of an imaging sensor.

To illustrate the benefit of an adjustable collimator, FIG. 20 illustrates a representation of an X-ray emitter 110 directed towards a table 114 having an imaging sensor (not shown) located therein. The perimeter of the working area 116 of the imaging sensor is shown to illustrate the area that will produce an image upon exposure to an X-ray emission. As shown, a profile of an X-ray emission 120 from X-ray emitter 110 extends beyond the perimeter of the working area 116 of the imaging sensor causing the X-ray emitter to be out of operative alignment with the sensor. In such a case, the system as described herein will not permit firing or initializing of the X-ray emitter 110. The illustration of FIG. 20 is intended to illustrate a concept of the system being out of operative alignment. As noted herein, the imaging sensor can be coupled to a motor system to permit movement of the sensor into alignment with the emission profile 120. Alternatively, the table (or operating surface) 114 can include a plurality of position tracking elements (not illustrated in FIG. 20) that allows determination of the position and distance of the emitter 110 relative to a non-moving sensor or the sensor's working area 116.

Figure 21A:
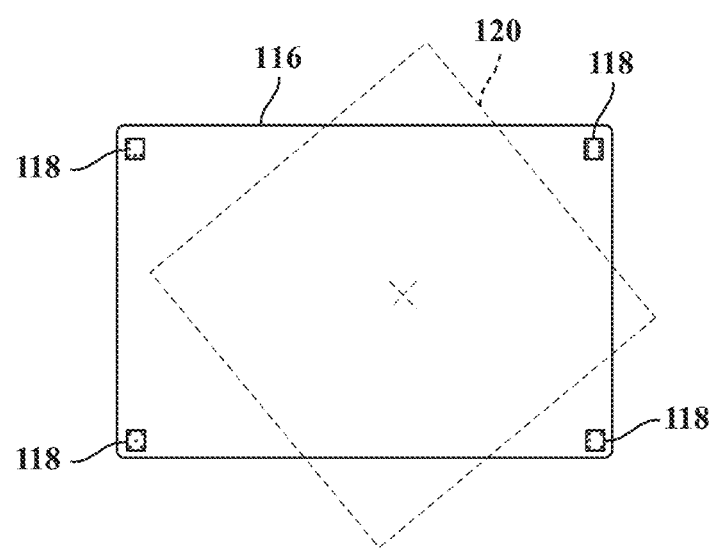
FIG. 21A represents a situation in which an emission profile extends beyond a sensor such that the emitter is not in operative alignment with the sensor.
Figure 21B:
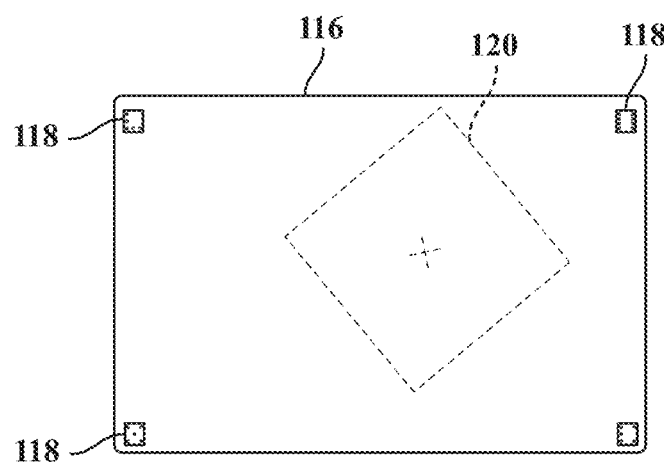
FIG. 21B represents a situation in which an emission profile is scaled to remain within a perimeter of an imaging sensor and is in operative alignment with the sensor.

FIG. 21A represents a situation in which an emission profile 120 extends beyond the sensor 116 such that the emitter is not in operative alignment with the sensor 116. For purposes of illustration, the sensor 116 shown in FIGS. 21A and 21B, is stationary and tracking elements 118 permit the system to determine the relative location, orientation, and distance of the emitter (not shown) relative to the sensor 116. Also, the emission profile 120 is illustrated as a representation of a boundary of the emission provided by the emitter. For purposes of illustration, the profile 120 illustrated is a profile that would occur if an axis of the emitter is perpendicular to the sensor 116.

As noted herein, if the system cannot establish operative alignment given the condition shown by FIG. 21A, the operator will be prompted to adjust the position of the emitter. In some variations, the system can provide feedback such as an audible or visual indicator of non-alignment. FIG. 21B shows a situation after repositioning of the emitter such that the emission profile 120 falls within the boundary of the sensor 116. However, as shown, this emission profile 120 is not maximized to the dimensions of the sensor 116. Failure to maximize the emission profile 120 relative to the sensor can require the operator to take additional radiological images of the subject to adjust for a smaller profile.

Figure 22A:
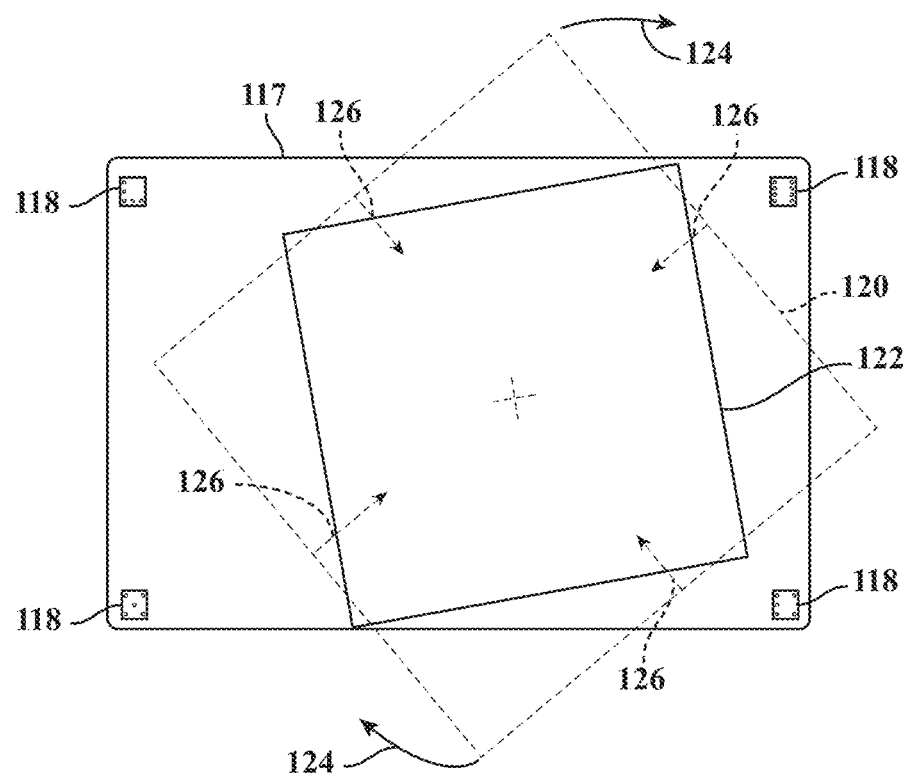
FIGS. 22A and 22B illustrate an example of the effect of an adjustable collimator to produce an adjusted emission profile that is scaled and/or rotated to remain within the perimeter of an imaging sensor.

FIG. 22A illustrates the effect of an adjustable collimator. Again, for purposes of illustration, the emission profiles shown represent illumination by an emitter that is perpendicular to a sensor. FIG. 22A shows an unadjusted emission profile 120 that would ordinarily be considered out of operative alignment with the imaging sensor 116 given that a portion of the emission area bound by the profile 120 falls outside of the sensor 116. However, a variation of the system described herein will rely on the position tracking elements 118 as well as components affixed to the emitter (as described above) to determine positional information such as an orientation of the emitter as well as a distance between the emitter and the sensor 116. The system will use the positional information to adjust a collimator on the emitter to rotate and/or scale emission by the emitter to produce an adjusted emission profile 122. As shown, in this variation, the adjusted emission profile 122 is reduced in size (denoted by arrows 126) and also rotated (denoted by arrows 124) to scale the emission profile 120 into an adjusted emission profile 122 that maximizes an exposure onto the imaging sensor. It is noted that the adjusted emission profile can be scaled or rotated as needed. Moreover, variations of the system will produce an adjusted profile during real-time movement of the emitter relative to the sensors 118.

Figure 22B:
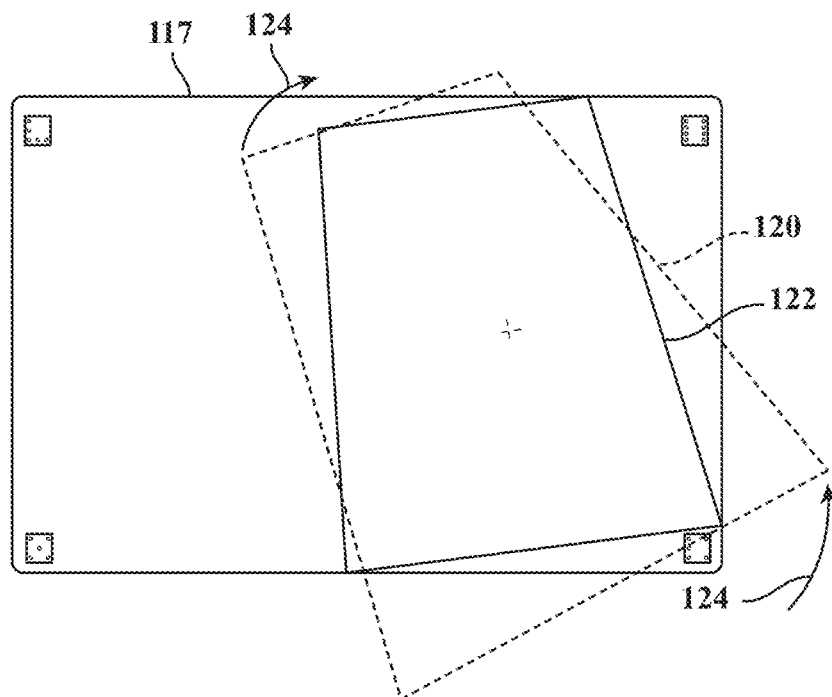

FIG. 22B illustrates an unadjusted emission profile 120 along with the adjusted emission profile 122, where in both cases, the profile resembles an isosceles trapezoidal shape due to an axis of the emission path not being perpendicular or normal to the sensor 116. However, in this variation, the system uses the positional information to produce an adjusted profile 122 that maximizes an exposure area on the image sensor 116.

While the variations disclosed herein rely on tracking elements 118 as well as sensors within the emitting unit (as described herein). Variations of the system that produce an adjusted emission profile can also be used with positional data that is derived from external cameras, sensors, or mechanical supports to determine relative movement between an emitting apparatus and an imaging sensor.

Figure 23:
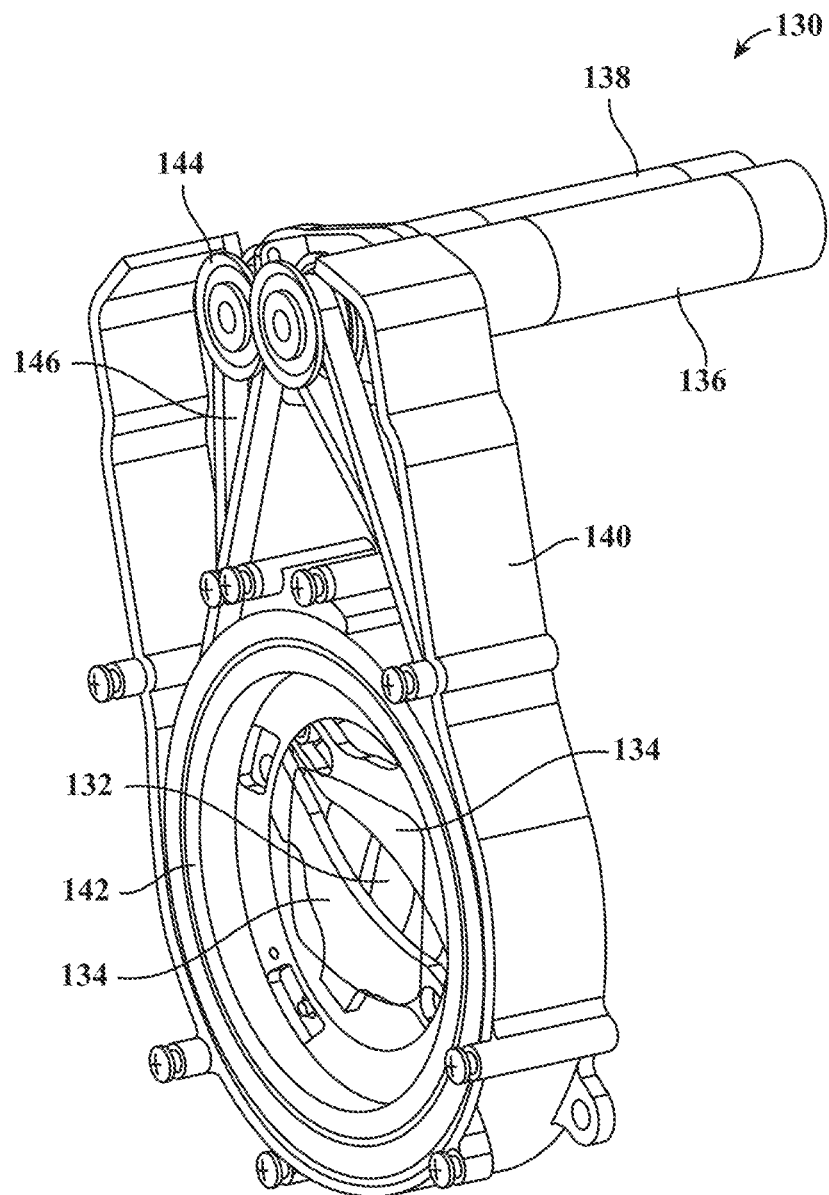
FIG. 23 shows a variation of an adjustable collimator that can be used in or with an emitting apparatus.

FIG. 23 shows a variation of an adjustable collimator 130 that can be used in or with an emitting apparatus (not shown in FIG. 23). As illustrated, the adjustable collimator 130 can rotate and/or scale an aperture or emission window 132 to produce an adjusted emission profile upon an imaging sensor (as discussed in FIGS. 20 to 22B). This variation of the adjustable collimator 130 uses a number of blades or leaves 134 that can move and rotate to adjust an orientation of the aperture 132. The blades 134 prevent passage of the emitted energy such that energy is limited to pass through the aperture or emission window 132.

The movement and rotation of the blades can be driven by any number of motors or drives. In the variation shown, the adjustable collimator 130 includes a motor assembly having a first drive 138 coupled to a proximal slewing bearing 152 and a second drive 136 coupled to a distal slewing bearing. The drives 136 and 138 adjust the rotation of the blade 134s as well as a sizing of the aperture 132. For example, rotation of the motors 136 and 138 in opposite directions causes rotation of the slewing bearings in the opposite direction and produces movement of the blades 134 to cause opening/closing of the aperture 132. In the example shown, if the first drive 138 moves in a clockwise direction and the second drive 136 moves in a counter-clockwise direction, then the blades 134 will move towards each other, causing a size of the aperture 132 to decrease. Likewise, if the first drive 138 moves in a counter-clockwise direction and the second drive 136 moves in a clockwise direction, then the blades 134 will move away from each other causing a size of the aperture 132 to increase. If the drives 138 and 136 move in the same direction, this will cause rotation of the proximal and distal slewing bearings 150 and 152 in the same direction, which will cause rotation of the blades, which causes rotation of the aperture 134.

The adjustable collimator 130 maintains an aperture 132 having a near-square shape since all of the blades 134 move to adjust the size of the aperture. Additional variations of the device can include any number of additional motors or actuators to also control an angular orientation of the blades. In such a case, the aperture 134 is not limited to a square profile and can assume an isosceles trapezoidal shape. Such a feature can assist in maintaining a square emission profile (such as that shown in FIG. 22A) regardless of the orientation of an axis of the emission energy to the imaging sensor.

The variation of an adjustable collimator 230 shown in FIG. 23 also includes a chassis or housing 140 that houses the drive mechanism (e.g., bearings, pulley 144, belts 146, etc.) that translates the movement of the gears 144 driven by motors 136, 138 into rotation and movement of the blades. Furthermore, the adjustable collimator 230 will include any number of positioning tracking systems that enable the system to maintain information regarding a size and rotational orientation of the aperture. For example, a first moveable disk (or encoder wheel) 142 is shown as part of an optical encoder system that can use any conventional light source, sensor, mask, and photosensor (e.g., a photodiode).

Figure 24A:
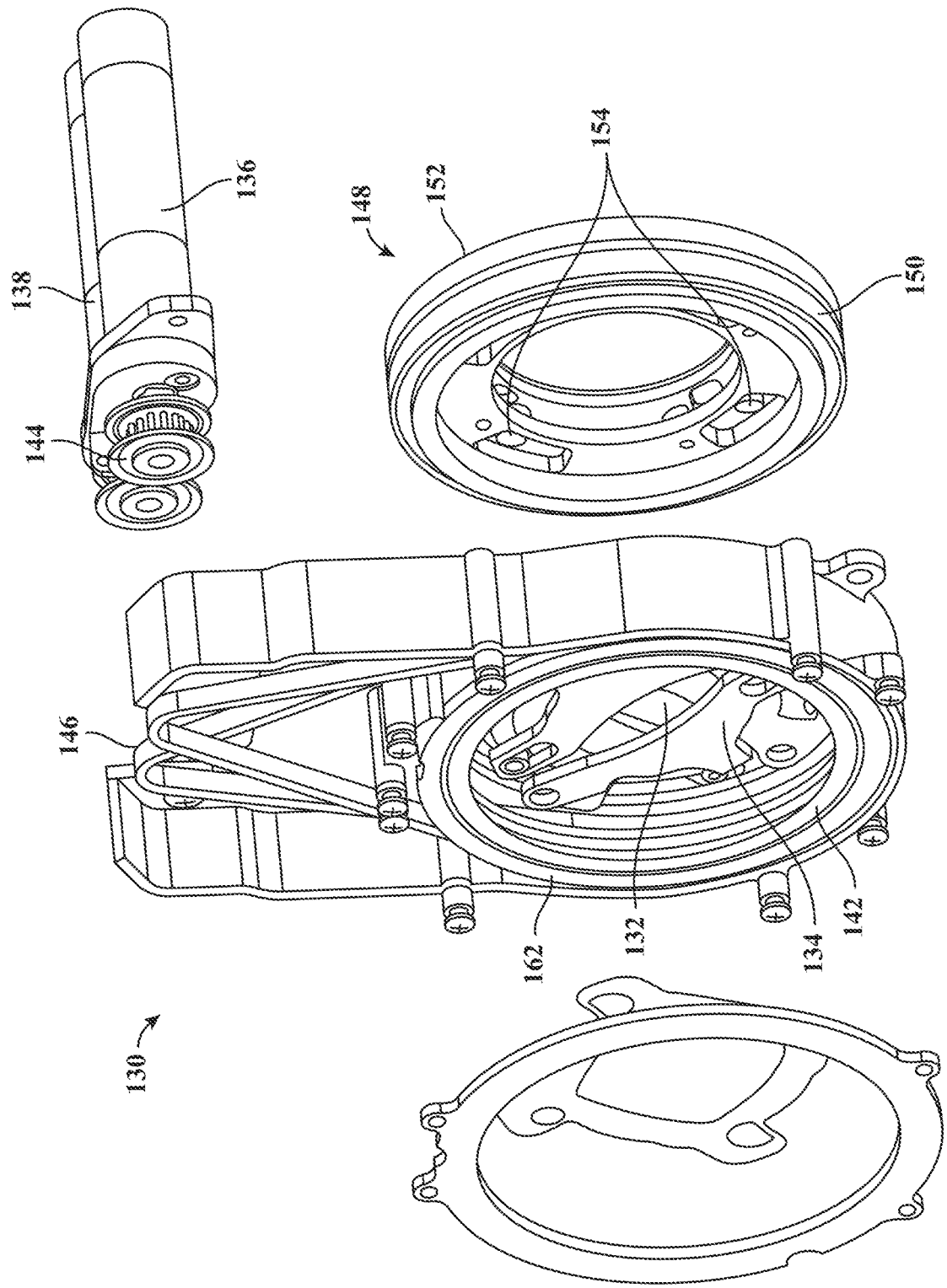
FIG. 24A shows an exploded view of an example of an adjustable collimator.
Figure 24B:
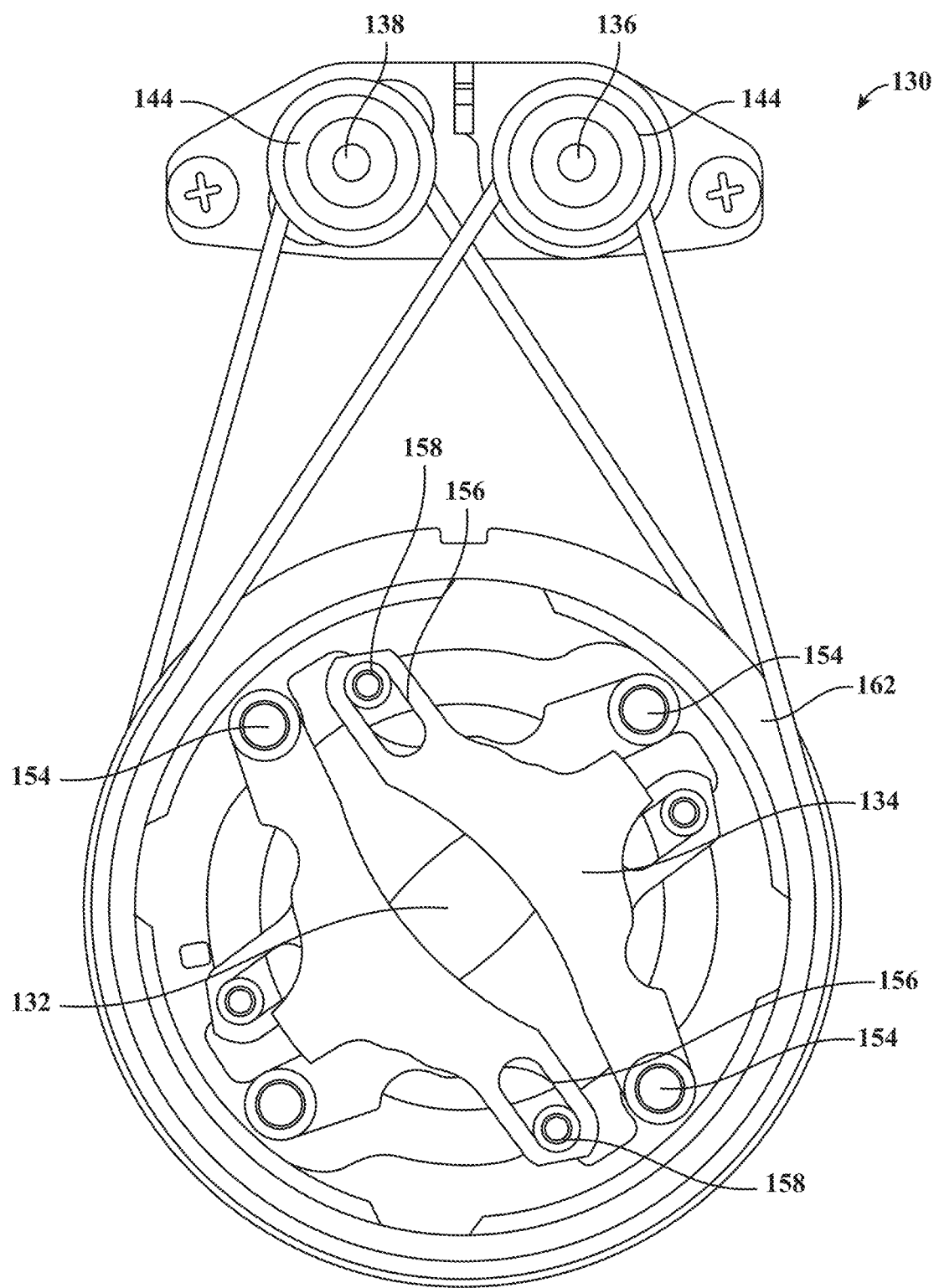
FIG. 24B illustrates a front view of some of the components of the adjustable collimator of FIG. 24A

FIG. 24A shows an exploded view of an example of an adjustable collimator 130 to illustrate a variation of the mechanism used to rotate and scale the aperture 132 formed by the blades 134. As illustrated, pulleys 144 coupled to the motors 136 and 138 rotate belts 146 that are coupled to a cam/pin assembly 148. The blades 134 are housed in the cam/pin assembly 148, but for purposes of illustration, the cam/pin assembly 148 is shown without the blades. The assembly 148 comprises a cam wheel 150 and a proximal slewing bearing 152 that are each coupled to a respective motor 136 and 138 via the belt system 146. The blades 134 coupled to one or more pins 154 within the assembly 148 of slewing bearings 150 and 152 such that rotation of the slewing bearings 150 and 152 causes a scaling of the aperture 132 as discussed above. This scaling is caused through movement of the blades 142 closer or farther apart. The rotation of the aperture 132 is caused by rotation of the slewing bearings 150 and 152 in the same direction FIG. 24B illustrates a front view of some of the components of the adjustable collimator 130 (a number of components are removed for the sake of illustration). As shown, the aperture 134 is defined by area surrounded by the blades 134. Each blade is coupled to a pin 154 at one end. The opposite end of the blade 134 includes a bearing 158 within a slot 156. Actuation of the motor 138 causes movement of the bearing 158 within the slot 156 while the blade 134 pivots about the pin 154, which causes the blades to move closer together or farther apart (depending upon the direction of rotation) at the aperture 132 to produce a scaling of the aperture 132. Rotation of the aperture 132 occurs when motor 136 causes rotation of the cam wheel 150 (shown in FIG. 24A). As noted above, rotation of the aperture 132 requires rotation of the slewing bearings 150 and 152 in the same direction.

Figure 24C:
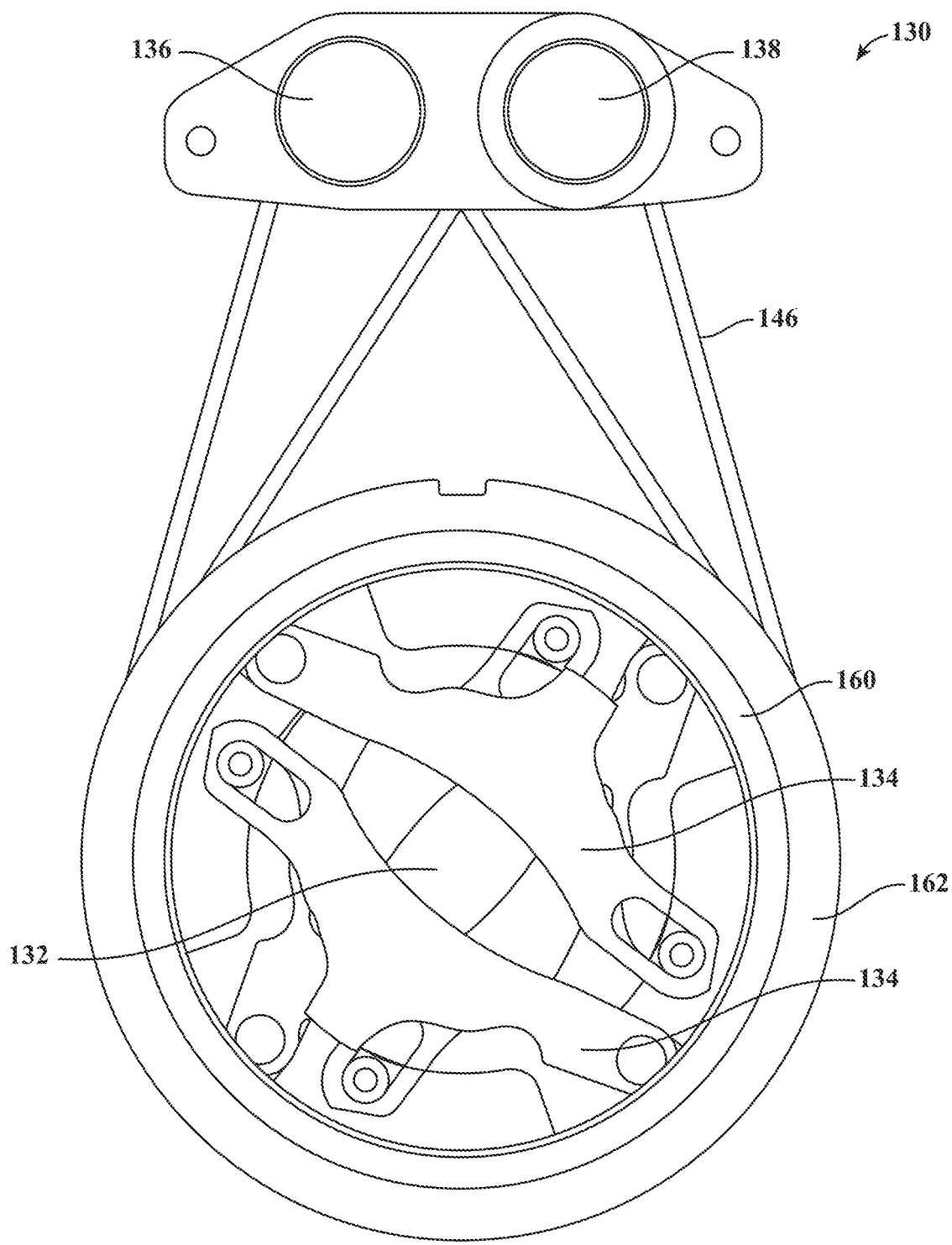
FIG. 24C illustrates a rear view of some of the components of the adjustable collimator of FIG. 24A.

FIG. 24C illustrates a rear view of some of the components of the adjustable collimator 130 (a number of components are removed for the sake of illustration). As shown, the collimator 130 includes a second moveable disk (or encoder wheel) 160 that is shown as part of an optical encoder system that can use any conventional light source, sensor, mask, and photosensor (e.g., a photodiode) to track movement of the blades 134.

Figure 25B:
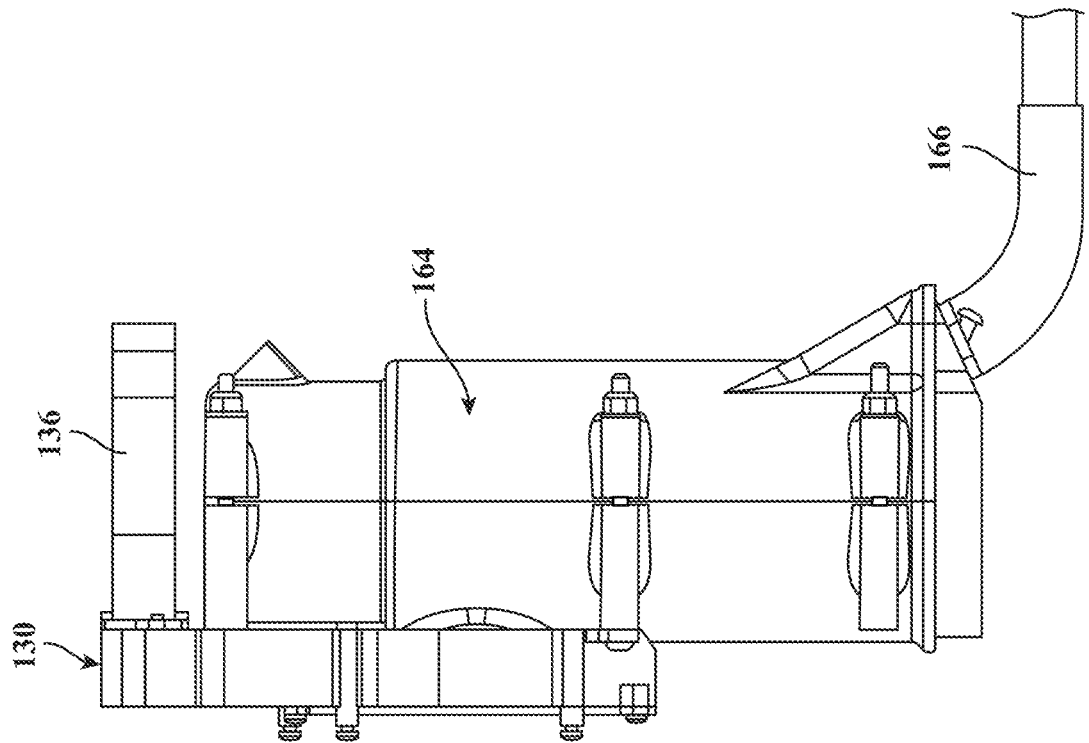
FIGS. 25A and 25B illustrate an example of an emitter having an adjustable collimator.
Figure 25A:
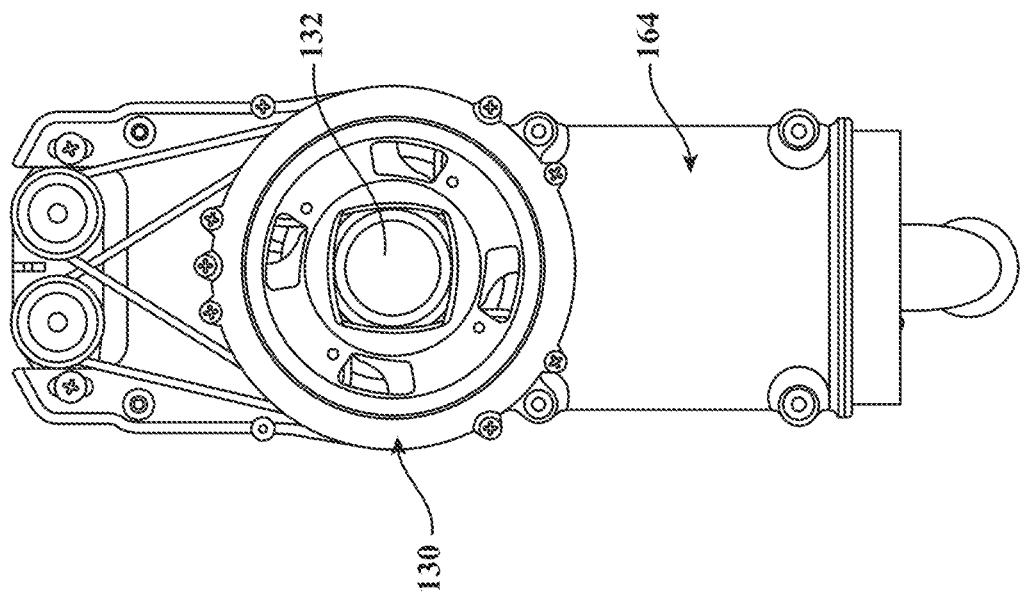

FIGS. 25A and 25B illustrate an example of an emitter 164 having an adjustable collimator 130 as discussed above. As shown, the adjustable collimator can rotate and scale the aperture 132 based on information regarding the distance and orientation of the emitter from the system's position tracking elements. The scaling and rotation of the aperture 132 can be automatic or can occur on demand. FIGS. 25A and 25B show a variation of the emitter having cabling 166. In other variations, the emitter and adjustable collimator can be used on a fully portable emitter as described herein.

The optical encoders 160 in FIG. 24C ensures leaf or blade positioning to ensure patient safety. The encoder 160 can also assist in determining any number of conditions that could create a failure state: For example, the encoders can detect conditions, including but not limited to: drive belts skipping a tooth on the gear, drive belts breaking or losing tension, motor malfunctions, broken ring gear, broken leaf pin, etc. Detection of such a failure state can prevent the emission source from triggering to avoid exposing the patient or operator to excess radiation.

FIGS. 26A to 26J illustrate an example of a validation method for the collimator discussed herein. The rolling collimator has two processes that are executed to validate the mechanical operation and alignment of the device. Due to the emission of ionizing radiation from the X-ray tube, it is imperative that the mechanical function of the device is validated before use, discovering any physical damage before exposing the operator to additional radiation. The freely mobile, untethered design of the device creates an additional challenge for the collimator: indexing the position of the wheels to an arbitrary alignment of the X-ray detector. The collimator executes a homing process to determine the min/max aperture positions and the 0° position of the device. The homing process establishes the zero-orientation reference required for collimator aperture control. The leaf detection process validates the physical operation of the device by verifying the full range of aperture sizing.

Figure 26A:
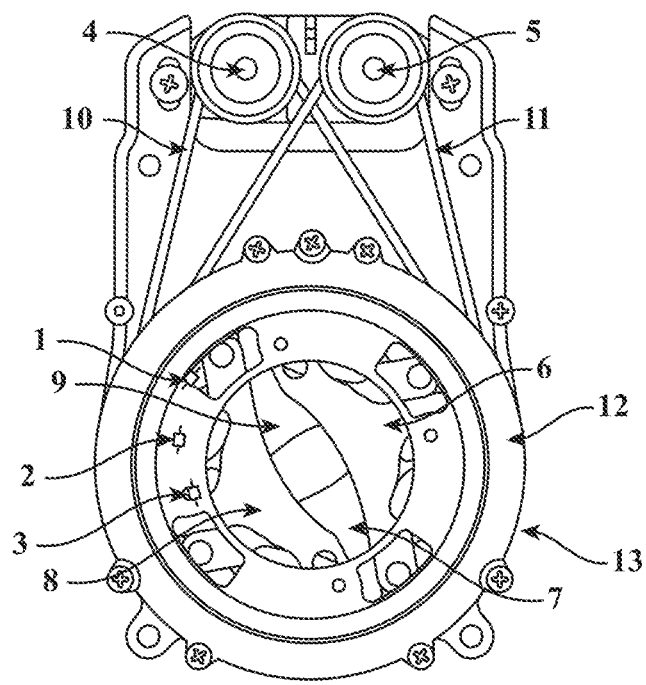
FIGS. 26A to 26J illustrates an example of a validation method for the collimator discussed herein.

FIG. 26A shows a random position of the leaves of the collimator device. This position could be the orientation of the device after a previous operation, from a previous procedure, or any other scenario. The device has no knowledge of the aperture or orientation until after the homing process. The device consists of (1) (2) (3) optical sensors to monitor the position of leaves, (4) (5) motors to drive a distal slew ring (12), and a proximal slew ring (13) connected by a pair of belts (10) (11). The four collimation leaves (6) (7) (8) (9) are connected to the slew rings in pairs.

The optical sensors (1) (2) (3) operate by detecting the presence or absence of leaf material directly in front of the sensor. The sensor is considered open if there is no material in front of the sensor. It is considered closed if the presence of the material is detected.

Figure 26B:
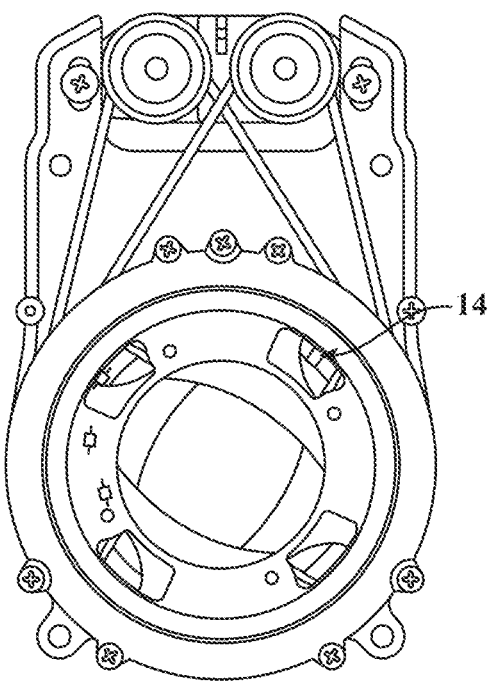

Homing Procedure:

Step 1: Open Position—The homing procedure is executed any time the device is powered on, any time the device has been in an idle state, or any time the device has detected drift. The device begins by rotating the proximal ring until the device detects movement in the distal ring by linkage. FIG. 26B shows the non-determinate position of this scenario, illustrated by the visibility of the home keyway (14). This alignment allows the optical sensor 1 to detect an open state when the keyway is directly in front of the sensor. This is the fully open position of the collimator.

Figure 26C:
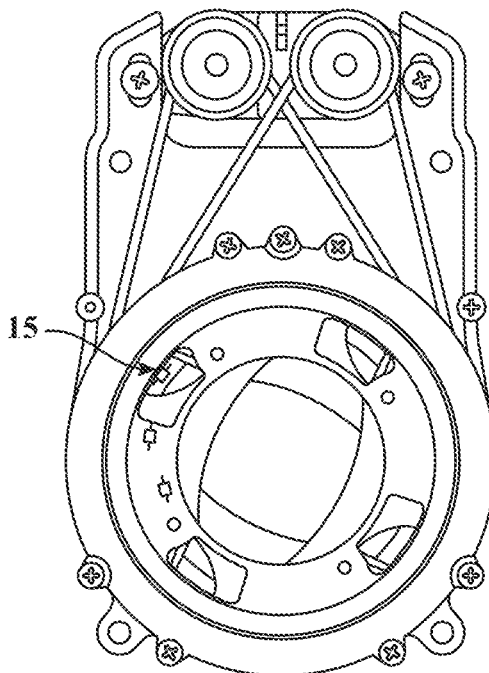

Step 2: 0 Degree Position, Maximum Aperture—FIG. 26C shows the 0 degree, maximum aperture position. Once the fully open position has been determined, the device will rotate the proximal and distal rings concurrently, rotating the leaf assembly. The system will monitor the status of optical sensor 1 until such a time as the sensor registers open (15). This open signal indicates that the keyway has rotated into the position of the sensor at the fully open position. The system then registered this as the fully open, 0 degree position.

Figure 26D:
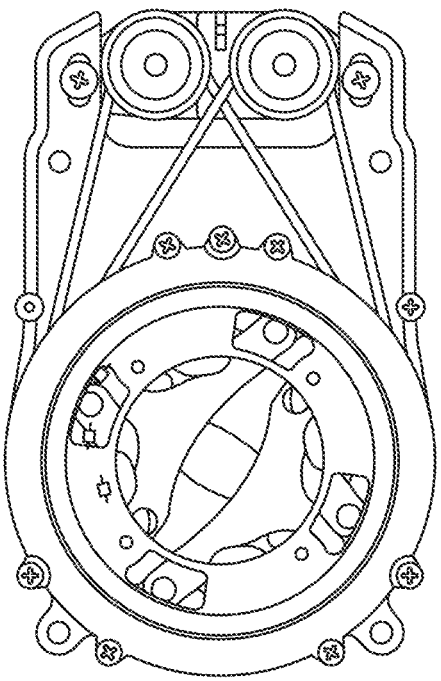
Figure 26E:
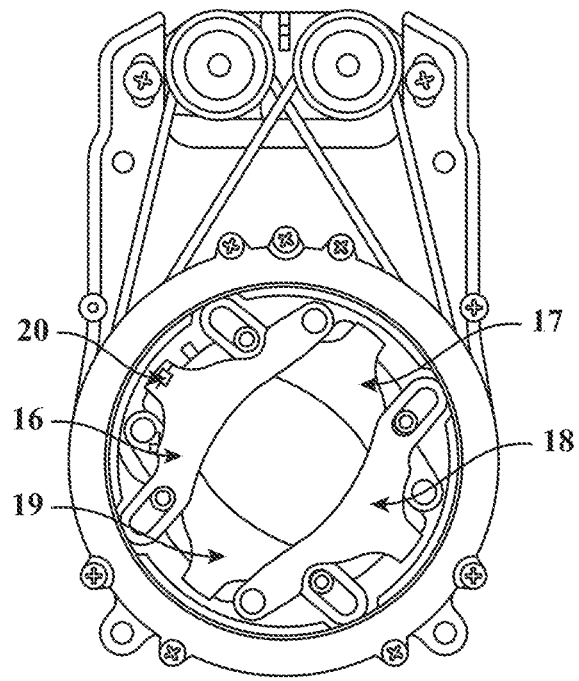
Figure 26F:
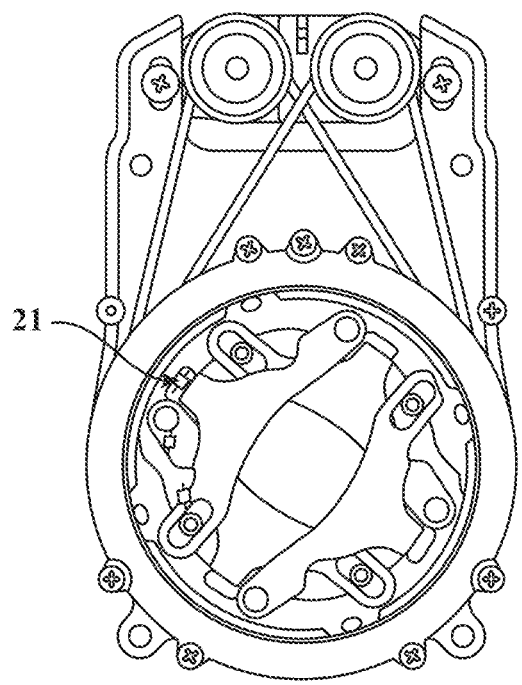
Figure 26G:
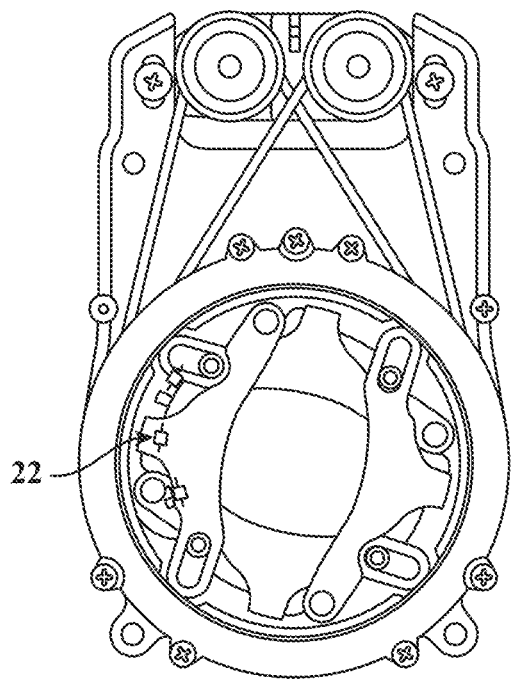
Figure 26H:
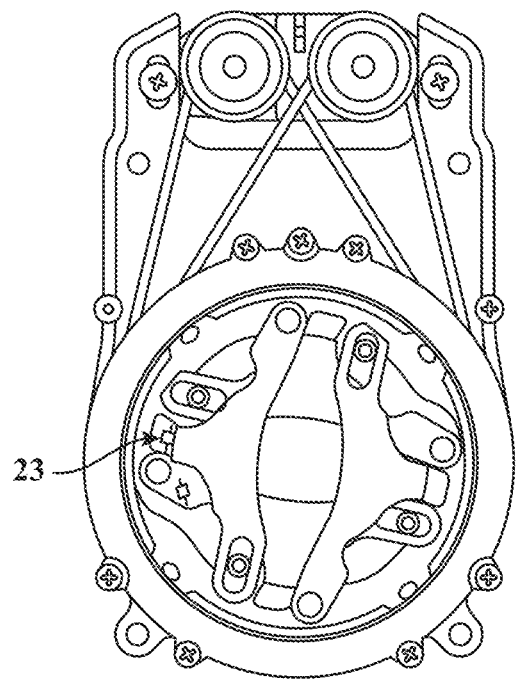
Figure 26I:
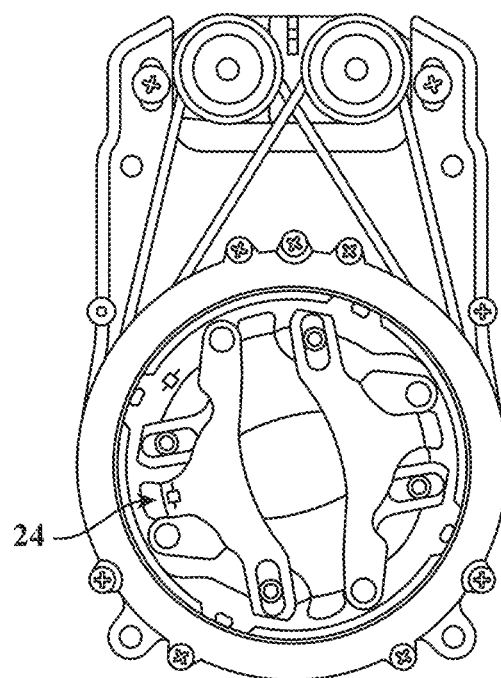
Figure 26J:
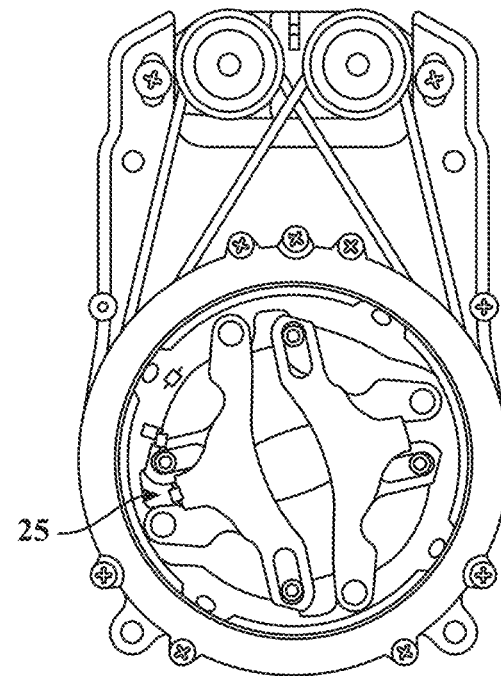

Step 3: 0 Degree Position, Minimum Aperture—The device will then turn the distal slew ring until such a time as it detects movement in the proximal slew ring. When this movement is detected, the system will then register the 0 degree, minimum aperture position as shown in FIG. 26D.

These positions are then registered for the current operational session. With the motor position recorded, the device can calculate the relative movement of the motors and slew rings to any other necessary position.

Damage Detection Procedure:

As described above, a fully operational, undamaged collimator is essential to the safety and performance of the collimation system. Furthermore, detecting any damage or drift is critical before any emission is released through the device. In order to guarantee performance, the device will consecutively check the positioning status of each leaf.

At minimum, a single check of each leaf is necessary; however, due to the safety nature of this process, the exemplary device uses a three-position check. The optical sensor array (1) (2) (3) is used to validate individual leaf performance, but any number of sensors could be used to execute the process. The order of the checks can vary. Once the three-step process has been completed for the first leaf (16), the process will move on to validate leaf two (17), leaf three (18), and leaf four (19). The process is applicable to any number of leaves.

Step 1: Maximum Aperture Validation—Sometime after the homing process has been completed, the device will roll the leaf assembly into Optical Sensor 1 closed position (20) FIG. 26E by moving both proximal and distal rings as necessary to create the fully opened aperture. The device will then immediately move into Optical Sensor 1 open position by moving the rings to reduce the aperture FIG. 26F. If the calculated movements of the device match the physical feedback of Optical Sensor 1 (21), the device has validated the maximum aperture position for leaf 1 (16).

Step 2: Median Aperture Validation—Sometime after the homing process has been completed, the device will roll the leaf assembly into Optical Sensor 2 closed position (22) FIG. 26G by moving both proximal and distal rings as necessary to create the median aperture. The device will then immediately move into Optical Sensor 2 open position by moving the rings to reduce the aperture FIG. 26H. If the calculated movements of the device match the physical feedback of Optical Sensor 2 (23), the device has validated the maximum aperture position for leaf 1 (16).

Step 3: Minimum Aperture Validation—Sometime after the homing process has been completed, the device will roll the leaf assembly into Optical Sensor 3 closed position (24) FIG. 26I by moving both proximal and distal rings as necessary to create the minimum aperture. The device will then immediately move into Optical Sensor 3 open position by moving the rings to reduce the aperture FIG. 26J. If the calculated movements of the device match the physical feedback of Optical Sensor 3 (25), the device has validated the maximum aperture position for leaf 1 (16).

Once Step 3 has been completed for Leaf 1, the device will then repeat the procedure for each leaf, guaranteeing that each leaf is in the expected position.

Figure 27:
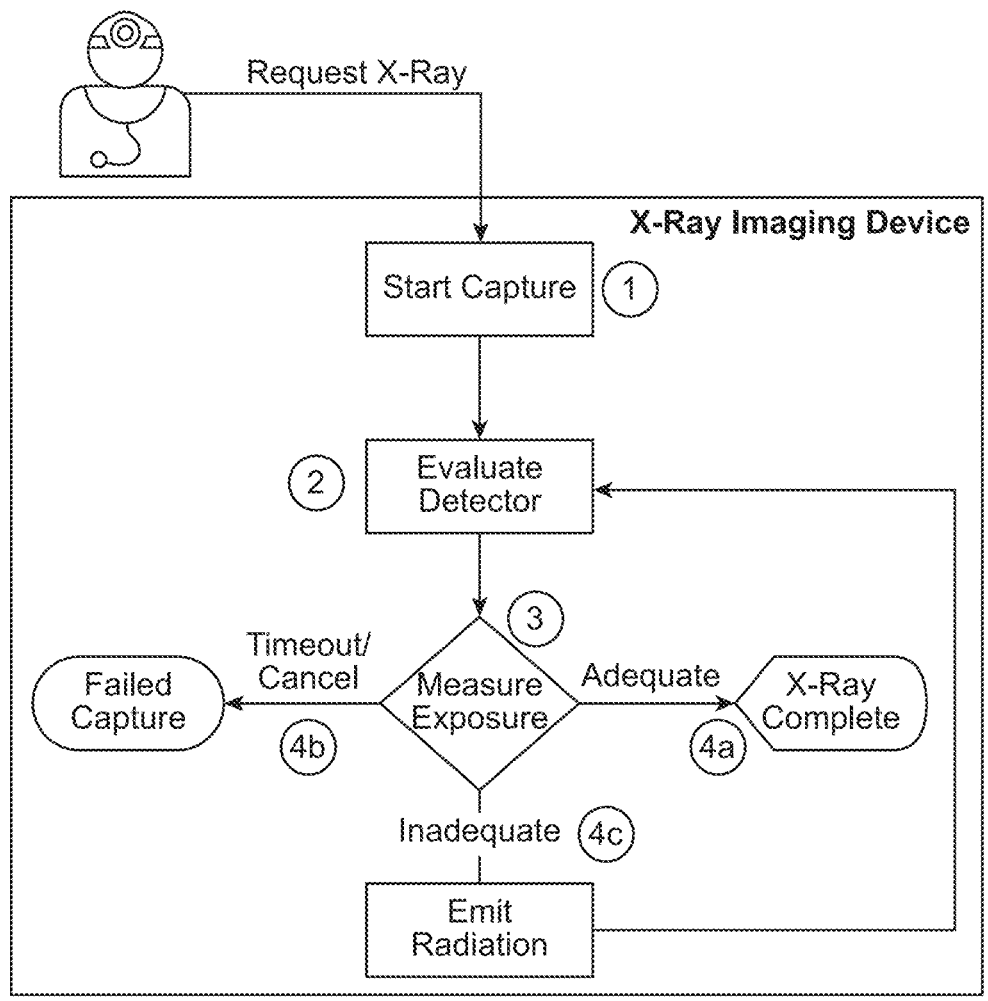
FIG. 27 illustrates an example of a traditional automatic exposure process.
Figure 28A:
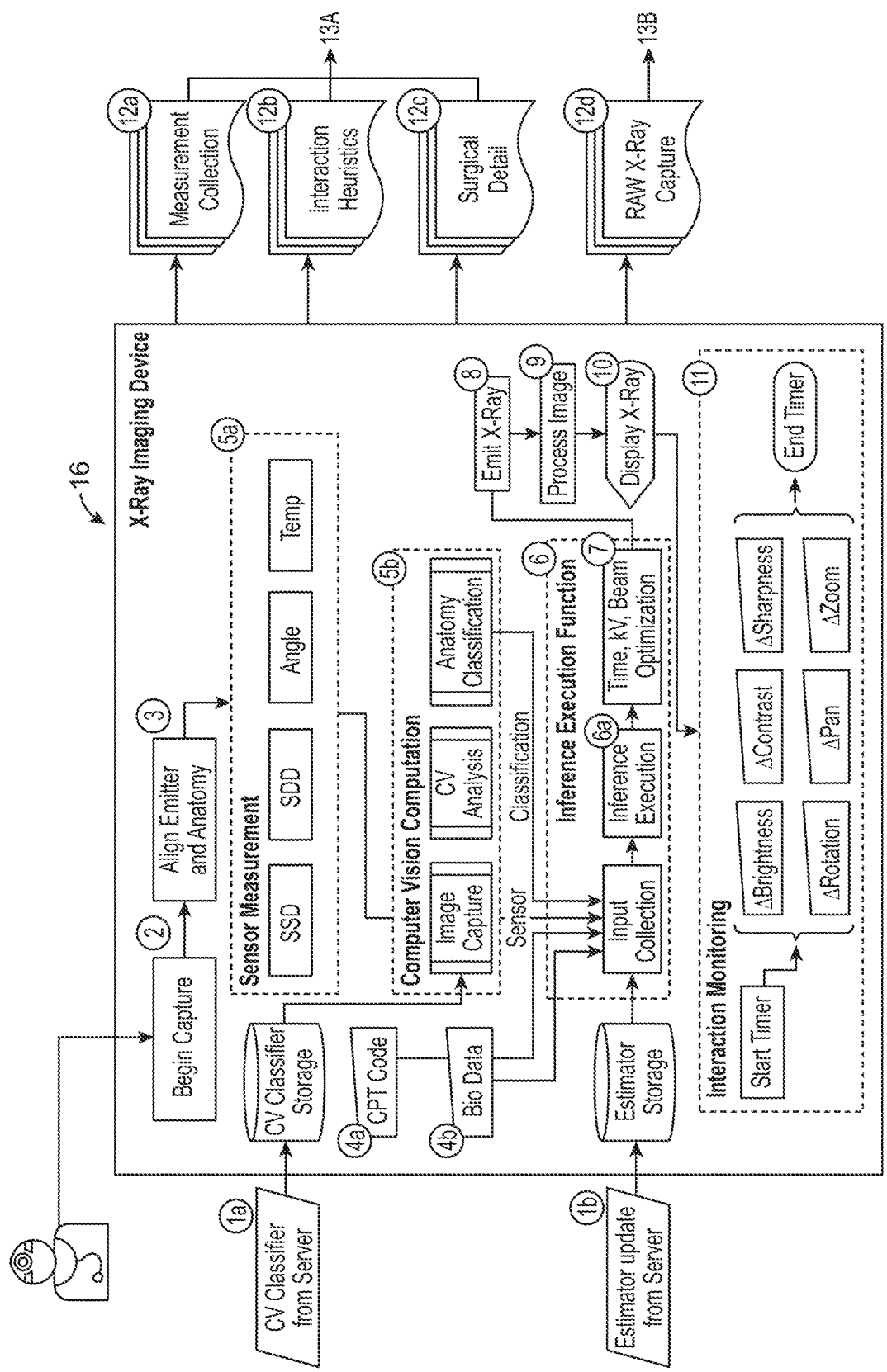
FIG. 28A illustrates an improved system that relies upon one or more databases to provide machine learning for determination of exposure settings for a radiological image.
Figure 28B:
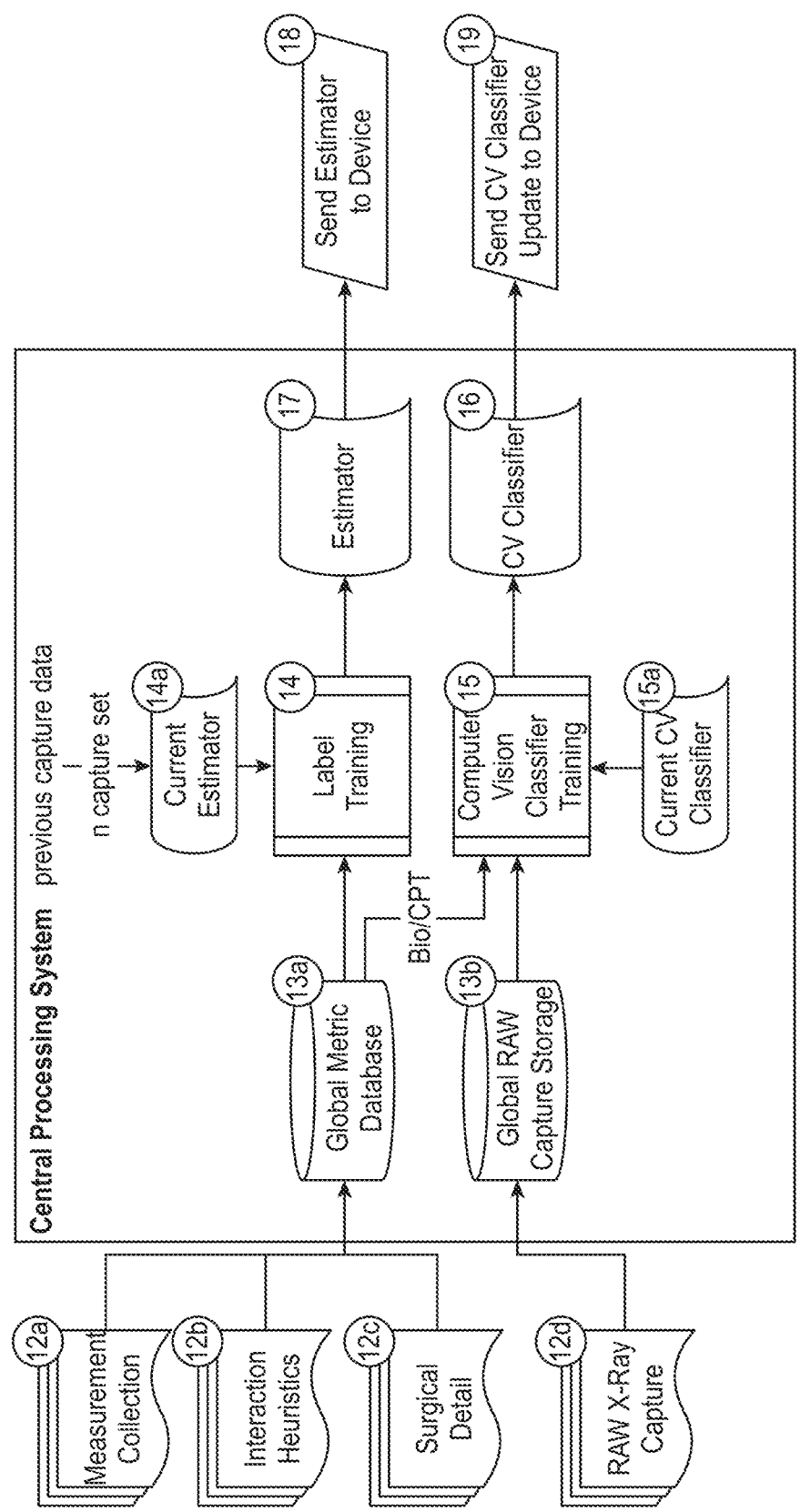
FIG. 28B illustrates a process of improving the automatic exposure process and databases using feedback from the systems described herein.

FIGS. 27 and 28A-28B illustrate another aspect in which a radiological system having a sensor configuration as described herein can improve the quality of an X-ray or fluoroscopic capture.

The quality of an X-ray or fluoroscopic capture is related to a number of physical attributes of the subject. These elements dictate a set of technique factors (e.g., power, current, time, etc.) that control the emission characteristics of the radiation source/emitter. It is the responsibility of the device operator to set these factors in such a combination that the individual viewing the radiological image can identify the necessary visual elements without exposing the subject to excess radiation.

Setting these technique factors can be complex. In order to relieve the operator of the burden of setting these techniques manually, existing fluoroscopic devices have implemented an automatic process. The typical approach uses a software or a hardware dose detector on the plate that gradually fills as radiation is added to the exposure. This conventional approach has a number of problems.

One major issue with the conventional approach is movement. Because the radiation is exposing the subject for an extended time period, any movement whatsoever, either in the subject, the operator, the machine, vascularity inside the subject, etc., creates motion artifacts that severely degrade the image.

Another issue is that penetration requirements are not known before the exposure; therefore, as the source emits radiation at a given power level (kV), frequently, there is not enough penetration to render an image. This failure to render an image exposes the patient, operator, and staff to radiation without producing any useful radiological image. In such a case, these individuals are exposed to excess radiation that does not serve any clinical purpose.

Innovation in the fluoroscopic device space, including but not limited to the systems described herein, creates a new generation of machines with complex sensor arrays capable of directly measuring a number of the physical elements required for exposure calculation.

By utilizing these sensors across the full spectrum of devices and subjects, as well as robust machine learning techniques, it is possible to compute the necessary techniques before exposure, eliminating motion artifacts and creating an outstanding capture, all while reducing dose.

The following descriptions provide exemplary details of the invention in order to provide an understanding of the invention. Small engineering adjustments could be employed to practice the invention without employing these specifics. While the invention is described for use in X-ray imaging for surgical purposes, it could be used in other medical applications, including but not limited to general medical imaging, veterinary, and bone densitometry. It could be used for non-medical applications such as industrial imaging, metal fatigue inspections, weld-inspection, for security inspections, and the like.

FIG. 27 shows a diagram of an example of a conventional methodology for automatic X-ray exposure process. The doctor or operator begins the exposure (step 1) by requesting the X-ray be taken. The X-ray device will then evaluate the detector (step 2), tracking the amount of radiation received on the imaging sensor plate. An internal measurement of X-ray machine will determine if this energy is a sufficient amount of exposure to generate an image (step 3). If the device determines that an adequate amount of radiation is collected (step 4a), it will deem the exposure complete and display the X-ray. If the user cancels the X-ray or the dose has been accumulating for too much time, the machine will cancel the exposure (step 4b.) Otherwise, (step 4c)u, the device will continue to emit radiation, returning back to the evaluation step until the image is created, time runs out, or the user cancels the exposure.

The traditional process has a number of drawbacks. The two largest are that: exposure begins without a guarantee that an image will appear and that the time taken to evaluate the exposure introduces movement artifacts in the final image, creating an unusable X-ray. In either case, the patient, operator, and staff are exposed to unnecessary radiation, which is a major safety hazard.

FIGS. 28A and 28B illustrate an improved approach over the conventional methodology described in FIG. 27. The improved approach can determine the optimal technique factors to create a resolute and effective radiological image without exposing the operator, staff, and patient to unnecessary or excessive radiation. By utilizing a radiological imaging device with a comprehensive sensor array and an enterprise-wide application of machine learning techniques, the system 20 can calculate and refine the techniques before any radiation is emitted. This allows an operator to precisely align the device and understand if the machine is capable of imaging the anatomy.

FIG. 28B illustrates an example of how statistical data can be compiled for use in the imaging process of FIG. 28A. In practice, a number of statistical models are transmitted to the system 20 from a central server (shown in FIG. 28B). These models, referred to as the Computer Vision Classifier (1a) and the Estimator Update (1b), are stored locally on the machine and ready for use prior to the operator requesting the exposure.

Turning to FIG. 28A, the process can begin with the operator initiating the capture (2). The operator then uses the positioning system of the device to align the emitter and anatomy (3), completing the safety checks, then executing the automatic technique detection (as described above). Depending on the exact topography of the X-ray system, CPT Code information (4a) and or Biometric Information (4b) may be entered by an operator or extracted from another system by automatic means.

As the system prepares to emit the energy for either X-ray or fluoroscopic capture, two concurrent measurement collections are happening: on-device sensor collection (5a) and computer vision classification (5b).

The sensor collection uses the array on the device to collect a multitude of input parameters, including, but not limited to, source-to-skin distance (SSD), source to detector distance (SDD), angle of incidence, ambient, X-ray tube and device temperature, etc. These parameters are all fed into the inference execution function (6).

The computer vision classifier utilizes the imaging camera on the device to capture pictures of the subject anatomy. These images are passed into the CV analysis function, using the captured images as well as the CV Classifier data that is stored locally on the device provided by the central server. These processes make a determination about that subject of the capture and passes that recommendation to the Inference Execution Engine.

Once the inputs are collected from the device's various subsystems, those values, along with the Estimator Update provided by the central server, are run against the device's inference execution engine (6a). The output of that function family is the determined X-ray technique: time, kV and beam current (7).

The device output is set to the computed values, radiation is emitted for the given settings (8), the image is captured and processed (9) and the image is displayed to the user. (10)

As soon as the X-ray is displayed to the operator, the system immediately begins monitoring the operator interaction in the Interaction Monitoring system (11). This system records every interaction the operator has with the image, which includes changes in brightness, sharpness, contrast, position, zoom, rotation, etc. The amount of time the operator spends examining the X-ray or fluoroscopic capture is also recorded.

In steps 12a-12d, the system will submit capture data to the central processing system. The submitted data includes the four major components of the capture: (12a) Direct Measurement Information, such an SSD, temperature, etc. (12b) interaction heuristics, such as the changes in brightness or the amount of time spent examining a capture. (12c) includes the surgical detail, such as the biometric information, any associated CPT code, as well as the computer vision captures and resulting classification output. (12d) includes the raw capture data from the detector itself as well as capture associated information, such as machine details, software versions, etc.

This capture information is stored on the central processing system in respective databases 13a and 13b for future processing.

At a scheduled time, the central processing system will train the estimator labels (14) using a sophisticated regression analysis. By examining the statistical relationship between the sensor data, capture data and surgical data across a large section of universally captured X-rays, as well as the results of the previous estimator generation (14a), the system can fit data to more accurate labels. The output of the training step is a new estimator (17).

Like the label training step (14), the X-ray and fluoroscopic capture data, surgical detail data and classifier data will be trained using a classifier refinement process (15). This process uses the large capture cross-section from the huge number of input X-rays to create a more accurate classifier (16).

Depending on the topography of the X-ray machines in the field, the central processing system will transmit the new estimator (18) and classifier (19) to the devices as soon as possible. They will then load these updates into the device local storage (1a) and (1b) and apply the new algorithms to further enhance the accuracy and reduce the dose of the automatic exposure.

Figure 29:
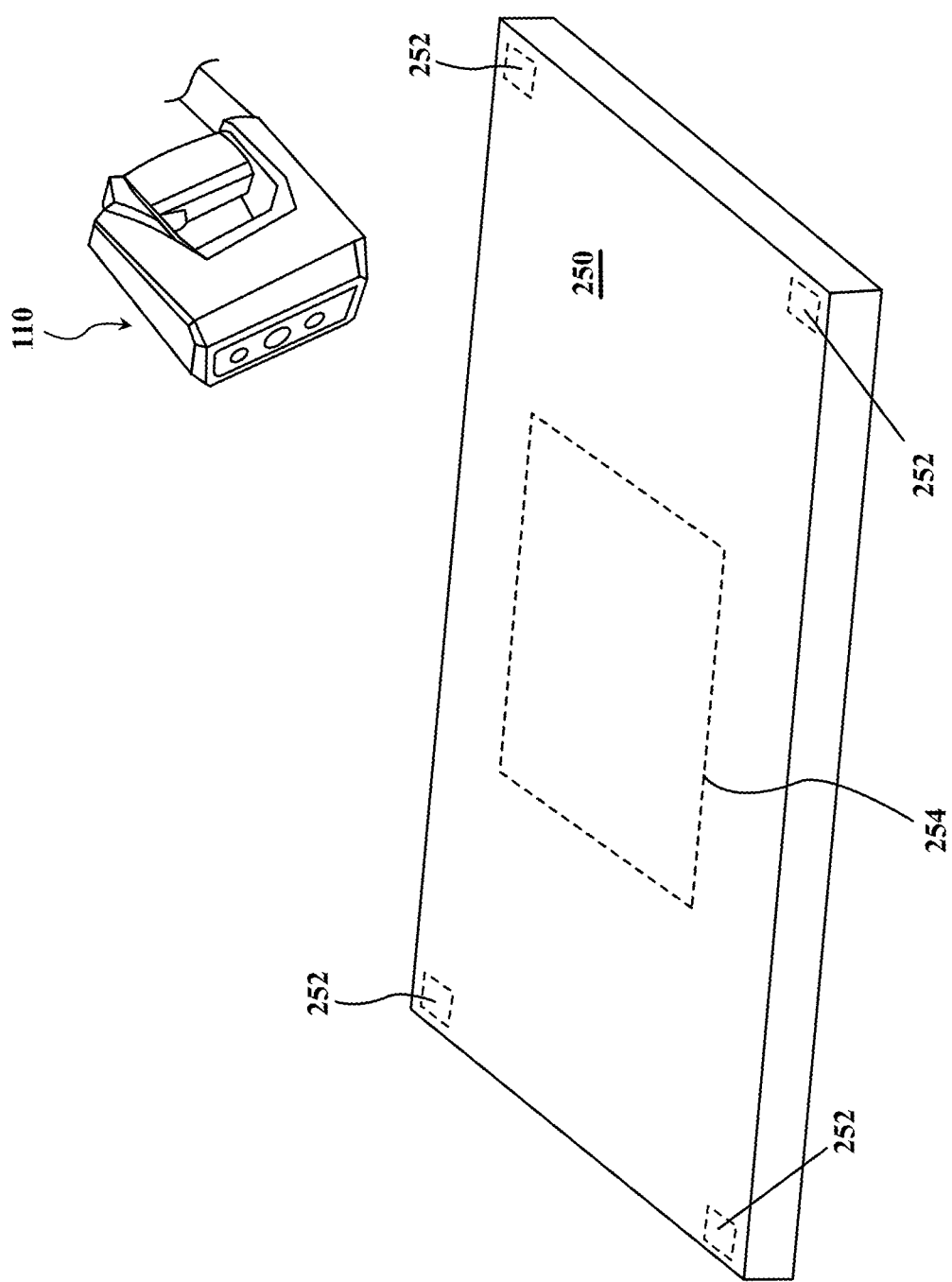
FIG. 29 shows an additional variation of an X-ray system using non-line-of-sight-tracking-elements such as electromagnetic tracking sensors.

FIG. 29 shows an additional variation of an X-ray system using non-line-of-sight-tracking-elements such as electromagnetic tracking sensors 252. Although the example of FIG. 29 shows 4 sensors 252, any number of sensors 252 can be used as required. While the system can operate with a single sensor 252, additional sensors can be used for redundancy. In operation, the electromagnetic sensors 252 generate an electromagnetic field to create a tracking space within a defined region (e.g., the operating tablespace 250) about a perimeter of the X-ray sensor 254. The emitter 110 includes one or more receivers that inductively couple with the magnetic field generated by the sensors 252. Since the sensors 252 allow for non-line-of-sight tracking of the emitter 110, the sensors 252 can be positioned within the working space 250. Alternatively, the sensors 252 can be visible, or their position can be marked on or around the working space 250. The ability of non-line-of-sight tracking allows for full-body imaging applications. Additionally, the non-line-of-sight tracking permits reducing the size of the structure housing the X-ray sensor 254. Any number of electromagnetic tracking field emitters and sensors can be used as an alternative or in addition to the tracking emitters discussed above.

Electromagnetic sensors and their operation are discussed in U.S. Pat. Nos. 4,054,881; 6,762,600; 6,624,626; 6,400,139; 6,377,041; and 6,369,564 the entirety of each of which is incorporated by reference. Such electromagnetic tracking systems are available from Polhemus (Vermont, USA) and NDI (Ontario, Canada).

Electromagnetic tracking systems (EM systems) can be very sensitive to interference from prevailing metallic objects or inductive motors. Accordingly, variations of an X-ray system using an EM system will additionally include one or more inertial measurement units (IMUs). In use, the X-ray system with EM tracking starts in a calibrated state. This calibration is held over from previous use or comes calibrated directly from the factory. As the X-ray system is in use, tracking of the X-ray emitter relative to the X-ray detector is accomplished by both the EM sensors and any IMUs. Typically, one or more IMUs are placed in the X-ray emitter and (optionally) an IMU placed in the X-ray detector. EM tracking and the differential positioning data supplied by the IMUs will generally line up. If at any point, both data sets do not align, the system can infer transient interference in the EM system and signal an error state. During this error state, the system can use the IMU data to smooth out any interference and generate a best-most-likely positioning state. Typically, this inference is sufficient to smooth the EM data and maintain system functionality. As the transient interference subsides, the IMUs data and EM sensors data will fall back into alignment.

In an additional variation, an X-ray system with EM tracking can use the X-ray emission to actively and continuously update the calibration. In such a case, collimation/beam angle of the X-ray emission from the emitter permits identification of the true position of the X-ray emitter when the emission was released through computer processing. The system can then use the true position calculated from the emission to determine if any offsets to the EM positioning system are required.

Figure 30:
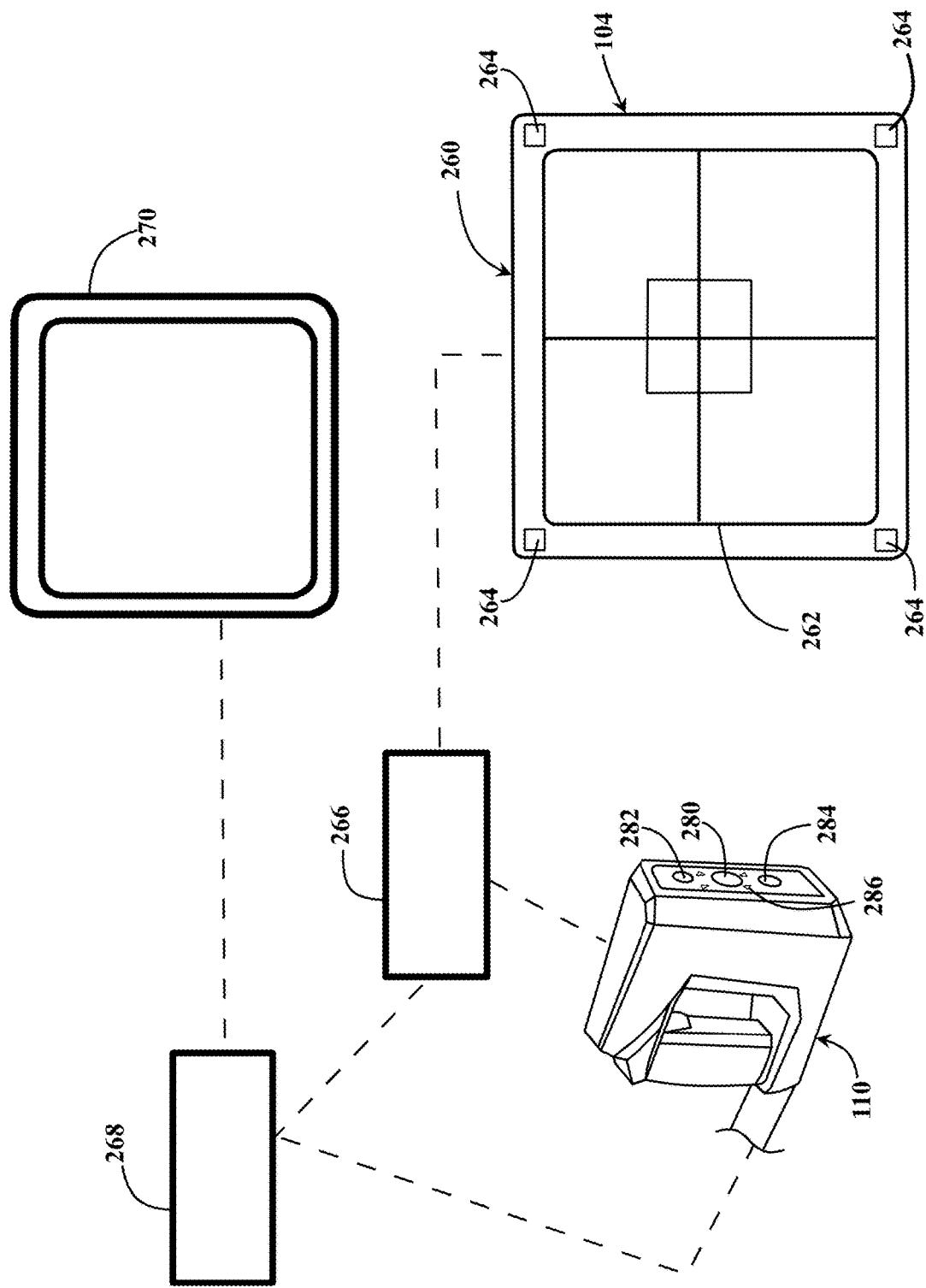
FIG. 30 illustrates another variation of an imaging system as described herein that uses a portable X-ray emitter and monitor to display one or more virtual images to assist in obtaining an X-ray image.

FIG. 30 illustrates another variation of an imaging system as described herein that uses a portable X-ray emitter 110. The X-ray emitter 110 can be free-standing or can be attached to a boom-type structure that allows for up to six degrees of freedom. As discussed above, the X-ray emitter 110 is configured with a positioning system using any number of position tracking elements 264 that are positioned around a perimeter of an imaging sensor 262 that receives an X-ray emission from the emitter 110 to produce an X-ray image. The imaging sensor 262 can be located in a housing 260 that comprises a working area for positioning of the object to be imaged. Alternatively, the sensor 262 can be positioned in a table structure or other structure as discussed above.

The position tracking elements 264 communicate with an X-ray positioning control system 266 that is configured to determine the relative location of the image sensor 262 and emitter 110. The X-ray positioning system 266 can be any of a variety of positioning systems including but not limited to the positioning system as described herein and can use line-of-sight emitters, non-line-of-sight sensors, or a combination thereof.

The system shown in FIG. 30 also illustrates the emitter 110 as having one or more cameras 282 adjacent to an emitter window 280. Variations of the system can include an emitter 110 as having dual stereoscopic cameras 282, 284 positioned about the emitter window 280. Alternatively, a single camera 282 or 284 can be used. As shown, the emitter 110 can optionally include lidar sensors 286 for additional positioning, imaging, and depth-sensing functionality, as well as any additional sensors disclosed herein.

The camera(s) 282 and/or 284 transmit signals to a processing unit 268, which produces an image of the field of view from the emitter 110 using the camera signal. The processing unit 268 is also configured to use the positioning data from the positioning system controller 266 to generate a first virtual representation of the imaging sensor 262 and overlays this image onto the image of the field of view from the emitter 110 as discussed below. The image and the first virtual representation of the imaging sensor 262 can be viewed on one or more display units 270. In one variation, the display unit 270 comprises a screen on a portion of the emitter 110. Alternatively, or in combination, the display unit can be a monitor within the examination area. In addition, the processing unit 268 can allow for broadcasting of the virtualized image to allow for remote viewing of the virtualized image. In additional variations, the X-ray positioning system 266 can be combined with the processing unit 268.

Figure 31A:
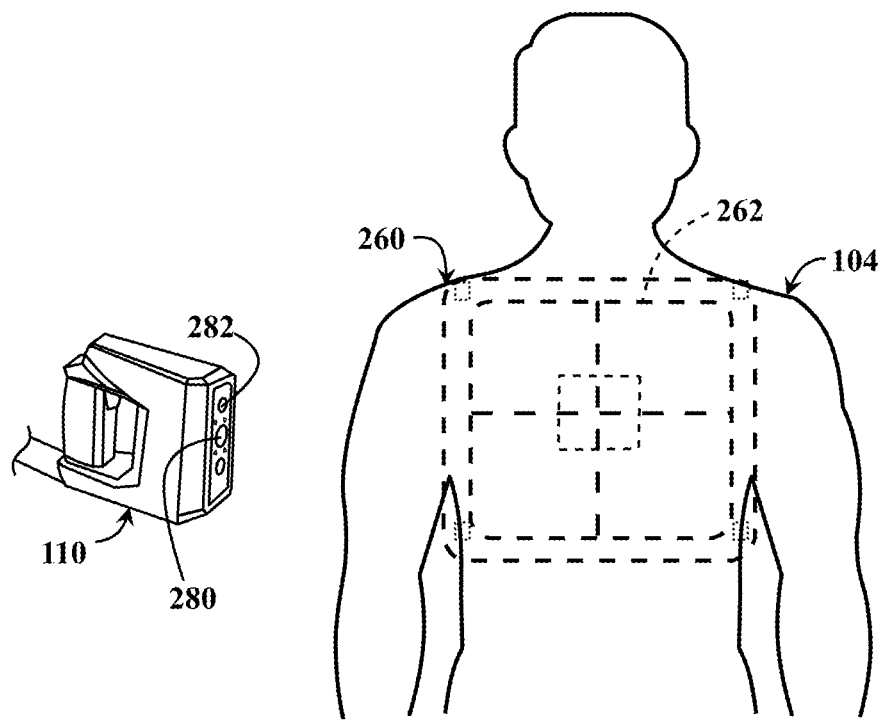
FIGS. 31A and 31B illustrate the initial stages of an attempt to capture an X-ray image of an individual patient that is adjacent to an image sensor of an obscured image sensing housing.
Figure 31B:
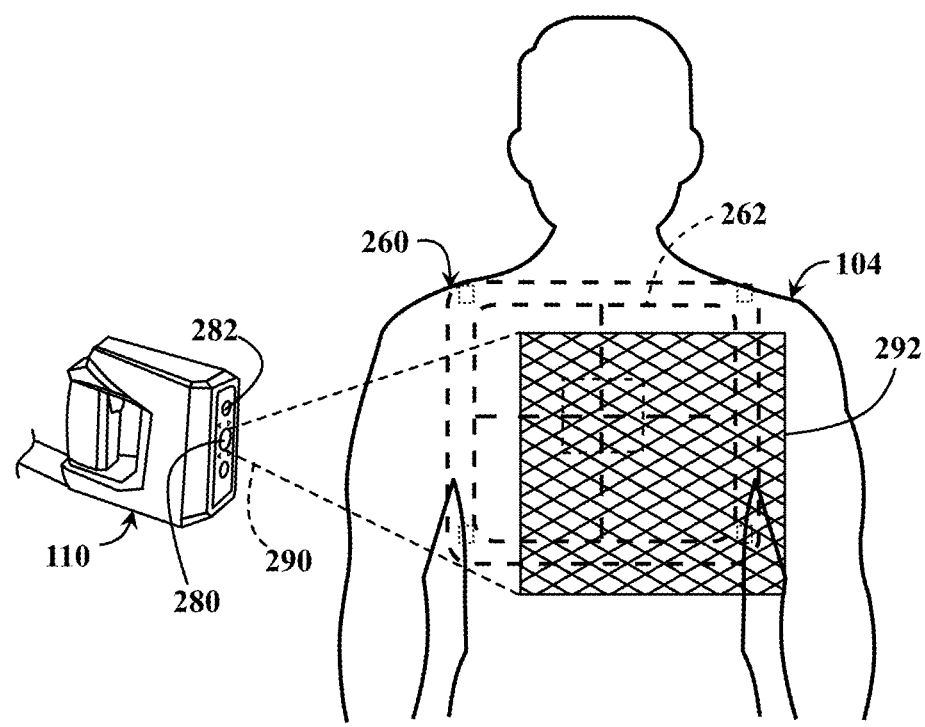

FIGS. 31A and 31B illustrate initial stages of an attempt to capture an X-ray image of an individual patient 104 that is adjacent to an image sensor 262 of an image sensing housing 260 where the individual patient 104 obscures a majority of the housing 260 and/or image sensor profile 262. The illustration shown is for explanatory purposes as the same principles apply if the image obtained was a body portion (e.g., a leg, shoulder, torso, etc.) where the body portion obscures the image sensor 262 such that an operator of the X-ray cannot visually confirm alignment of the body/body portion on the housing 260 with the image sensor outline 262. FIG. 31B illustrates where a projection of an X-ray emission 290 would produce an emission projection area 292 on the individual 104. However, in some variations, the X-ray system allows the operator to determine an outline of the projection area 292 using a light-field generated by the emitter 110. This allows the operator to visualize the area of the X-ray emission without generating X-ray radiation.

As shown in FIG. 31B, because the X-ray detector housing 260/sensor 262 is obscured by the patient's torso 104, the operator can inadvertently incorrectly position the X-emitter 110 such that the emission projection area 292/light field is, unknowingly, misaligned with the image sensor 262. This misalignment results in an X-ray image having a compromised field-of-view the projection area 292. Positioning of the camera 282 adjacent to the emitter window 280 permits the camera to obtain a similar field-of-view as the emitter window 280. In variations of the system, the camera(s) 282 can use image stabilization or actuators to shift a perspective of the camera image so that the camera image is always displayed normal to the image sensor.

Figure 32:
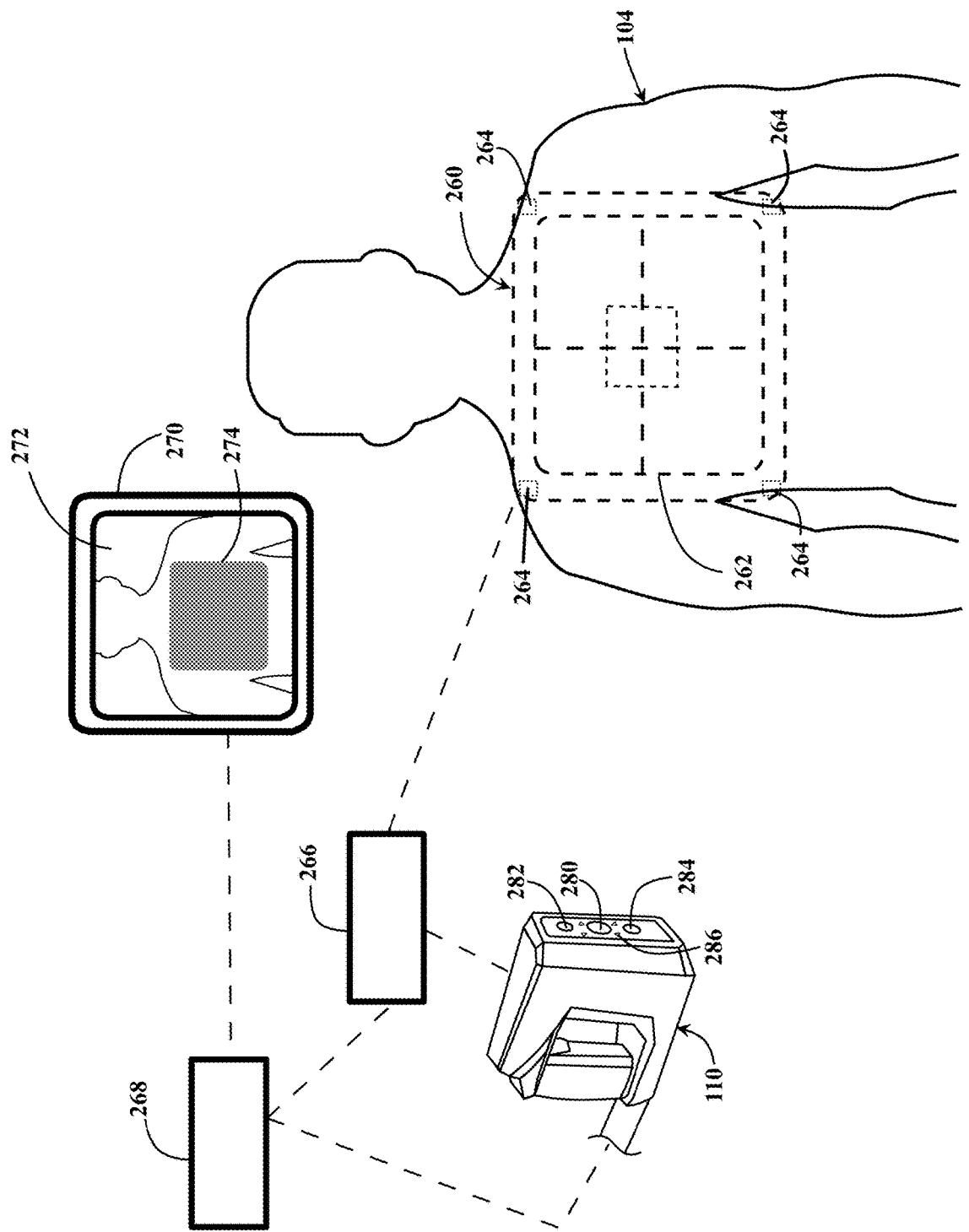
FIG. 32 represents a display of a first virtual representation of the boundary of the imaging sensor on the display.

FIG. 32 represents a display of a first virtual representation 274 of the boundary of the imaging sensor 262 on the display 270. As shown, the image 272 allows an X-ray user to observe the area of the individual 104 that is aligned with the imaging sensor 262. The image 272 can be a still capture image, real-time video, or a video segment when the user actuates a setting prior to emitting X-ray energy from the emitter. As shown, the point-of-view of the camera 282 will match or be sufficiently close to a point-of-view of the emitting window 280 such that the image 272 view corresponds with the ultimate X-ray image. The system shown in FIG. 32 can also optionally show a light field (as shown in FIG. 31B) on the patient 104 as well as a virtual representation of the light field/X-ray projection area on the monitor 270 prior to discharging X-ray emission from the emitter.

Figure 33A:
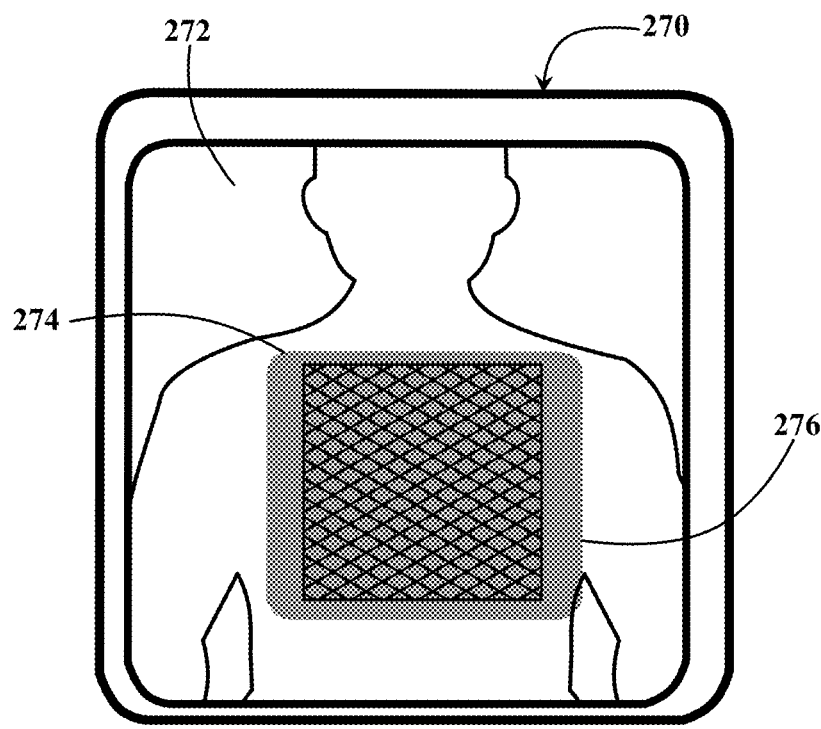
FIGS. 33A and 33B show additional examples of images overlayed with virtual images of the boundary of an imaging sensor.
Figure 33B:
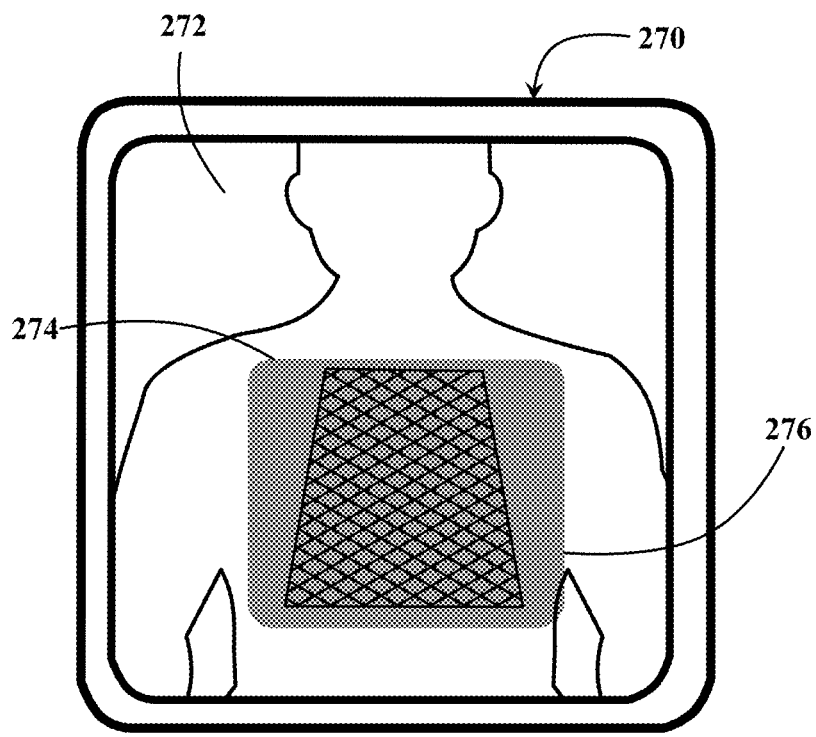

FIGS. 33A and 33B show additional examples of images 272 overlayed with virtual images 274 of the boundary of an imaging sensor. FIGS. 33A and 33B also show second virtual images 276 that represents the area of X-ray radiation emitted from the emitter that will be incident on the individual and image sensor. If the system uses a light-field projection from the emitter, the second virtual image 276 can correspond to the light-field projection on the patient. In this way, the operator can use both virtual images 274 and 276 to ensure that the intended object of the X-ray image is within the overlapping areas. FIG. 33A illustrates a condition where the emitter (not shown in FIG. 33A) is in a normal direction to the object and the image sensor. FIG. 33B illustrates a variation of a system where the camera image 272 is shifted in perspective to appear normal to the patient and image sensor either through movement of the camera on the emitter or via digital processing of the image. However, FIG. 33B shows skewing of the projected X-ray projection area through skewing of the second virtual image 276 representing the X-ray emission area. This feature allows a user to recognize that the emitter is not positioned in a normal direction relative to the object when viewing the monitor 270.

Figure 34A:
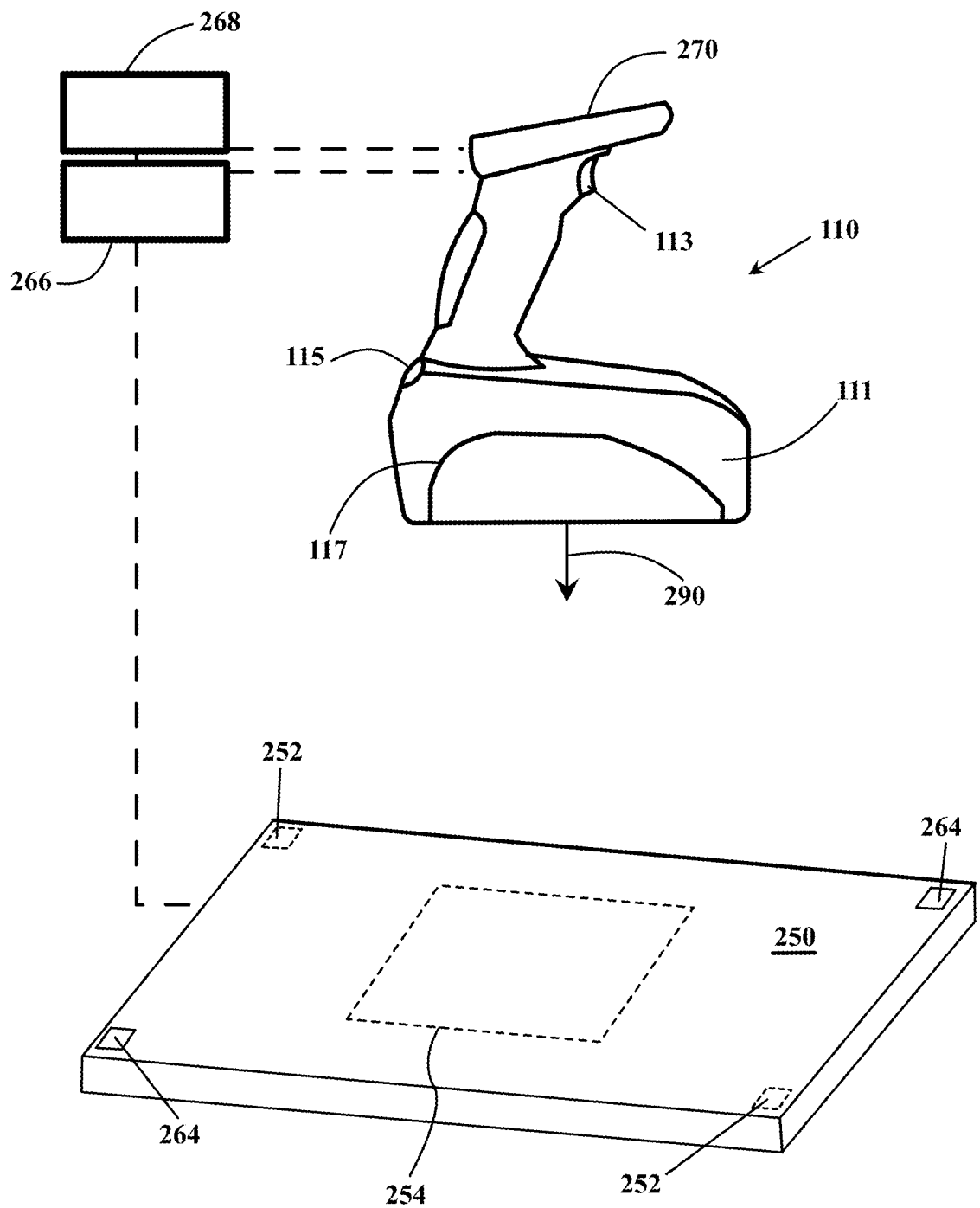
FIGS. 34A to 34C shows another variation of an emitter having a screen that allows operation of the emitter and observation of the monitor in two configurations.

FIG. 34A shows another variation of an X-ray system using both non-line-of-sight-tracking elements such as electromagnetic tracking sensors 252 and line-of-sight elements 264 as described above. Again, any variation of the system disclosed herein can include either non-line-of-sight tracking elements, line-of-sight tracking elements, or a combination of elements. FIG. 34A also illustrates an X-ray emitter 110 having a screen 270 on an end of the unit 110 opposite to a body 111 that carries the hardware and emitting apparatus of the unit. In such an example, the emitter window is located on the bottom face of the body 111 such that a field of view 290 of an emission or camera is directed away from the body 111, as shown by 290. The emitter 110 operates as discussed herein where any number of sensors 252 and/or 264 can be used as required. In operation, the sensors 252 and/or 264 allow the system 266 to determine the relative location of the emitter 110 relative to the image sensor 254. As discussed above, the emitter 110 includes one or more cameras (not shown in 34A) that transmit signals to a processing unit 268, which produces an image of the field of view from the emitter 110 using the camera signal that can be displayed on the emitter 110 via a monitor 270 or on a separate monitor. In the variation of the emitter 110 shown in FIG. 34A, the emitter includes a first trigger 113 and a second trigger 115 that allow a user to grip the emitter in different configurations depending on the X-ray image required. Moreover, the emitter 110 can include any number of features (e.g., a side contour, graphic, etc.) to provide a physical visual indicator to show where the X-ray emission exits the emitter 110.

Figure 34B:
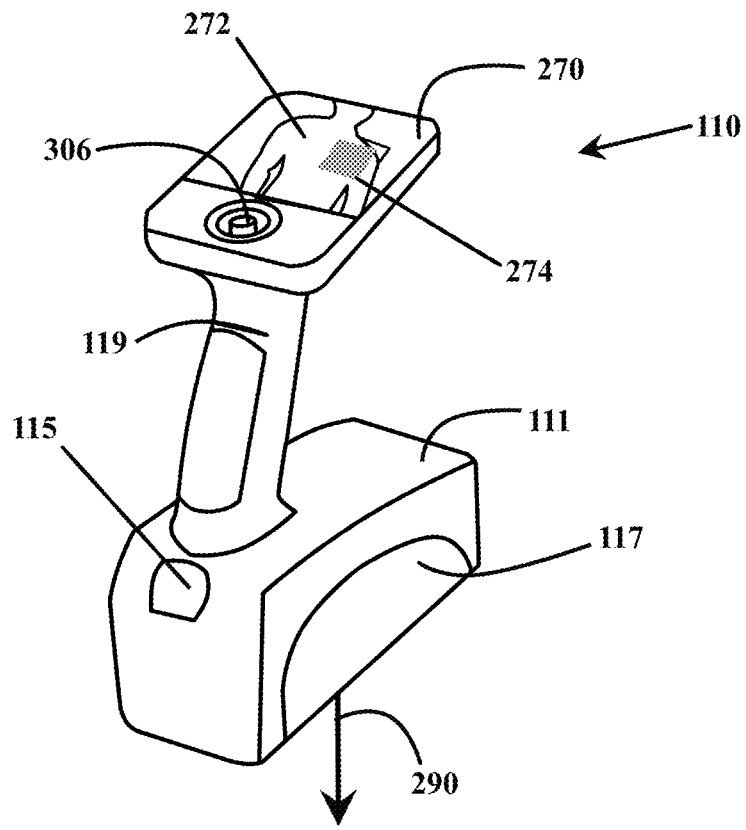
Figure 34C:
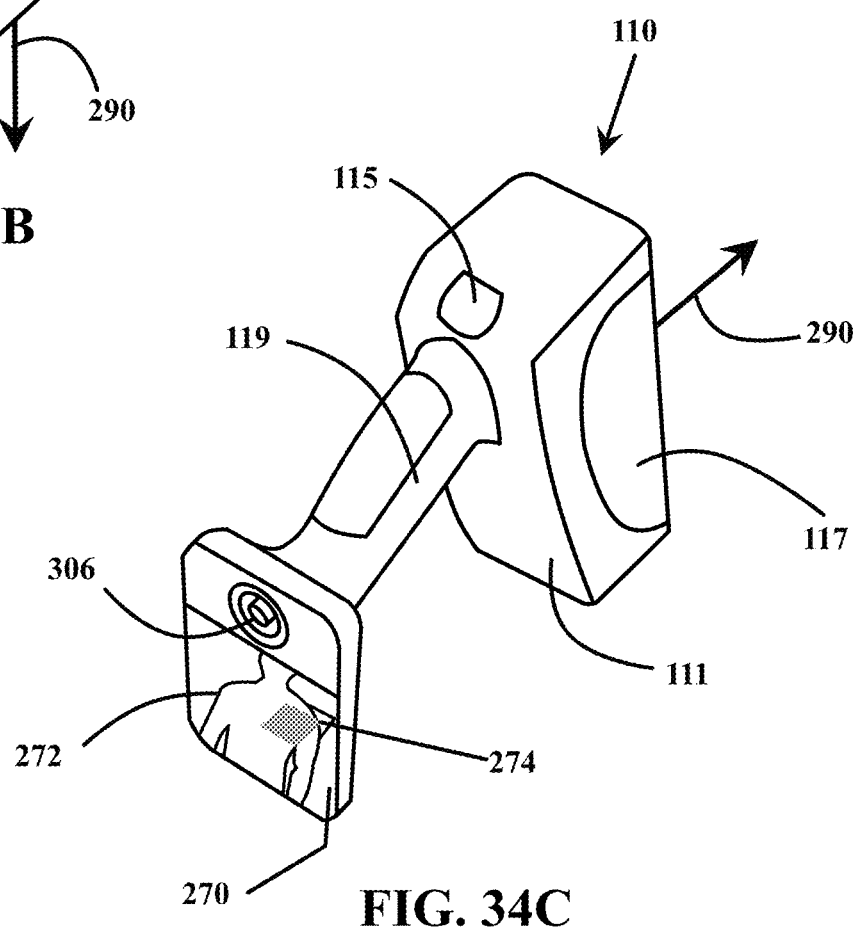

FIGS. 34B and 34C illustrate the emitter 110 shown in FIG. 34A, where a grip portion 119 of the emitter 110 is located between the body 111 and the monitor 270. This configuration permits operation of the emitter 110 in two different configurations. FIG. 34B shows a configuration where the emitter 110 is held over the object/patient such that the field of view 290 of the emission and camera exits in a bottom direction. In such a case, the operator can view the image 272 as well as the virtual image 274 of the image sensor on the monitor 270 while using a control switch 306. The first activation trigger (shown in FIG. 34A) can be accessed by the same hand grasping the grip portion 119. In FIG. 34C, the operator points the bottom of the body 110 in a direction to the object being imaged, as shown by field-of-view 290. In this variation, the operator can view the monitor 270 and adjust the control knob 306 while accessing the second trigger 115 with a thumb. It is noted that the monitor shown in FIGS. 34A to 34C can provide the same information as shown in FIG. 33A or 33B.

While the above descriptions provide exemplary details of the invention in order to provide an understanding of the invention, routine engineering adjustments may be employed to practice the invention without departing from the spirit or scope of the invention. Further, while the invention is described for use in X-ray imaging for surgical purposes, it could be used in other medical applications such as general medical imaging, veterinary, and bone densitometry. The system and method may also be used for non-medical applications such as industrial imaging, metal fatigue inspections, weld-inspection, for security inspections, and the like.

The invention claimed is:

1. A non-invasive imaging system for confirming placement of an object positioned in an examination area, the non-invasive imaging system comprising:
   a non-invasive imaging sensor having a detecting perimeter configured to receive an emission energy allowing for generation of a non-invasive image of the object when the object is positioned on or adjacent to the non-invasive imaging sensor;
   a plurality of position tracking implements fixedly positioned relative to the non-invasive imaging sensor;
   an emitting apparatus having an aperture opening that is configured to emit the emission energy in an emission profile, the emitting apparatus further including a position tracking apparatus configured to produce a positioning signal and a camera system configured to produce an image signal, where the positioning signal is produced upon detecting one or more of the plurality of position tracking implements;

a display configured to receive the image signal to produce a real-time image having a point of view from the aperture opening; and a control system configured to convert the positioning signal into a plurality of positioning data of the emitting apparatus relative to the non-invasive imaging sensor, the control system further configured to use the positioning data to generate a first virtual image of the detecting perimeter and a second virtual image of the emission profile, where the control system is further configured to display the first virtual image and the second virtual image with the real-time image on the first display.

2. The non-invasive imaging system of claim 1, wherein the control system is configured to display the first virtual image and the second virtual image with the real-time image on the display prior to the emitting apparatus emitting the emission energy.

3. The non-invasive imaging system of claim 1, wherein the position tracking apparatus comprises a first camera device in the camera system configured to detect one or more of the plurality of position tracking implements to produce the positioning signal and where the camera system comprises a second camera device configured to produce the image signal.

4. The non-invasive imaging system of claim 3, wherein the second camera device comprises at least two image sensors positioned adjacent to the aperture opening.

5. The non-invasive imaging system of claim 3, wherein the second camera device is positioned adjacent to the aperture opening.

6. The non-invasive imaging system of claim 3, where the first camera device comprises an infrared camera device.

7. The non-invasive imaging system of claim 1, further comprising a distance sensor coupled to the emitting apparatus, where the control system prevents the emitting apparatus from emitting the emission energy until the distance sensor detects a minimum distance to the object.

8. The non-invasive imaging system of claim 1, wherein the control system is configured to change a size or a profile of an aperture adjacent to the aperture opening in response to the positioning data.

9. The non-invasive imaging system of claim 1, wherein the camera system is configured to move in response to the positioning data to alter an orientation of the real-time image.

10. The non-invasive imaging system of claim 1, wherein the real-time image comprises a real-time video.

11. The non-invasive imaging system of claim 1, wherein the real-time image comprises at least one non-video image.

12. The non-invasive imaging system of claim 1, wherein the real-time image comprises a digitized image or a virtual image.

13. The non-invasive imaging system of claim 1, wherein the emission energy comprises an X-ray energy emission.

14. The non-invasive imaging system of claim 1, wherein the display is positioned on the emitting apparatus and separated from an emitter body by a grip, wherein the aperture opening is located on the emitter body, the emitting apparatus further including a first trigger located towards the display and a second trigger located towards the emitter body, wherein the first trigger is configured for operation with a finger of an operator and the second trigger is configured for operation with a thumb of the operator.

* * * * *